United States Patent
Yamamoto et al.

(10) Patent No.: US 9,336,349 B2
(45) Date of Patent: May 10, 2016

(54) METHOD FOR PRODUCING RNA-CONTAINING PROBE FOR DETECTING A TARGET NUCLEOTIDE

(75) Inventors: Junko Yamamoto, Ostsu (JP); Tomoo Inden, Otsu (JP); Toshiharu Ohba, Otsu (JP); Tooru Suzuki, Otsu (JP); Hiroyuki Mukai, Otsu (JP); Kiyozo Asada, Otsu (JP)

(73) Assignee: Takara Bio Inc., Shiga (JP)

( * ) Notice: Subject to any disclaimer, the term of this patent is extended or adjusted under 35 U.S.C. 154(b) by 72 days.

(21) Appl. No.: 13/812,242

(22) PCT Filed: Jul. 28, 2011

(86) PCT No.: PCT/JP2011/067299
§ 371 (c)(1),
(2), (4) Date: Jan. 25, 2013

(87) PCT Pub. No.: WO2012/014988
PCT Pub. Date: Feb. 2, 2012

(65) Prior Publication Data
US 2013/0122503 A1    May 16, 2013

(30) Foreign Application Priority Data
Jul. 29, 2010   (JP) .................. 2010-169927

(51) Int. Cl.
  *C12Q 1/68*   (2006.01)
  *G06F 19/12*  (2011.01)
  *G06F 19/20*  (2011.01)

(52) U.S. Cl.
  CPC .............. *G06F 19/12* (2013.01); *C12Q 1/6816* (2013.01); *C12Q 1/6876* (2013.01); *G06F 19/20* (2013.01); *C12Q 2527/107* (2013.01)

(58) Field of Classification Search
  None
  See application file for complete search history.

(56) References Cited

U.S. PATENT DOCUMENTS

| | | | |
|---|---|---|---|
| 5,556,749 A | 9/1996 | Mitsuhashi et al. | |
| 5,660,988 A | 8/1997 | Duck et al. | |
| 2004/0203008 A1 | 10/2004 | Uemori et al. | |
| 2009/0175876 A1* | 7/2009 | Gao et al. ............ | 424/139.1 |

FOREIGN PATENT DOCUMENTS

| | | |
|---|---|---|
| CN | 1483082 | 3/2004 |
| CN | 1854309 | 11/2006 |
| EP | 1312682 | 5/2003 |
| JP | 8-503091 | 4/1996 |
| JP | 2005/516296 | 6/2005 |
| WO | 03/064694 | 8/2003 |
| WO | 2009/094597 | 7/2009 |

OTHER PUBLICATIONS

English translation of the International Preliminary Report on Patentability for PCT/JP2011/067299 dated Jan. 29, 2013.
M. Nakao et al., "Current Challenges in Bioinformation with Large Scale Genomic Data: Semantic Web for Integration of Multiple Distributed Data Sources", Joho Shori (Monthly IPSJ Magazine), vol. 50, No. 9, pp. 836-844, 2009 with English translation.
T. Ito, "The Visualization Technique that will make your Effective Understanding of Genomic Data", Joho Shori (Monthly IPSJ Magazine), vol. 47, No. 3, pp. 241-248, Mar. 15, 2006 with English translation.
Chinese Office Action and Search Report dated Feb. 4, 2015 issued in corresponding Chinese Patent Application No. 201180037317.7. (with English Translation).
Korean Office Action dated Aug. 19, 2015, issued in counterpart Korean Patent Application No. 10-2013-7002715 (with English Translation).
Harvey et al., "Characterization and applications of CataCleave probe in real-time detection assays", Analytical Biochemistry, 2004, vol. 333, pp. 246-255.

* cited by examiner

*Primary Examiner* — James Martinell
(74) *Attorney, Agent, or Firm* — Wenderoth, Lind & Ponack, L.L.P.

(57) ABSTRACT

An object of the present invention is to provide a simple and useful method for producing an RNA-containing probe for detecting a target nucleotide, a simple and useful method, device, and system for processing nucleotide sequence information, and a simple and useful method for detecting a target nucleotide. The present invention provides a method for processing nucleotide sequence information, the method comprising the step of generating partial nucleotide sequences which has 7 to 14 nucleotides and a Tm value of 25 to 40° C. and in which a target nucleotide or a nucleotide adjacent to the target nucleotide is located at a position between 3 and 5 nucleotides from the 3' or 5' end. The method according to the present invention is useful for simply and efficiently producing an RNA-containing probe for detecting a target nucleic acid, without the basis of researchers' experiences or guess, and are extremely useful not only in the field of genetic engineering, but also in the field of medical research.

6 Claims, 26 Drawing Sheets

Fig.26

| Step | Form of information |
|---|---|
| ST1 | String K (number x, string J, symbol i) |
| ST2 | String M (number x, string L, symbol c) |
| ST3 (ST18 to ST25) | String N (symbol i or c, number y, symbol z) |
| ST4 (ST31) | String P (string O, number y, symbol z, symbol ST31) |
| ST4 (ST32) | String Q (string O, number y, symbol z, symbol ST32) |
| ST4 (ST33) | String R (string O, number y, symbol r) |

| Nucleotide | Complementary nucleotide |
|---|---|
| A | T |
| T | A |
| G | C |
| C | G |

| Process h | String N |
|---|---|
| H1 | $ix\alpha$, $i(x+1)\beta$ |
| H2 | $ix\alpha$, $i(x+1)\beta$, $c(x+1)\gamma$ |
| H3 | $ix\alpha$ |
| H4 | $ix\alpha$, $c(x+1)\beta$ |
| H5 | $cx\alpha$, $i(x+1)\beta$ |
| H6 | $cx\alpha$, $i(x+1)\beta$, $c(x+1)\gamma$ |
| H7 | $cx\alpha$ |
| H8 | $cx\alpha$, $c(x+1)\beta$ |

Fig.29

| Letter representing a nucleotide | Result of determination (Is the nucleotide a purine nucleotide?) |
|---|---|
| A | Yes |
| T | No |
| G | Yes |
| C | No |

|   | ST31 | ST32 |
|---|------|------|
| α | 4    | 1    |
| β | 5    | 2    |
| γ | 6    | 3    |

74

|   | ST31 | ST32 |
|---|------|------|
| α | 3    | 1    |
| β | 4    | 2    |

75

|   | ST31 | ST32 |
|---|------|------|
| α | 2    | 1    |

| Criterion for determination | Result of determination |
|------------------------------|-------------------------|
| Tm < 25°C                    | No                      |
| 25°C ≤ Tm ≤ 40°C             | Yes                     |
| 40°C < Tm                    | No                      |

| Set ID | Probe ID | Sequence of probe 1 | Strand orientation | Strand length of probe 1 | Tm value of probe1 | Sequence of probe 2 | Strand orientation | Strand length of probe 2 | Tm value of probe2 | Sequence of upstream primer | Strand length of upstream primer | Tm value of upstream primer | Sequence of downstream primer | Strand length of downstream primer |
|---|---|---|---|---|---|---|---|---|---|---|---|---|---|---|
| 1 | 1 | caggaacc(A)ta | + | 11 | 28.79 | aggaacc(G)ta | + | 10 | 28.4 | AGGACTGTGTGTCCACTCCT | 20 | 57.406 | AACTGCTACTACCACTGCCTAC | 22 |
| 2 | 1 | caggaacc(A)ta | + | 11 | 28.79 | aggaacc(G)ta | + | 10 | 28.4 | CAGGACTGTGTCTCCACTC | 19 | 55.028 | CTACTACCACTGCCTACTACCA | 22 |
| 3 | 1 | caggaacc(A)ta | + | 11 | 28.79 | aggaacc(G)ta | + | 10 | 28.4 | CCGGAGAGCTTACGTTA | 17 | 52.38 | CTACCACTGCCTACTACCA | 19 |
| 4 | 2 | aggaacc(A)tag | + | 11 | 28.06 | aggaacc(G)ta | + | 10 | 28.4 | AGGACTGTGTGTCCACTCCT | 20 | 57.406 | AACTGCTACTACCACTGCCTAC | 22 |
| 5 | 2 | aggaacc(A)tag | + | 11 | 28.06 | aggaacc(G)ta | + | 10 | 28.4 | CAGGACTGTGTGTCTCCACTC | 19 | 55.028 | CTACTACCACTGCCTACTACCA | 22 |
| 6 | 3 | CACTACTAT(G)GT | − | 12 | 30.52 | ACTACTAC(G)GT | − | 11 | 30.32 | CTCAGGTCAGTCTTGTGAG | 19 | 57.525 | GTGAGGTCACTCTTGAGA | 20 |
| 7 | 3 | CACTACTAT(G)GT | − | 12 | 30.52 | ACTACTAC(G)GT | − | 11 | 30.32 | TGATCTCAGGTGGGTGTTG | 19 | 57.918 | CAGCCTTGAGGTCACTCTTG | 20 |
| 8 | 3 | CACTACTAT(G)GT | − | 12 | 30.52 | ACTACTAC(G)GT | − | 11 | 30.32 | GTGAGGCAGGGCTGTAA | 17 | 55.549 | CAGGTCTGAGAGAAGAAGG | 19 |
| ... | ... | ... | ... | ... | ... | ... | ... | ... | ... | ... | ... | ... | ... | ... |

78

METHOD FOR PRODUCING RNA-CONTAINING PROBE FOR DETECTING A TARGET NUCLEOTIDE

This application is a U.S. national stage of International Application No. PCT/JP2011/067299 filed Jul. 28, 2011.

TECHNICAL FIELD

The present invention, in a first aspect, relates to a method for processing nucleotide sequence information, device for processing nucleotide sequence information, system for processing nucleotide sequence information, method, for producing an RNA-containing probe for detecting a target nucleotide, and a method for detecting a target nucleotide.

The present invention, in a second aspect, relates to a method for designing an RNA-containing probe useful for detecting a target nucleic acid, a method for processing a nucleotide sequence for use in the designing, and a program and recording medium allowing a computer to execute such a nucleotide sequence processing method. In addition, the present invention relates to a device for carrying out such a nucleotide sequence processing method.

BACKGROUND ART

Technologies for amplifying or detecting nucleic acids have been indispensable in the fields of medicine; pharmacy; agriculture, forestry, and fishery; and food, for example, as experimental tools not only in genetic engineering and molecular biology, but also in the diagnosis of diseases, examination of genetically modified foods, and detection of microorganisms, viruses, and pathogenic bacteria.

It is known that, regardless of their biological species, there is a group of genes which share high homology in genes that encode substances, enzymes, and others having similar functions. It is also known that the individual genomes of organisms belonging to the same species are not perfectly identical and have differences in their nucleotide sequences which are referred to as polymorphism. The polymorphism is known to exhibit a deletion or an insertion of one to several ten nucleotides, a duplication of a specific nucleotide sequence, and the like. Substitutions of a nucleotide with another nucleotide are referred to as a single nucleotide polymorphism (SNP; which may be described herein as a single nucleotide substitution) and have attracted attention as an indicator for searching genes related to diseases, determining the susceptibility to diseases, or understanding differences in the sensitivity to drugs (effects and side effects). Studies are also underway on methods for the detection of such substitutions.

Methods for detecting a particular gene from a group of genes sharing high homology and for detecting an SNP include a method in which an RNA-DNA hybrid formed by hybridization of an RNA-containing probe and a target. DNA is subjected to cleavage with ribonuclease (for example, Patent Document-1). In this method, the RNA-containing probe is designed such that the hybrid is not cleaved with ribonuclease when there is a mismatch between the probe and a target DNA, thereby allowing one to ascertain the presence or absence of a specified nucleotide or a nucleotide substitution in the target DNA.

Conventional probes for gene detection have been designed by selecting such a nucleotide sequence that specific hybridization occurs between the probe and a target nucleic acid, using as an indicator the Tm value of a hybrid which is to be formed or the self-complementarity of the probe, based on the nucleotide sequence of the target nucleic acid. A variety of software for designing appropriate probes is also provided.

However, the RNA-containing probe as described above which is for detecting a target nucleic acid can be designed only in a region which includes or does not include a specified nucleotide, or which includes a specified nucleotide at which a nucleotide substitution is caused or is likely to be caused, and thus has a limitation in selecting regions, as compared with cases where conventional probes are designed. Further, it is required that the sensitivity of the RNA portion contained in the probe to ribonuclease H varies to a great extent, depending upon the presence/absence of a specified nucleotide or SNP. Up until now, these limitations have forced researchers to have no choice but to design RNA-containing probes on the basis of their experiences or under trial and error.

PRIOR ART DOCUMENT

Patent Document

Patent Document 1: U.S. Pat. No. 5,660,988

SUMMARY OF THE INVENTION

Problems to be Solved by the Invention

An aim of the present invention, in a first aspect, is to provide a simple and useful method for producing an RNA-containing probe for detecting a target nucleotide, a simple and useful method, device, and system for processing nucleotide sequence information, and a simple and useful method for detecting a target nucleotide.

An aim of the present invention, in a second aspect, is to provide a simple and useful method for designing an RNA-containing probe for detecting a target nucleic acid, and a simple and useful method, device, and system for processing a nucleotide sequence.

Means for Solving the Problems

The present inventors have devoted themselves to research on designing an RNA-containing probe for detecting a target nucleic acid, which has been previously designed by researchers through trial and error for each specified nucleotide or single nucleotide substitution in a target nucleic acid which is to be detected, in order to solve the above-mentioned problems. The present inventors have examined a large number of combinations of conditions on a combination-by-combination basis, with the result that the RNA-containing probes designed as the sequences which meet particular conditions are found to be capable of efficient detection of a specified nucleotide or SNP when they used in combination with ribonuclease H, thereby resulting in the completion of the present invention. The present inventors have also developed a nucleotide sequence processing method for designing the above-mentioned RNA-containing probe; a program allowing a computer to execute the processing method; a nucleotide sequence processing device; and further a system for processing a nucleotide sequence which designs an RNA-containing probe for detecting a target nucleic acid and in addition, provides information about a pair of primers capable of efficient detection of a specified nucleotide or single nucleotide substitution, only by entering the nucleotide sequence information of the target nucleic acid from a client device connected to the nucleotide sequence processing device in a state capable of communication therewith via a network. Thereby the inventors have completed the present invention.

Accordingly, when summarized, the present invention, in a first aspect, is directed to:

[1] A method for processing nucleotide sequence information which is carried out by a device for processing the nucleotide sequence information, the method comprising the steps of:

inputting position information of a target nucleotide into the nucleotide sequence to be inputted comprising the target nucleotide, the nucleotide adjacent to the 5' side of the target nucleotide, and the nucleotide adjacent to the 3' side of the target nucleotide, thereby to output a nucleotide sequence comprising the inputted position information of the target nucleotide;

generating a nucleotide sequence comprising the position information of the target nucleotide which is complementary to the nucleotide sequence to be outputted comprising the position information of the target nucleotide;

generating a nucleotide sequence which is obtained by converting the target nucleotide or the nucleotide adjacent to the target nucleotide in the nucleotide sequence into an RNA, in the nucleotide sequence comprising the position information of the target nucleotide or the nucleotides each adjacent to the target nucleotide and the complementary nucleotide sequence thereof; and generating a partial nucleotide sequence comprising the position information of the target nucleotide or the nucleotides each adjacent to the target nucleotide, from the nucleotide sequence and the complementary nucleotide sequence thereof obtained by the RNA nucleotide conversion, wherein (d) the number of nucleotides in the partial nucleotide sequence is 7 to 14, (e) the Tm value of the partial nucleotide sequence is 25 to 40° C., and (f) the target nucleotide or the nucleotide adjacent to the target nucleotide in the nucleotide sequence is located at a position between 3 and 5 nucleotides from the 3' or 5' end.

[2] A method for processing nucleotide sequence information which is carried out by a device for processing the nucleotide sequence information, the method comprising the steps of:

inputting position information of a target-nucleotide into the nucleotide sequence to be inputted comprising the target nucleotide, the nucleotide adjacent to the 5' side of the target nucleotide, and the nucleotide adjacent to the 3' side of the target nucleotide, thereby to output a nucleotide sequence comprising the inputted position information of the target nucleotide;

generating a nucleotide sequence comprising the position information of the target nucleotide which is complementary to the nucleotide sequence to be outputted comprising the position information of the target nucleotide;

generating a partial nucleotide sequence comprising the position information of the target nucleotide or the nucleotides each adjacent to the target nucleotide, from the outputted nucleotide sequence and the generated complementary nucleotide sequence, wherein (d) the number of nucleotides in the partial nucleotide sequence is 7 to 14, (e) the Tm value of the partial nucleotide sequence is 25 to 40° C., and (f) the target nucleotide or the nucleotide adjacent to the target nucleotide in the nucleotide sequence is located at a position between 3 and 5 nucleotides from the 3' or 5' end; and generating a partial nucleotide sequence which is obtained by converting the target nucleotide or the nucleotide adjacent to the target nucleotide in the nucleotide sequence into an RNA, in the partial nucleotide sequence comprising the position information of the target nucleotide or the nucleotides each adjacent to the target nucleotide.

[3] A method for processing nucleotide sequence information which is carried out by a device for processing the nucleotide sequence information, the method comprising the steps of:

inputting position information of a target nucleotide into the nucleotide sequence to be inputted comprising the target nucleotide, the nucleotide adjacent to the 5' side of the target nucleotide, and the nucleotide adjacent to the 3' side of the target nucleotide, thereby to output a nucleotide sequence comprising the inputted position information of the target nucleotide;

generating a nucleotide sequence comprising the position information of the target nucleotide which is complementary to the nucleotide sequence to be outputted comprising the position information of the target nucleotide;

making at least one determination of the following determinations:

(a) a determination as to whether or not the target nucleotide is a purine nucleotide, (b) a determination as to whether or not the nucleotide adjacent to the 3' side of the target nucleotide is a purine nucleotide, and (c) a determination as to whether or not the nucleotide adjacent to the 5' side of the target nucleotide is a purine nucleotide, for the outputted nucleotide sequence and the generated complementary nucleotide sequence, whereby one nucleotide that is a purine nucleotide is determined as an RNA position from the outputted nucleotide sequence and the generated complementary nucleotide sequence, thereby to output a nucleotide sequence comprising the RNA position information;

generating a partial nucleotide sequence comprising the RNA position information, from the nucleotide sequence to be outputted comprising the RNA position information, wherein (d) the number of nucleotides in the partial nucleotide sequence is 7 to 14, (e) the Tm value of the partial nucleotide sequence is 25 to 40° C., and (f) the one nucleotide indicated at the RNA position is located at a position between 3 and 5 nucleotides from the 3' or 5' end; and generating a partial nucleotide sequence which is obtained by converting the nucleotide determined as the RNA position into an RNA, in the nucleotide sequence comprising the RNA position information or the partial nucleotide sequence comprising the RNA position information.

[4] The method for processing nucleotide sequence information according to [3], wherein the step of outputting the nucleotide sequence comprising the RNA position information comprises determining priorities for selecting a partial nucleotide sequence superior as an RNA-containing probe for detecting the target nucleotide, from the generated partial nucleotide sequences obtained by the RNA nucleotide conversion, based on the relative position between the target nucleotide and the determined RNA position; and outputting nucleotide sequences or partial nucleotide sequences comprising the determined priorities.

[5] A program carried out by a computer, comprising the steps of the method for processing nucleotide sequence information according to any one of [1] to [4].

[6] A computer-readable recording medium, characterized in that the medium stores the program according to [5].

[7] A device for processing nucleotide sequence information, comprising:

means for inputting position information of a target nucleotide into the nucleotide sequence to be inputted comprising the target nucleotide, the nucleotide adjacent to the 5' side of the target nucleotide, and the nucleotide adjacent to the 3' side of the target nucleotide, thereby to output a nucleotide sequence comprising the inputted position information of the target nucleotide;

means for generating a nucleotide sequence comprising the position information of the target nucleotide which is complementary to the nucleotide sequence to be outputted comprising the position information of the target nucleotide;

means for generating a nucleotide sequence which is obtained by converting the target nucleotide or the nucleotide adjacent to the target nucleotide in the nucleotide sequence into an RNA, in the nucleotide sequence comprising the position information of the target nucleotide or the nucleotides each adjacent to the target nucleotide and the complementary nucleotide sequence thereof; and means for generating a partial nucleotide sequence comprising the position information of the target nucleotide or the nucleotides each adjacent to the target nucleotide, from the nucleotide sequence which is obtained by the RNA nucleotide conversion and the complementary nucleotide sequence thereof, wherein (d) the number of nucleotides in the partial nucleotide sequence is 7 to 14, (e) the Tm value of the partial nucleotide sequence is 25 to 40° C., and (f) the target nucleotide or the nucleotide adjacent to the target nucleotide in the nucleotide sequence is located at a position between 3 and 5 nucleotides from the 3' or 5' end.

[8] A device for processing nucleotide sequence information, comprising:

means for inputting position information of a target nucleotide into the nucleotide sequence to be inputted comprising the target nucleotide, the nucleotide adjacent to the 5' side of the target nucleotide, and the nucleotide adjacent to the 3' side of the target nucleotide, thereby to output a nucleotide sequence comprising the inputted position information of the target nucleotide;

means for generating a nucleotide sequence comprising the position information of the target nucleotide which is complementary to the nucleotide sequence to be outputted comprising the position information of the target nucleotide;

means for generating a partial nucleotide sequence comprising the position information of the target nucleotide or the nucleotides each adjacent to the target nucleotide, from the outputted nucleotide sequence and the generated complementary nucleotide sequence, wherein (d) the number of nucleotides in the partial nucleotide sequence is 7 to 14, (e) the Tm value of the partial nucleotide sequence is 25 to 40° C., and (f) the target nucleotide or the nucleotide adjacent to the target nucleotide of the nucleotide sequence is located at a position between 3 and 5 nucleotides from the 3' or 5' end; and means for generating a partial nucleotide sequence which is obtained by converting the target nucleotide or the nucleotide adjacent to the target nucleotide in the nucleotide sequence into an RNA, in the partial nucleotide sequence comprising the position information of the target nucleotide or the nucleotides each adjacent to the target nucleotide.

[9] A device for processing nucleotide sequence information; comprising:

means for inputting position information of a target nucleotide into the nucleotide sequence to be inputted comprising the target nucleotide, the nucleotide adjacent to the 5' side of the target nucleotide, and the nucleotide adjacent to the 3' side of the target nucleotide, thereby to output a nucleotide sequence comprising the inputted position information of the target nucleotide;

means for generating a nucleotide sequence comprising the position information of the target nucleotide which is complementary to the nucleotide sequence to be outputted comprising the position information of the target nucleotide;

means for making at least one determination of the following determinations:

(a) a determination as to whether or not the target nucleotide is a purine nucleotide, (b) a determination as to whether or not the nucleotide adjacent to the 3' side of the target nucleotide is a purine nucleotide, and (c) a determination as to whether or not the nucleotide adjacent to the 5' side of the target nucleotide is a purine nucleotide, for the outputted nucleotide sequence and the generated complementary nucleotide sequence, whereby one nucleotide that is a purine nucleotide is determined as an RNA position from the outputted nucleotide sequence and the generated complementary nucleotide sequence, thereby to output a nucleotide sequence comprising the RNA position information;

means for generating a partial nucleotide sequence comprising the RNA position information, from the outputted nucleotide sequence comprising the RNA position information, wherein (d) the number of nucleotides in the partial nucleotide sequence is 7 to 14, (e) the Tm value of the partial nucleotide sequence is 25 to 40° C., and (f) the one nucleotide indicated at the RNA position is located at a position between 3 and 5 nucleotides from the 3' or 5' end; and means for generating a partial nucleotide sequence which is obtained by converting the nucleotide determined as the RNA position into an RNA, in the nucleotide sequence comprising the RNA position information or the partial nucleotide sequence comprising the RNA position information.

[10] The device for processing nucleotide sequence information according to [9], wherein the means for outputting the nucleotide sequence comprising the RNA position information comprises determining priorities for selecting a partial nucleotide sequence superior as an RNA-containing probe for detecting the target nucleotide, from the generated partial nucleotide sequences obtained by the RNA nucleotide conversion, based on the relative position between the target nucleotide and the determined RNA position; and outputting nucleotide sequences or partial nucleotide sequences comprising the determined priorities.

[11] A system for processing nucleotide sequence information, comprising the device for processing the nucleotide sequence information according to any one of [7] to [10] and a client device which are connected via a network, wherein the client device comprises transmission means for transmitting the information comprising the inputted nucleotide sequence to the device for processing the nucleotide sequence information via the network, and the device for processing the nucleotide sequence information comprises means for generating and outputting the generated partial nucleotide sequences obtained by the RNA nucleotide conversion, based on the transmitted information comprising the nucleotide sequence.

[12] A method for producing an RNA-containing probe for detecting a target nucleotide, which comprises the step of preparing a nucleic acid fragment containing RNA and DNA having the same sequence as a partial nucleotide sequence obtained by the RNA nucleotide conversion which is generated by the method for processing the nucleotide sequence information according to [1] to [4].

[13] A method for detecting a target nucleotide, which comprises the steps of hybridizing to nucleic acids in a sample an RNA-containing probe for detecting the target nucleotide which is produced by the method according to [12]; applying ribonuclease H treatment to the RNA-containing probe for detecting the target nucleotide, after the hybridization step; and detecting whether or not the RNA-containing probe for detecting the target nucleotide has been cleaved by the ribonuclease H.

Further, the present invention, in a second aspect, is directed to:

[1] A method for designing an RNA-containing probe for detecting a target nucleic acid, which comprises the step of creating a nucleotide sequence meeting the conditions that:
(a) one purine nucleotide is an RNA and the others are DNAs,
(b) a nucleotide sequence derived from a target nucleic acid to be detected or the complementary strand thereof has 7 to 14 nucleotides,
(c) the RNA nucleotide set forth in (a) is located at a position between 3 and 5 nucleotides from the 3' or 5' end, and
(d) the Tm value is in the range of 25 to 40° C.;

[2] The designing method according to [1], wherein the RNA nucleotide in step (a) is a nucleotide corresponding to a nucleotide selected from a nucleotide at which a single nucleotide substitution in the target nucleic acid is likely to be caused, the nucleotide adjacent to the 3' side of the nucleotide, a nucleotide in the complementary strand corresponding to a nucleotide at which a single nucleotide substitution in the target nucleic acid is likely to b caused, and the nucleotide adjacent to the 3' side of the nucleotide in the complementary strand;

[3] A method for detecting a target nucleic acid, which comprises the steps of designing an RNA-containing probe for detecting the target nucleotide, by the method according to [1] or [2]; synthesizing the probe; hybridizing the synthesized RNA-containing probe, to nucleic acids in a sample; and applying ribonuclease H treatment to examine whether or not the probe is cleaved by the ribonuclease H;

[4] A method for processing the nucleotide sequence of target nucleic acid for use in designing an RNA-containing probe for detecting the target nucleotide, which comprises:

a step of obtaining nucleotide sequence information, wherein the nucleotide sequence information of a target nucleic acid to be detected is obtained;

a step of making a determination of a nucleotide, wherein the determination is made as to whether or not a nucleotide selected from one nucleotide in the nucleotide sequence of the target nucleic acid, the nucleotide adjacent to the 3' side of the one nucleotide, the nucleotide in the nucleotide sequence of the complementary strand of the target nucleic acid corresponding to the one nucleotide, and the nucleotide adjacent to the side of the nucleotide in the nucleotide sequence of the complementary strand is a purine nucleotide;

a step of generating nucleotide information, wherein one of the purine nucleotides is set as an RNA and the others are set as DNAs;

a step of generating partial nucleotide sequences, wherein the number of nucleotides in nucleotide sequences derived from the target nucleic acid to be detected or the complementary strand thereof is set to be 7 to 14, thereby generating information about the partial nucleotide sequence;

a step of selecting nucleotide sequences, wherein nucleotide sequences in which the RNA nucleotide is located at a position between 3 and 5 nucleotides from the 3' or 5' end are selected based on the information of the partial nucleotide sequence; and a step of selecting specified-nucleotide-containing sequences, wherein sequences containing a specified nucleotide are selected, wherein the Tm value of the nucleotide sequences obtained by the nucleotide sequence selecting step is in the range of 25 to 40° C.;

[5] The method for processing the nucleotide sequence according to [4], further comprising a step of designing primers for amplification of the target nucleic acid, wherein a pair of primers for amplifying a fragment of the target nucleic acid which comprises a region corresponding to the designed RNA-containing probe is designed, based on the nucleotide sequence information of the target nucleic acid;

[6] The method for processing the nucleotide sequence according to [4], wherein the one nucleotide in the nucleotide sequence information is a nucleotide at which a single nucleotide substitution is likely to be caused;

[7] A program characterized by allowing a computer to execute the nucleotide sequence processing method according to [4] or [5];

[8] A computer-readable recording medium having the program according to [7] recorded thereon;

[9] A device for processing a target nucleic acid for use in designing an RNA-containing probe for detecting the target nucleic acid, comprising:

means for obtaining nucleotide sequence information, wherein the nucleotide sequence information of a target nucleic acid to be detected is obtained;

means for making a determination of a nucleotide, wherein the determination is made as to whether or not a nucleotide selected from one nucleotide in the nucleotide sequence of the target nucleic acid, the nucleotide adjacent to the 3' side of the one nucleotide, the nucleotide in the nucleotide sequence of the complementary strand of the target nucleic acid corresponding to the one nucleotide, and the nucleotide adjacent to the 3' side of the nucleotide in the nucleotide sequence of the complementary strand is a purine nucleotide;

means for generating nucleotide information, wherein one of the purine nucleotides is set as an RNA and the others are set as DNAs;

means for generating partial-nucleotide sequences, wherein the number of nucleotides in nucleotide sequences derived from the target nucleic acid to be detected or the complementary strand thereof is set to be 7 to 14, thereby generating information about the partial nucleotide sequences;

means for selecting nucleotide sequences, wherein based on the information about the partial nucleotide sequence, nucleotide sequences in which the RNA nucleotide is located at a position between 3 and 5 nucleotides from the 3' or 5' end are selected; and means for selecting specified-nucleotide-containing sequences, wherein sequences containing a specified nucleotide are selected, wherein the Tm value of the nucleotide sequences obtained by the nucleotide sequence selecting step is in the range of 25 to 40° C.;

[10] The device for processing the nucleotide sequence according to [9], further comprising means for designing primers for amplification of the target nucleic acid, wherein a pair of primers for amplifying a fragment of the target nucleic acid which comprises a region corresponding to the designed RNA-containing probe is designed, based on the nucleotide sequence information the target nucleic acid;

[11] The device for processing the nucleotide sequence according to [9], wherein the one nucleotide in the nucleotide sequence information is a nucleotide at which a single nucleotide substitution is likely to be caused; and

[12] A system for processing a nucleotide sequence comprising the nucleotide sequence processing device according to [9] or [10] and a client device connected to the nucleotide sequence processing device in a state capable of communication therewith via a network, characterized in that:

the client device comprises transmission means for transmitting the nucleotide sequence information of the target nucleic acid to the nucleotide sequence processing device, and means for obtaining information in the target nucleic acid about the RNA-containing probe for detecting the target nucleic acid, which is transmitted from the nucleotide sequence processing device, or information of the probe and about the primers for amplification of the target nucleic acid.

Effects of the Invention

According to the present invention, researchers can, simply design an RNA-containing probe for detecting target nucleic acid, which has been previously designed on the basis of their experiences or sense, and it is made possible to efficiently detect a target nucleic acid, as well as a specified nucleotide (which may be referred to herein as a target nucleotide) or SNP in a target nucleic acid. There is also provided information about a pair of primers capable of efficient detection of a specified nucleotide or single nucleotide substitution in a target nucleic acid, and thus an RNA-containing probe for detecting a target nucleic acid can be easily designed by researchers having little or no experience in detecting target nucleic acids and, it is made possible to efficiently detect a specified nucleotide- or SNP in a target nucleic acid of interest.

BRIEF DESCRIPTION OF THE DRAWINGS

FIG. 26 represents a table summarizing the form of data inputted or generated in ST1 to ST4.

FIG. 27 represents a table to which reference is made in process step ST2.

FIG. 28 represents a table showing string N generated in process steps ST18 to ST25.

FIG. 29 represents a table to which reference is made in determination steps ST11 to ST17.

FIG. 30 represents a table to which reference is made in process step ST33.

FIG. 31 represents a table to which reference is made in determination step ST5.

FIG. 32 represents a table of data outputted in process step ST10. In column three of the outputted table, probe ID 1 is represented by SEQ ID NO:36, Probe ID 2 is represented by SEQ ID NO:37, and probe ID 3 is represented by SEQ ID NO:38. In column 7 of the outputted table, the first five sequences from the top of the column are represented by SEQ ID NO:39 while the final three sequences are represented by SEQ ID NO:40. The sequences shown in column eleven of the outputted table are represented by SEQ ID NO:41, SEQ ID NO:42, SEQ ID NO:43, SEQ ID NO:41, SEQ ID NO:42, SEQ ID NO:44, SEQ ID NO:45, and SEQ ID NO:46, respectively from the top to the bottom of the column. The sequences shown in column fourteen of the outputted table are represented by SEQ ID NO:47, SEQ ID NO:48, SEQ ID NO:49, SEQ ID NO:47, SEQ ID NO:48, SEQ ID NO:50, SEQ ID NO:51, and SEQ ID NO:52, respectively from the top to the bottom of the column.

EMBODIMENTS FOR CARRYING OUT THE INVENTION

Figure 1:
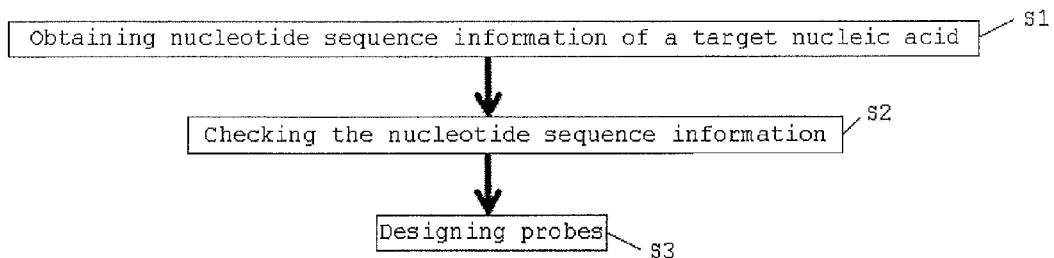
FIG. 1 represents a flow diagram showing the steps of a method for processing a nucleotide sequence according to the present invention.

The present invention will be specifically described below.

The present invention provides an RNA-containing probe used in a method by which a target nucleic acid is detected, based on whether or not the probe is cleaved by ribonuclease H after the probe is hybridized to the target nucleic acid. Regarding features of RNA-containing probes, designed according to the present invention, an explanation is given below to an RNA-containing probe for detecting nucleotide X at a specified position in a target nucleic acid, as an example. Here, nucleotide X may be any nucleotide in a target nucleic acid, for example, a nucleotide which has been substituted for the normal nucleotide as the result of a single nucleotide substitution, or a nucleotide which is usually found but likely to be substituted with another nucleotide. The nucleotide X described above may be also referred to herein as a target nucleotide.

An RNA-containing probe according to the present invention has a sequence which is capable of hybridization to a region comprising the above-mentioned nucleotide X in a target nucleic acid or to a region complementary to such a region. Therefore, the probe has a sequence which is a portion of the nucleotide sequence selected from the target nucleic acid or the complementary strand thereof and which hybridizes to a region comprising nucleotide X or the nucleotide complementary to nucleotide X in the complementary strand of the target nucleic acid (which is referred as to nucleotide Y). The strand length of such a sequence is not limited in particular and preferably is 7 to 14 nucleotides. At least one of nucleotide nucleotide Y, or the nucleotide adjacent to the 3' side of each of nucleotides X and Y is a purine nucleotide (adenine or guanine), and thus any one of these purine nucleotides is selected, so that only this nucleotide is set as an RNA and the others are set as DNAs when an RNA-containing probe according to the present invention is designed. For example, in cases where nucleotide X and the nucleotide adjacent to the 3' side of nucleotide X are pyrimidine nucleotides (cytosine or thymine), this condition can be satisfied by designing an RNA-containing probe from the sequence of the complementary strand of a target nucleic acid (setting nucleotide Y or the nucleotide adjacent to the 3' side of nucleotide Y as an RNA). For DNA nucleotides use can be made, for example, of dUTP, inosine, 7-DEAZA-GTP, 7-DEAZA-ATP, and LNA-modified DNA nucleotides, in addition to dATP, dCTP, dGTP, and dTTP. The RNA nucleotide is located at a position between 3 and 5 nucleotides from either the 3 or 5' end of the probe. In a preferable aspect, the RNA nucleotide is located at the position of the third or fourth nucleotide from either the 3' or 5' end of the probe. The Tm value of the probe is in the range of 25 to 40° C., preferably 25 to 32° C. Here, the Tm value is calculated under conditions having a DNA concentration of 500 nM and a salt concentration of 50 mM, using the nearest-neighbor method and further in the method described in Biochemistry, Vol. 36, No. 34, pp. 10581-10594 (1997).

RNA-containing probes meeting the above-mentioned conditions are more efficiently cleaved with ribonuclease H when the probe is hybridized to a target nucleic acid (DNA) comprising nucleotide X or the complementary strand thereof and subjected to treatment with ribonuclease H, than those which do not meet any one of the above-mentioned conditions. Therefore, RNA-containing probes meeting the above-mentioned conditions are capable of detecting the presence of nucleotide X in a target nucleic acid with high sensitivity.

In the method of the present invention for designing an RNA-containing probe for detecting a target nucleic acid, nucleotide sequence information of the target nucleic acid is first obtained. Here, "nucleotide sequence information of the target nucleic acid" is referred to the nucleotide sequence of the target nucleic acid and the position of one nucleotide in the nucleotide sequence. "The position of one nucleotide" is referred to the position of one nucleotide in the target nucleic acid which is desired to be detected. When an RNA-containing probe is designed to detect a particular gene from a group of genes to which the target nucleic acid exhibits a high degree of homology, homology analysis of the nucleotide sequences of these genes of the group is carried out in routine methods to find out, in their conserved regions or highly homologous regions, a nucleotide which exhibits a low degree of homology or is different between a target gene and the other genes, whereby the position of this nucleotide may be set as the position of the one nucleotide. When an RNA-containing probe is designed to detect an SNP, an RNA-containing probe may be designed by using as the above-mentioned one nucleotide a nucleotide which is estimated by genome analysis or the like for the SNP to be likely to be caused or a nucleotide at the position of the SNP described in open public databases. The nucleotide sequence is not limited in particular, if it is a sequence of nucleic acids, and preferably is a DNA sequence. In addition, the position of such a nucleotide in the nucleotide sequence may be at one or more than one location. In cases where such a nucleotide is at more than one location, the position at each of the more than one location is used as the position of the one nucleotide in the method of the present invention for designing an RNA-containing probe for detecting a target nucleic acid. Further, the nucleotide sequence information of the target nucleic acid may be any nucleotide sequence and the position of one nucleotide in the nucleotide sequence, or a nucleotide sequence obtained from a variety of open databases and the position of one nucleotide in the nucleotide sequence.

A set of sequences meeting the conditions set below is generated based on the nucleotide sequence information of the target nucleic acid:

(a) one purine nucleotide is an RNA and the others are DNAs;

(b) a nucleotide sequence derived from a target nucleic acid to be detected or the complementary strand thereof has 7 to 14 nucleotides;

(c) the RNA nucleotide set forth in (a) is located at a position between 3 and 5 nucleotides froth the 3' end, or alternatively at a position between 3 and 5 nucleotides from the 5' end; and (d) the Tm value is in the range of 25 to 40° C.

In cases where the position of the nucleotide is at more than one location, a set of sequences is generated for the position of each of the nucleotides at the more than one location.

When a set of sequences as described above is generated, the additional conditions set below are preferably applied:

(e) in condition (a), if there is present in the probe a sequence complementary to a sequence which ranges from the purine nucleotide set as an RNA to 2 nucleotides on the 5' side having a total of 3 nucleotides), or a sequence complementary to a sequence which ranges from 1 nucleotide on the 5' side to 1 nucleotide on the 3' side of the purine nucleotide set as an RNA (i.e., having a total of 3 nucleotides), then such a sequence is excluded from the set of sequences; and (f) a sequence comprising an inverted repeat nucleotide sequence (palindromic sequence) having a complementary portion of four nucleotides or more is excluded from the set of sequences.

In addition, it is preferable that when the set of sequences is generated, probes are ranked according to the criteria set below, depending upon whether in the above-mentioned conditions, conditions (a) and (c) are as described in any one of the sets of conditions which follow. In priorities 1 to 6 as described below, it is meant that the lower the numerical value, the higher the order of priority. "One nucleotide in a target nucleic acid" as described below indicates a target nucleotide and is also referred to as "the one nucleotide" in the priorities which follow.

1. In cases where one nucleotide in a target nucleic acid is a purine nucleotide and the nucleotide adjacent to each of the 3' and 5' sides of the one nucleotide is a purine, nucleotide:

Priority 1: (a) the one nucleotide is an RNA and the others are DNAs; and
(c) the RNA nucleotide set forth in (a) is located at a position between 3 and 5 nucleotides from the 3' end.

Priority 2: (a) the nucleotide adjacent to the 3', side of the one nucleotide is an RNA and the others are DNAs; and
(c) the RNA nucleotide set forth in (a) is located at a position between 3 and 5 nucleotides from the 3' end.

Priority 3 (a) the one nucleotide is an RNA and the others are DNAs; and
(c) the RNA nucleotide set forth in (a) is located at a position between 3 and 5 nucleotides from the 5' end.

Priority 4: (a) the nucleotide adjacent to the 3' side of the one nucleotide is an RNA and the others are DNAs; and
(c) the RNA nucleotide set forth in (a) is located at a position between 3 and 5 nucleotides from the 5' end.

2. In cases where one nucleotide in a target nucleic acid is a purine nucleotide, the nucleotide adjacent to the 3' side of the one nucleotide is a purine nucleotide, and the nucleotide adjacent to the 5' side of the one nucleotide is a pyrimidine nucleotide:

Priority 1: (a) the one nucleotide is an RNA and the others are DNAs; and
(c) the RNA nucleotide set forth in (a) is located at a position between 3 and 5 nucleotides from the 3' end.

Priority 2: (a) the nucleotide adjacent to the 3' side of the one nucleotide is an RNA and the others are DNAs; and
(c) the RNA nucleotide set forth in (a) is located at a position between 3 and 5 nucleotides from the 3' end.

Priority 3: (a) the nucleotide adjacent to the 3' side of the nucleotide in the complementary strand (antisense strand) corresponding to the one nucleotide is an RNA and the others are DNAs; and
(c) the RNA nucleotide set forth in (a) is located at a position between 3 and 5 nucleotides from the 3' end.

Priority 4: (a) the one nucleotide is an RNA and the others are DNAs; and
(c) the RNA nucleotide set forth in (a) is located at a position between 3 and 5 nucleotides from the 5' end.

Priority 5: (a) the nucleotide adjacent to the 3' side of the one nucleotide is an RNA and the others are DNAs; and
(c) the RNA nucleotide set forth in (a) is located at a position between 3 and 5 nucleotides from the 5' end.

Priority 6: (a) the nucleotide adjacent to the 3' side of the nucleotide in the antisense strand corresponding to the one nucleotide is an RNA and the others are DNAs; and
(c) the RNA nucleotide set forth in (a) is located at a position between 3 and 5 nucleotides from the 5' end.

3. In cases where one nucleotide in a target nucleic acid is a purine nucleotide, the nucleotide adjacent to the 3' side of the one nucleotide is a pyrimidine nucleotide, and the nucleotide adjacent to the 5' side of the one nucleotide is a purine nucleotide:

Priority 1: (a) the one nucleotide is an RNA and the others are DNAs; and
(c) the RNA nucleotide set forth in (a) is located at a position between 3 and 5 nucleotides from the 3' end.

Priority 2: (a) the one nucleotide is an RNA and the others are DNAs; and
(c) the RNA nucleotide set forth in (a) is located at a position between 3 and 5 nucleotides from the 5' end.

4. In cases where one nucleotide in a target nucleic acid is a purine nucleotide and the nucleotide adjacent to each of the 3' and 5' sides of the one nucleotide is a pyrimidine nucleotide:

Priority 1: (a) the one nucleotide is an RNA and the others are DNAs; and
(c) the RNA nucleotide set forth in (a) is located at a position between 3 and 5 nucleotides from the 3' end.

Priority 2 (a) the nucleotide adjacent to the 3' side of the nucleotide in the antisense strand corresponding to the one nucleotide is an RNA and the others are DNAs; and
(c) the RNA nucleotide set forth in (a) is located at a position between 3 and 5 nucleotides from the 3' end.

Priority 3: (a) the one nucleotide is an RNA and the others are DNAs; and
(c) the RNA nucleotide set forth in (a) is located at a position between 3 and 5 nucleotides from the 5' end.

Priority 4: (a) the nucleotide adjacent to the 3' side of the nucleotide in the antisense strand corresponding to the one nucleotide is an RNA and the others are DNAs; and
(c) the RNA nucleotide set forth in (a) is located at a position between 3 and 5 nucleotides from the 5' end.

5. In cases where one nucleotide in a target nucleic acid is a pyrimidine nucleotide and the nucleotide adjacent to each of the 3' and 5' sides of the one nucleotide is a purine nucleotide:

Priority 1: (a) the nucleotide in the antisense strand corresponding to the one nucleotide is an RNA and the others are DNAs; and (c) the RNA nucleotide set forth in (a) is located at a position, between 3 and 5 nucleotides from the 3' end.

Priority 2: (a) the nucleotide adjacent to the 3' side of the one nucleotide is an RNA and the others are DNAs; and (c) the RNA nucleotide set forth in (a) is located at a position between 3 and 5 nucleotides from the 3' end.

Priority 3: (a) the nucleotide in the antisense strand corresponding to the one nucleotide is an RNA and the others are DNAs; and (c) the RNA nucleotide set forth in (a) is located at a position between 3 and 5 nucleotides from the 5' end.

Priority 4: (a) the nucleotide adjacent to the 3' side of the one nucleotide is an RNA and the others are DNAs; and (c) the RNA nucleotide set forth in (a) is located at a position between 3 and 5 nucleotides from the 5' end.

6. In cases where one nucleotide in a target nucleic acid is a pyrimidine nucleotide, the nucleotide adjacent to the 3' side of the one nucleotide is a purine nucleotide, and the nucleotide adjacent to the 5' side of the one nucleotide is a pyrimidine nucleotide:

Priority 1: (a) the nucleotide in the antisense strand corresponding to the one nucleotide is an RNA and the others are DNAs; and (c) the RNA nucleotide set forth in (a) is located at a position between 3 and 5 nucleotides from the 3' end.

Priority 2: (a) the nucleotide adjacent to the 3' side of the one nucleotide is an RNA and the others are DNAs; and (c) the RNA nucleotide set forth in (a) is located at a position between 3 and 5 nucleotides from the 3' end.

Priority 3: (a) the nucleotide adjacent to the 3' side of the nucleotide in the antisense strand corresponding to the one nucleotide is an RNA and the others are DNAs; and (c) the RNA nucleotide set forth in (a) is located at a position between 3 and 5 nucleotides from the 3' end.

Priority 4: (a) the nucleotide in the antisense strand corresponding to the one nucleotide is an RNA and the others are DNAs; and (c) the RNA nucleotide set forth in (a) is located at a position between 3 and 5 nucleotides from the 5' end.

Priority 5: (a) the nucleotide adjacent to the 3' side of the one nucleotide is an RNA and the others are DNAs; and (c) the RNA nucleotide set forth in (a) is located at a position between 3 and 5 nucleotides from the 5' end.

Priority 6: (a) the nucleotide adjacent to the 3' side of the nucleotide in the antisense strand corresponding to the one nucleotide is an RNA and the others are DNAs; and (c) the RNA nucleotide set forth in (a) is located at a position between 3 and 5 nucleotides from the 5' end.

7. In cases where one nucleotide in a target nucleic acid is a pyrimidine nucleotide, the nucleotide adjacent to the 3' side of the one nucleotide is a pyrimidine nucleotide, and the nucleotide adjacent to the 5' side of the one nucleotide is a purine nucleotide:

Priority 1: (a) the nucleotide in the antisense strand corresponding to the one nucleotide is an RNA and the others are DNAs; and (c) the RNA nucleotide set forth in (a) is located at a position between 3 and 5 nucleotides from the 3' end.

Priority 2: (a) the nucleotide in the antisense strand corresponding to the one nucleotide is an RNA and the others are DNAs; and (c) the RNA nucleotide set forth in (a) is located at a position between 3 and 5 nucleotides from the 5' end.

8. In cases where one nucleotide in a target nucleic acid is a pyrimidine nucleotide and the nucleotide adjacent to each of the 3' and 5' sides of the one nucleotide is a pyrimidine nucleotide:

Priority 1: (a) the nucleotide in the antisense strand corresponding to the one nucleotide is an RNA and the others are DNAs; and (c) the RNA nucleotide set forth in (a) is located at a position between 3 and 5 nucleotides from the 3' end.

Priority 2: (a) the nucleotide adjacent to the 3' side of the nucleotide in the antisense strand corresponding to the one nucleotide is an RNA and the others are DNAs; and (c) the RNA nucleotide set forth in (a) is located at a position between 3 and 5 nucleotides from the 3' end.

Priority 3: (a) the nucleotide in the antisense strand corresponding to the one nucleotide is an RNA and the others are DNAs; and (c) the RNA nucleotide set forth in (a) is located at a position between 3 and 5 nucleotides from the 5' end.

Priority 4: (a) the nucleotide adjacent to the 3' side of the nucleotide in the antisense strand corresponding to the one nucleotide is an RNA and the others are DNAs; and (c) the RNA nucleotide set forth in (a) is located at a position between 3 and 5 nucleotides from the 5' end.

Also included in the present application is a method in which an RNA-containing probe obtained by the designing method as described above is used to detect a target nucleic acid. For example, an RNA-containing probe sequence with a high priority designed by the above-mentioned method is synthesized by known methods. The synthesized RNA-containing probe can be subjected to hybridization to nucleic acids in a sample, followed by treatment with ribonuclease H to examine whether or not the probe is cleaved by the ribonuclease H, thereby to detect the target nucleic acid in the sample. Procedures for examining whether or not the probe has been cleaved are not limited in particular, and known procedures for nucleic acid analysis can be used. For example, electrophoresis or high-performance liquid chromatography methods can be used to detect the cleavage of the probe from the change in its strand length. A particularly preferable aspect includes, for example, one in which an RNA-containing probe is labeled with two substances, a fluorescent substance and a substance having an action of quenching the fluorescence that is emitted by the fluorescent substance, wherein these substances are positioned at an appropriate distance at each side of the RNA nucleotide within the probe. Such an RNA-containing probe will hardly emit fluorescence in conditions where the probe is intact, but will generate fluorescence when the probe is cleaved and the distance between the fluorescent and quenching substances becomes large. Designing such an RNA-containing probe makes it possible to detect a target nucleic acid by observing the fluorescence which is emitted from reaction solutions under reaction. Various fluorescent and quenching substances are known and many of these are already commercially available. In the present invention, the detection of a target nucleic acid using an RNA-containing probe designed by the present invention can be carried out as a method for the detection of a specified nucleotide or whether or not the specified nucleotide is present, especially the detection of the presence of a nucleotide which occurs in the target nucleic acid as the result of a single nucleotide substitution having been caused, or the detection of the absence of nucleotide which is normally found but has been substituted with another nucleotide in cases of a single nucleotide substitution having been caused.

A method for processing a nucleotide sequence (also referred to as a nucleotide sequence processing method) according to the present invention comprises, based on the above-mentioned method for designing an RNA-containing probe for detecting a target nucleic acid, the step (S1) of first obtaining nucleotide sequence information of the target nucleic acid, the step (S2) of checking the obtained nucleotide sequence information, and the step (S3) of designing an RNA-containing probe (FIG. 1). The step (S3) of designing such a probe comprises the step of sequentially processing the above-mentioned conditions (a) to (d). Further, the step of processing the above-mentioned conditions (e) and (f) is preferably included.

As will be described in more detail, the step of designing an RNA-containing probe consists of:

a step of making a determination of a nucleotide, wherein the determination is made, based on the nucleotide sequence information, as to whether or not a nucleotide selected from one nucleotide in the nucleotide sequence information, the nucleotide adjacent to the 3' side of the one nucleotide, the nucleotide in the complementary strand corresponding to the one nucleotide in the nucleotide sequence information, and the nucleotide adjacent to the 3' side of the nucleotide in the complementary strand is a purine nucleotide;

a step of generating nucleotide information, wherein one of the purine nucleotides is set as an RNA and the others are set as DNAs;

a step of generating partial nucleotide sequences, wherein the number of nucleotides in nucleotide sequences derived from the target nucleic acid to be detected or the complementary strand thereof is set to 7 to 14, thereby generating information about the partial nucleotide sequences;

a step of selecting nucleotide sequences, wherein based on the information about the partial nucleotide sequences, nucleotide sequences in which the RNA nucleotide is located at a position between 3 and 5 nucleotides from the 3' or 5' end are selected;

a step of selecting specified-nucleotide-containing sequences, wherein sequences containing a specified nucleotide are selected, wherein the Tm value of the nucleotide sequences obtained by the nucleotide sequence selecting step is in the range of 25 to 40° C.

The step of obtaining nucleotide sequence information of the target nucleic acid may include an additional step of obtaining more detail information from open public databases, based on the obtained nucleotide sequence information. Also, the step of checking the obtained nucleotide sequence information may include an additional step of comparing and checking the obtained nucleotide sequence information with the information obtained from open public databases.

Figure 2:
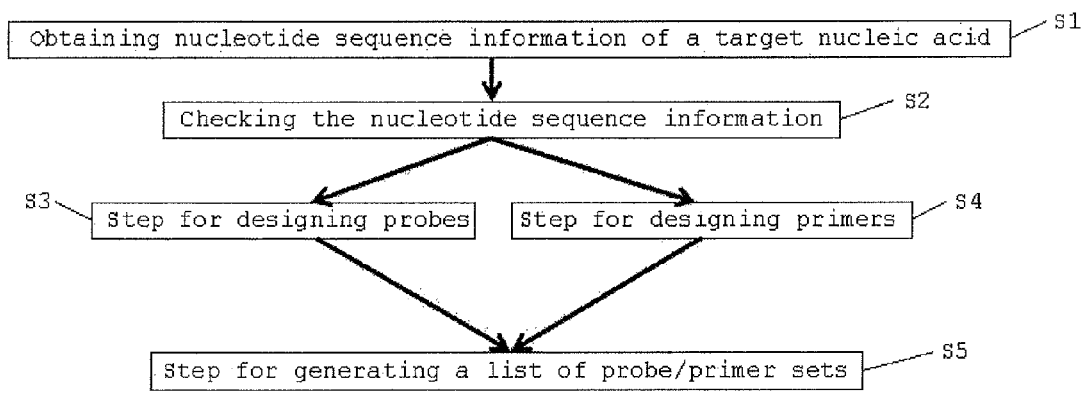
FIG. 2 represents a flow diagram showing an example of the steps of a method for processing a nucleotide sequence according to the present invention.
Figure 3:
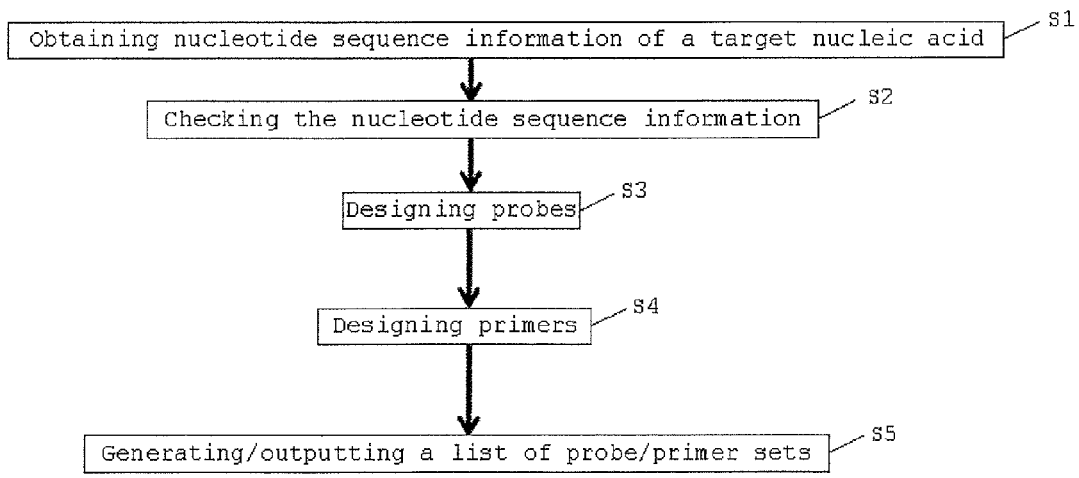
FIG. 3 represents a flow diagram showing an example of the steps of a method for processing a nucleotide sequence according to the present invention.

In addition, the step (S4) of designing a pair of primers capable of amplifying a region in the target nucleic acid to which the RNA-containing probe designed by the present invention hybridizes (FIG. 2 or 3) can be added. Further, the step (S5) of making a list of sets of the RNA-containing probes provided in the above-mentioned step and the pairs of primers designed for the respective probes can be also added. A method for designing a primer pair in the step of designing such a pair of primers is not limited in particular, and known methods may be used to design such a pair of primers that a region to which the RNA-containing probe sequence in the target nucleic acid hybridizes can be amplified. Such a pair of primers may be any one which can be used in known methods for amplification of nucleic acids, such as PCR, ICAN, and LAMP methods. The amplification of a DNA fragment derived from the target nucleic acid in a sample using the primers thus designed and the inventive method for detecting the target nucleic acid can be combined so that the presence or absence of a specified nucleotide or single nucleotide substitution in a gene of interest can be detected with a high sensitivity in a small amount of samples.

In the present invention, an RNA-containing probe can be also designed in a DNA sequence which is amplified with a pair of primers that have been already designed which are usable in known method for amplification of nucleic acids. In this case, one nucleotide in the DNA sequence which is amplified can be set as the "one nucleotide" in the present invention, thereby to design an RNA-containing probe by the method according to the present invention, so that the probe can be used to detect the amplified sequence with high sensitivity.

Programs allowing a computer to execute the nucleotide sequence processing method according to the present invention may be any ones which are capable of carrying out the steps of the nucleotide sequence processing method as described above, and include ones written, for example, in Ruby, Perl, Python, C, C++, Java®, and the like.

Computer-readable recording media having the program recorded thereon include, but are not limited to, for example, optical discs such as compact discs (CDs), digital versatile discs (DVDs), Blue-ray discs (BDs), and the like, flash memories, hard discs, and, others. Any media which are readable by a computer can be used.

The device for processing a nucleotide sequence (also referred to as a nucleotide sequence processing device) according to the present invention comprises, based on the above-mentioned method for designing an RNA-containing probe for detecting a target nucleic acid, means for first obtaining nucleotide sequence information of a target nucleic acid to be detected, means for checking the obtained nucleotide sequence information, and means for designing an RNA-containing probe. The means for designing such a probe comprises means for sequentially processing the above-mentioned conditions (a) to (d). Further, means for processing the above-mentioned conditions (e) and (f) is preferably included.

As will be described in more detail the means for designing an RNA-containing probe consists of:

means for making a determination of a nucleotide, wherein the determination is made, based on the nucleotide sequence information, as to whether or not at least one of one nucleotide in the nucleotide sequence of the target nucleic acid, the nucleotide adjacent to the 3' side of the one nucleotide, the nucleotide in the nucleotide sequence of the complementary strand of the target nucleic acid corresponding to the one nucleotide, and the nucleotide adjacent to the 3' side of the nucleotide in the nucleotide sequence of the complementary strand is a purine nucleotide;

means for generating nucleotide information, wherein one of the purine nucleotides is set as an RNA and the others are set as DNAs;

means for generating partial nucleotide sequences, wherein the number of nucleotides in nucleotide sequences derived from the target nucleic acid to be detected or the complementary strand thereof is set to 7 to 14, thereby generating information about the partial nucleotide sequences;

means for selecting nucleotide sequences, wherein the nucleotide sequences in which the RNA nucleotide is located at a position between 3 and 5 nucleotides from the 3' or 5' end are selected based on the information about the partial nucleotide sequences;

means of selecting specified-nucleotide-containing sequences, wherein sequences containing a specified nucleotide are selected, wherein the Tm value of the nucleotide sequences obtained by the nucleotide sequence selecting step is in the range of 25 to 40° C.

The means for obtaining nucleotide sequence information of the target nucleic acid may include an additional means for obtaining more detail information from open public databases, based on the obtained nucleotide sequence information. Also, the means for checking the obtained nucleotide sequence information may include an additional means for comparing and checking the obtained nucleotide sequence information with the information obtained from open public databases. In addition, the above-mentioned means may include an additional means for evaluating the possibility of hybridization of the designed RNA-containing probe to non-target nucleic acids.

In addition, means for designing a pair of primers capable of amplifying a region in the target nucleic acid to which the RNA-containing probe designed by the present invention hybridizes can be added. Further, means for making a list of sets of the RNA-containing probes provided in the above-mentioned means and the pairs of primers designed for the respective probes can be also added. Here, such primers may be any one which can be used in known methods for amplification of nucleic acids, such as PCR, ICAN, and LAMP methods. The amplification of a DNA fragment derived from the target nucleic acid in a sample using the primers thus designed and the inventive method for detecting the target nucleic acid can be combined so that the presence or absence of a specified nucleotide or single nucleotide substitution in a gene of interest can be detected with a high sensitivity in a small amount of samples.

The device for processing a nucleotide sequence according to the present invention may be a device which performs the entire processing in a independent manner, or a system for processing a nucleotide sequence, wherein information is communicated between the nucleotide sequence processing device and a client device which is connected to the nucleotide sequence processing device in a state capable of communication therewith via a network. In the former, for example, a program according to the present invention can be recorded or installed on the hard disc of a computer in a state capable of executing the program, thereby to use the computer as the nucleotide sequence processing device according to the present invention. Also, a program according to the present invention can be recorded or installed on an external medium, such as an optical disc or a flash memory, in a state capable of executing the program, and the external medium can be connected to a computer, thereby to configure a device which can perform the nucleotide sequence processing according to the present invention, without recording or installing the program on the hard disc of the computer. In the latter, for example, the nucleotide sequence information of target nucleic acid can be transmitted through the client device to the nucleotide sequence processing device according to the present invention and the information about RNA-containing probes for detecting the target nucleic acid and the information for designing primer pairs, which are obtained by the nucleotide sequence processing device, can be received through the client device via a PC communication or via a network such as an intranet or internet. Alternatively, these pieces of information can be selected and received, according to a request by the client device. This system would allow one to use the nucleotide sequence processing device according to the present invention, regardless of where the device is located or the like, and thus could be useful. In addition, it is obvious that in order to make the nucleotide sequence processing device readily available through the client device, the system is configured such that information can be transmitted and received through a Web screen.

An RNA-containing probe designed according to the present invention and ribonuclease H can be added to reaction solutions for amplification of a nucleic acid, making it possible to perform the amplification and detection of a target nucleic acid in a single reaction. An RNA-containing probe designed according to the present invention is suitable particularly for a detection system in which the reaction for amplifying a fragment of a target nucleic acid by PCR and the reaction for cleaving the probe with a thermostable ribonuclease H are carried out at the same time. An RNA-containing probe labeled such that a signal, for example, fluorescence, is generated with the cleavage of the probe as described above is suitable in this aspect, and can be used to construct a system for rapid detection of a target nucleic acid or single nucleotide substitution in combination with a nucleic acid amplification device equipped with a signal detection system.

According to the present invention, an RNA-containing probe can be produced which is useful in detecting a target nucleic acid or an SNP in the target nucleic acid, and there is also provided a pair of primers for amplifying a fragment of the target nucleic acid which can be combined with the probe. An RNA-containing probe and primers as described above can be components of reagents or kits for detecting a target nucleic acid or SNP with good sensitivity. Therefore, according to the present invention, there is also provided a sensitive system for detection of a target nucleic acid or single nucleotide substitution.

Specific embodiments of the present invention will be described based on FIGS. 19 to 32.

Figure 19:
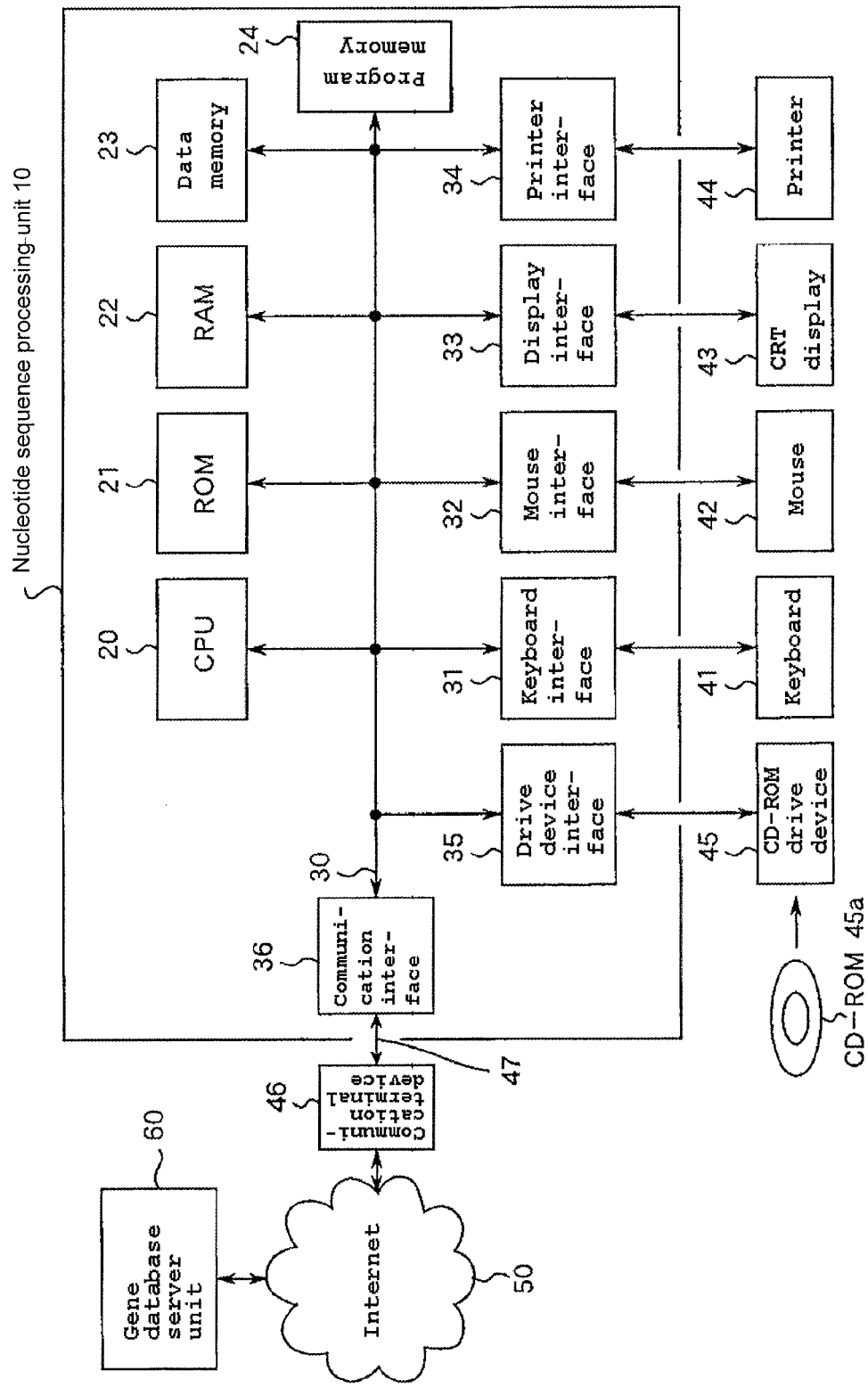
FIG. 19 represents an example of a block diagram of a device according to the present invention.
Figure 20:
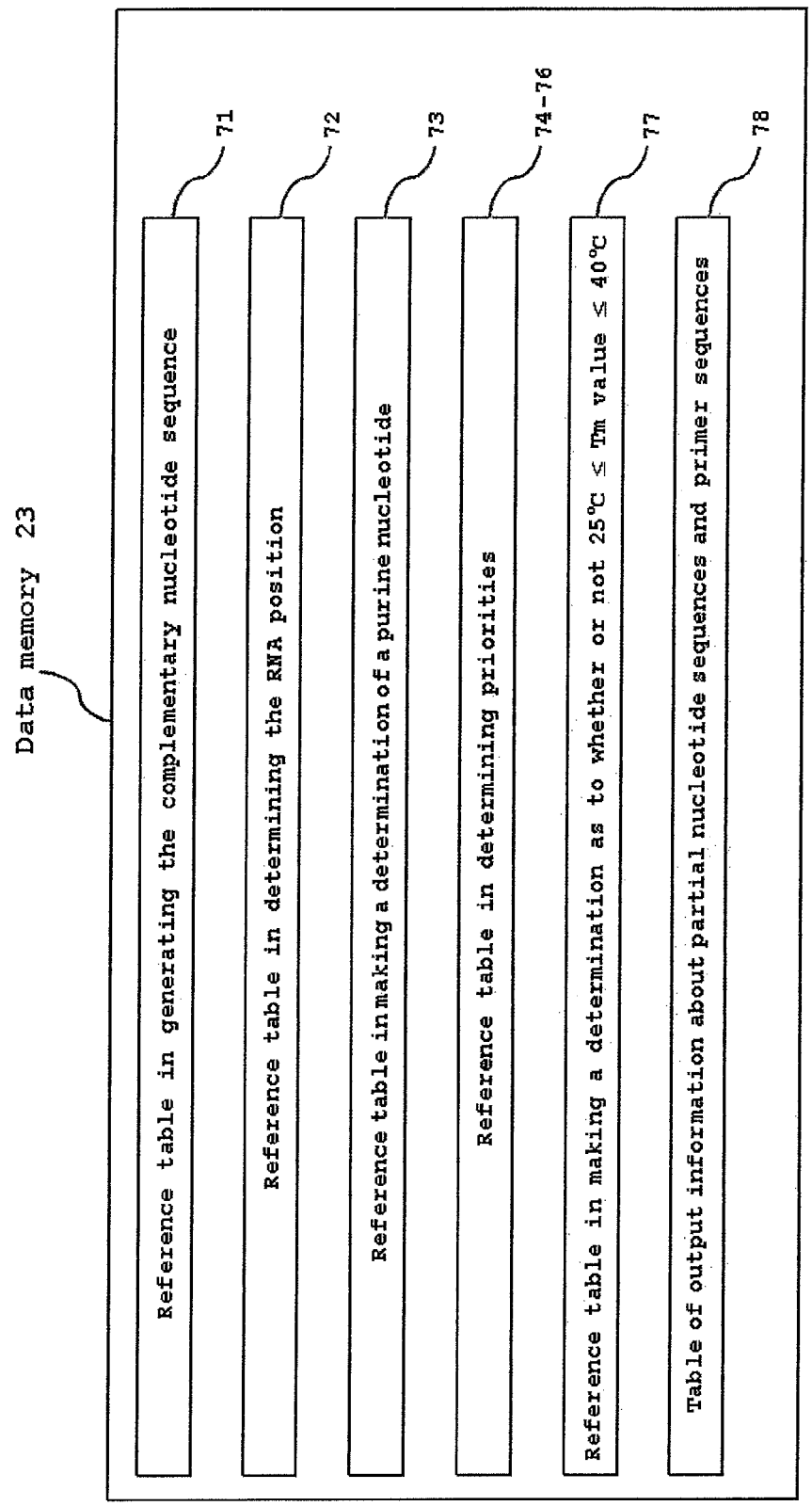
FIG. 20 is a representation showing the internal structure of data memory 23.

FIG. 19 represents device 10 for processing a nucleotide sequence according to the present invention. Nucleotide sequence processing Device 10 comprises:

(a) CPU (central processing unit) 20 of a computer for calculating and controlling the operation and processing of the nucleotide sequence processing device 10;

(b) ROM (read-only memory) 21 for storing basic computer programs, such as operation program, and data necessary for running the programs;

(c) RAM (random-access memory) 22 for serving as a working memory of CPU 20 and temporarily storing parameters and data necessary in image processing;

(d) data memory 23 configured, for example, as a hard disc memory and for storing data of various kinds shown in FIG. 20;

(e) program memory 24 configured, for example, as a hard disc memory and for storing programs for the processes shown in FIGS. 21 to 25 which are read in with CD-ROM drive device 45;

(f) communication interface 36 connected to communication terminal device 46 and for allowing gene database data to be transmitted to and received from gene database server unit 60 via internet 50;

(g) keyboard interface 31 connected to keyboard 41 with which given data and instruction commands are entered and for receiving the data and instruction commands entered through keyboard 41, performing interface processing, such as a prescribed signal conversion, and transferring them to CPU 20;

(h) mouse interface 32 connected to mouse 42 with which instruction commands are entered on CRT display 43 and for receiving the data and instruction commands entered through mouse 42, performing interface processing, such as a prescribed signal conversion, and transferring them to CPU 20;

(i) display interface 33 connected to CRT display 43 displaying an output data processed by CPU 20, setting and instructing screens, and others and for converting an image data to be displayed to image signals for CRT display 43 and outputting and displaying the image signals on CRT display 43;

(j) printer interface 34 connected to printer 44 with which output data processed by CPU 20 and others are printed and for performing a prescribed signal conversion of a printing data to be printed or the like and outputting the data to printer 44 for printing it; and (k) drive device interface 35 connected to CD-ROM drive device 45 reading out the program data of the programs for the above-mentioned processes from CD-ROM 45a having the programs recorded thereon and for performing a prescribed signal conversion and transferring the program data of the read-out image-processing program or the like to program memory 24; wherein these circuits 20 to 24 and 31 to 36 are connected via bus 30.

FIG. 20 represents a block diagram showing the internal structure of data memory 23 shown in FIG. 19. As shown in FIG. 20, data memory 23 stores the following tables:

(1) Reference Table 71 used in generating the complementary nucleotide sequence;

(2) Reference Table 72 used in determining the RNA position;

(3) Reference Table 73 used in making a determination of a purine nucleotide;

(4) Reference Tables 74 to 76 used in determining priorities;

(5) Reference Table 77 used in making a'determination as to whether or not 25° C.≤Tm value≤40° C.; and (6) Table 78 of output information about partial nucleotide sequences and primer sequences.

Tables 71 to 78 are shown in FIGS. 27 to 32.

Figure 21:
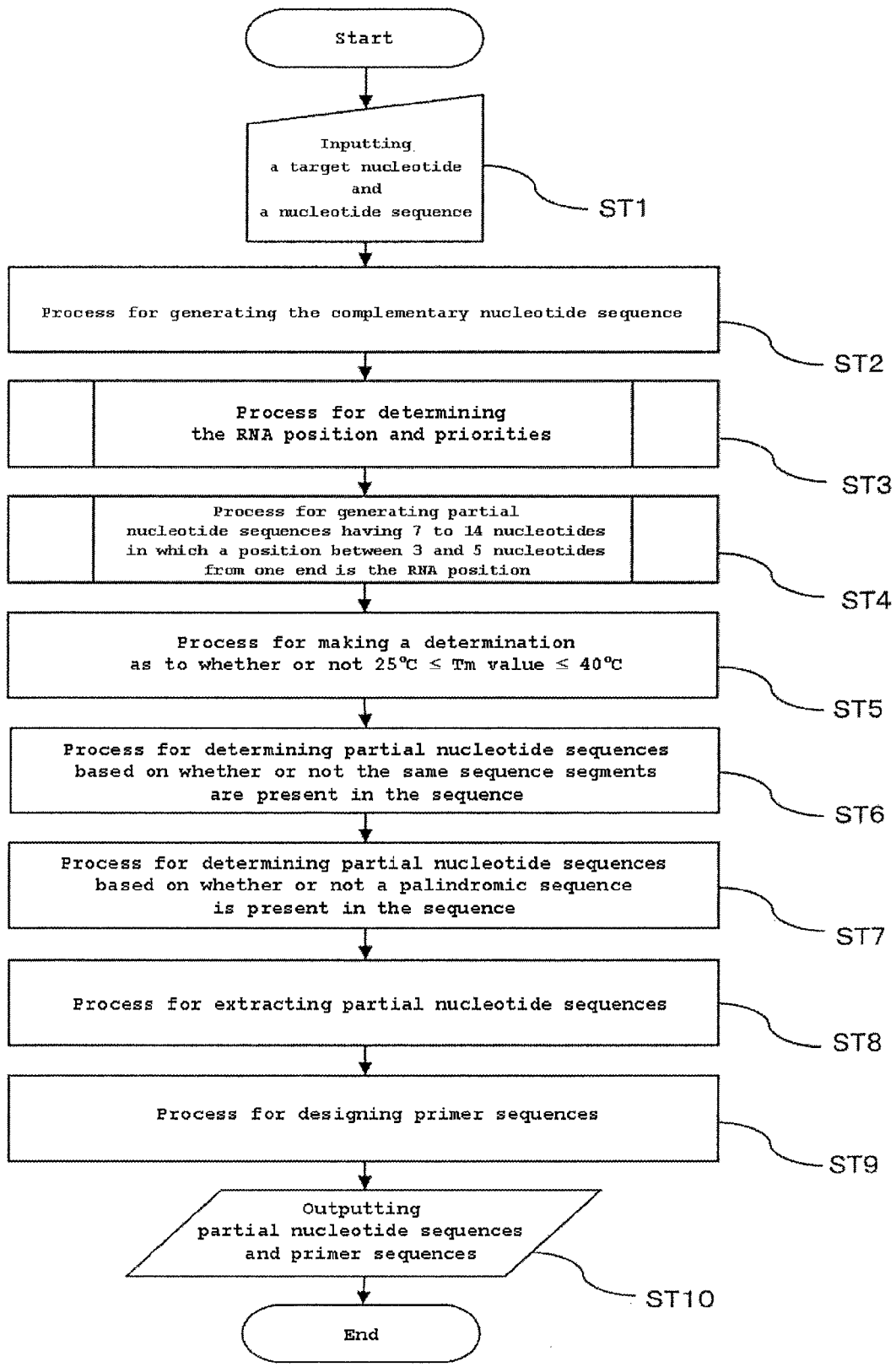
FIG. 21 represents an example of the flow chart of a method for processing a nucleotide sequence according to the present invention.

The device shown in FIG. 19 performs the process steps indicated in the flow chart shown in FIG. 21. ST1 in FIG. 21 is a process step of entering the nucleotide sequence of a target nucleic acid and information describing a target nucleotide. The string to be entered is string K (number x, string J, symbol i) (See Table 70 shown in FIG. 26). String J is a one-dimensional string composed of any letters of A, T, G, or C. String J corresponds to the nucleotide sequence of the target nucleic acid. The left side of string J represents the 5' side of the nucleotide sequence and the right side represents the 3' side of the nucleotide sequence. Number x is a natural number. Number x represents the target nucleotide. The letter which is located at the x-th position from the left end of string J represents the target nucleotide. Symbol i indicates that string K is a nucleotide sequence which has been inputted. Symbol i is for distinguishing the nucleotide sequence represented by string K from a nucleotide sequence generated in ST2.

ST2 is a process step of generating the complementary nucleotide sequence of the target nucleic acid. ST2 generates string M (number x, string L, symbol (see Table 70 shown in FIG. 26). Number x is identical with the number x in string K. String L is generated from string J, based on. Table 71 in FIG. 27. Each of the letters making up string L has the relationship of correspondence indicated in Table 71 in FIG. 27 with each of the letters which make up the string obtained by reading string J from right to right and rearranging the read string J from left to right. Symbol c indicates that string L is the complementary nucleotide sequence.

Figure 22:
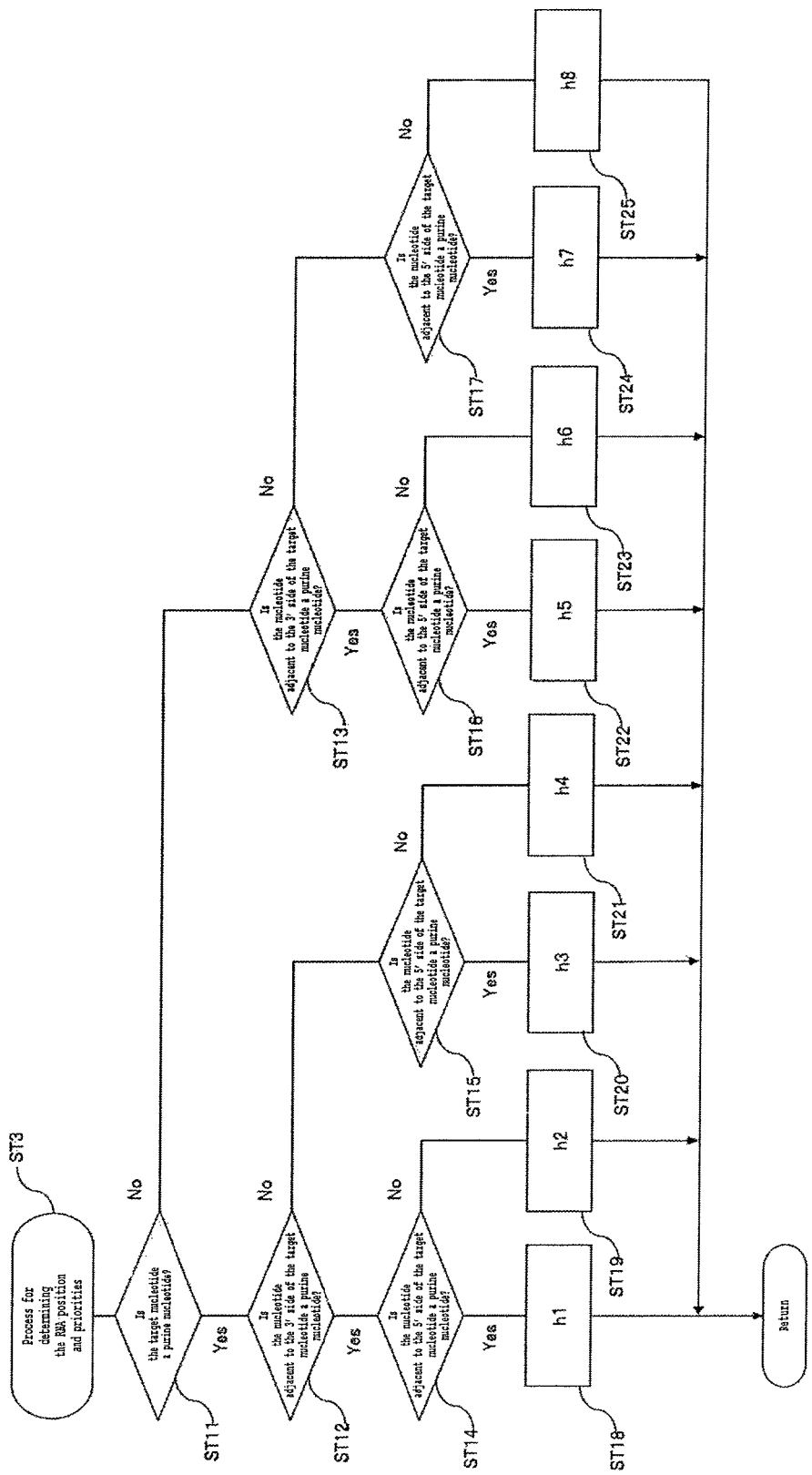
FIG. 22 represents a flow chart of ST3.

ST3 is a process step of determining the RNA position and the order of priority. ST3 is performed in accordance with the flow chart shown in FIG. 22. The flow chart shown in FIG. 22 is composed of process steps ST11 to ST17 for making a determination and ST18 to ST25 for generating information.

Process steps ST11 to ST17 for making a determination are performed according to Table 73 in FIG. 29. In ST11, a determination of Yes is made when the letter at the x-th position from the left side of string J is A or G. When the letter at the same position in string J is T or C, on the other hand, a determination of No is made. In ST12 and ST13, a similar determination is made for the letter at the (x+1)-th position from the left side of string J. In ST14 to ST17, a similar determination is made for the letter at the (x−1)-th position from the left side of string J.

Process steps ST18 to ST25 are performed, depending on the result of determination in ST11 to ST17. In process steps ST18 to ST25, string N consisting of three letters (symbol i or c, number y, symbol z) is generated (see Table 70 shown in FIG. 26). Specifically, string N indicated in Table 72 in FIG. 28 is generated, depending on processing h1 to h8 in ST18 to ST25, respectively.

Symbol i or c, which is the first letter from the left in string N, is a symbol indicating the nucleotide sequence in which the RNA position is located. Symbol i indicates that the RNA position is located in the nucleotide sequence which has been entered in ST1. Symbol c indicates that the RNA position is located in the nucleotide sequence which has been generated in ST2.

Number y, which is the second letter from the left in string N, is number x or (x+1) and is a number for identifying the RNA position. Number y indicates that the y-th position from the left end is the RNA position.

Symbol z, which is the third letter from the left in string N, is selected from the group consisting of $\alpha$, $\beta$, and $\gamma$. Symbol z is a letter for indicating the order of priority. The letter $\alpha$ indicates the highest order of priority, followed by $\beta$ and $\gamma$ in a descending order. The string N generated is stored temporarily in data memory 23.

ST4 is a process step of generating information describing partial nucleotide sequences having 7 to 14 nucleotides in which a position between 3 to 5 nucleotides from the end is the RNA position. The processing is carried out in accordance with the flow chart shown in FIG. 23.

Figure 23:
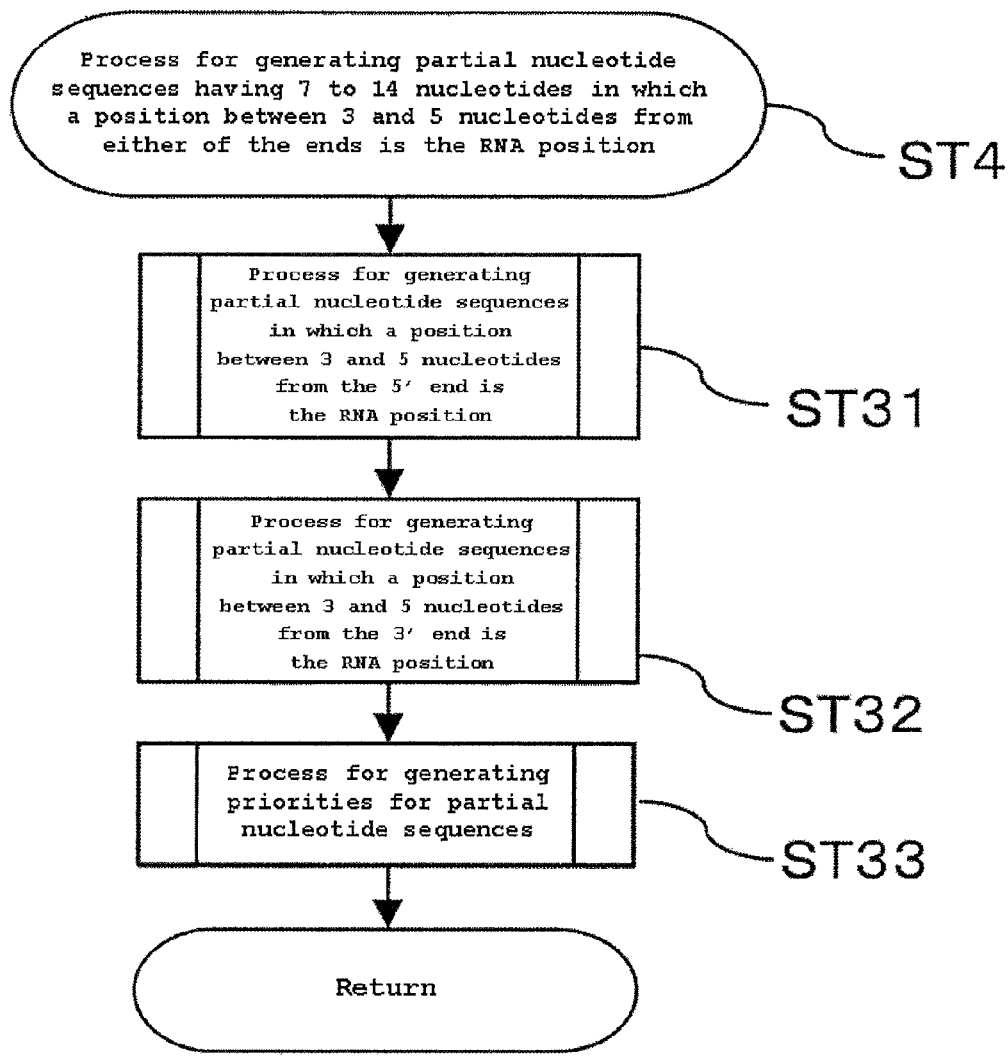
FIG. 23 represents a flow chart of ST4.

The flow chart shown in FIG. 23 consists of process Steps ST31, ST32, and ST33.

Process step ST31 is a process step of generating information describing partial nucleotide sequences in which a position between 3 to 5 nucleotides from the 5' end is the RNA position. Process step ST31 is performed in accordance with the flow chart shown in FIG. 24.

Figure 24:
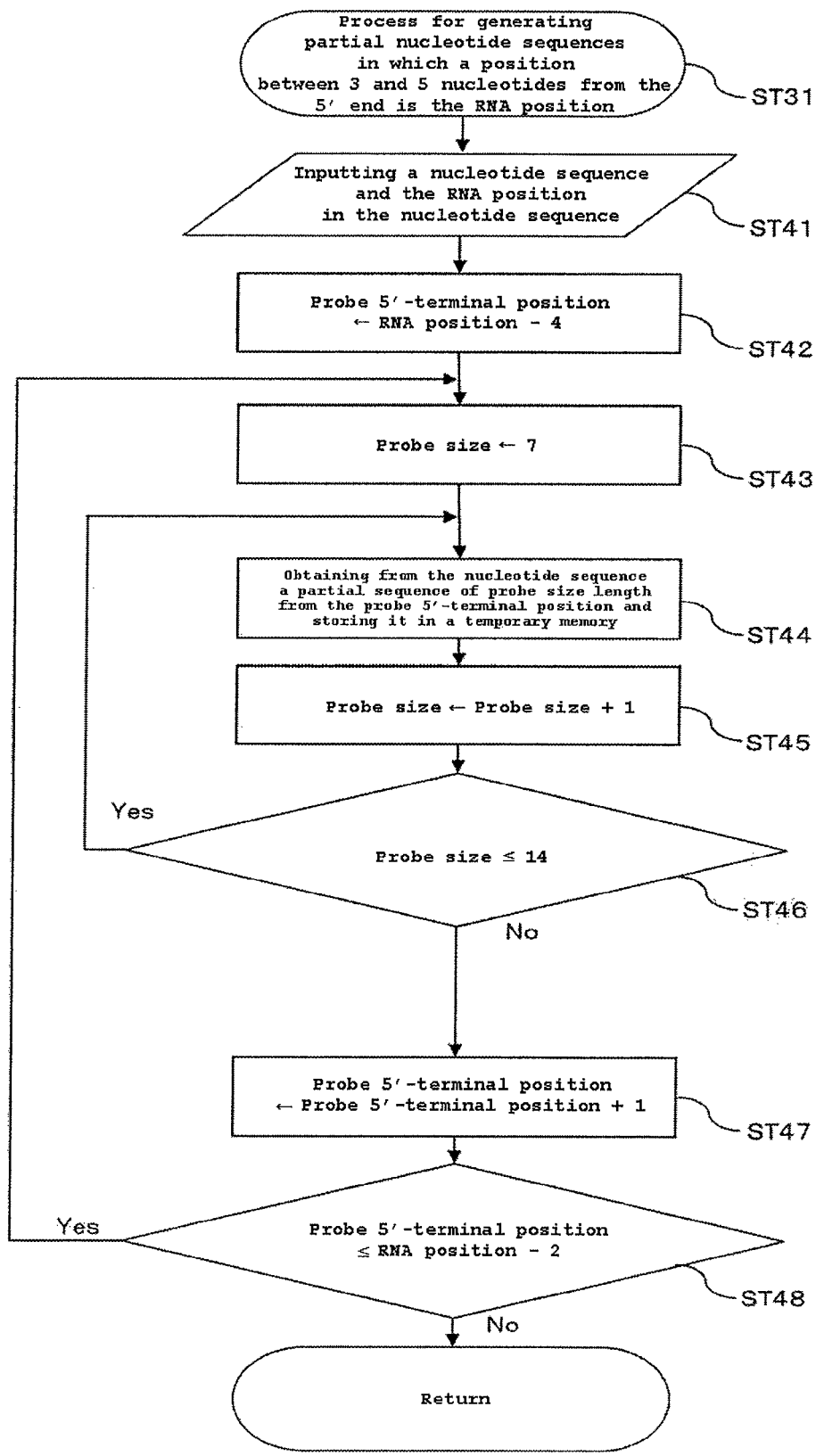
FIG. 24 represents a flow chart of ST31.

ST41 in the flow chart shown in FIG. 24 is a process step of reading out string K, string M, and string N.

In ST42, ST43, ST45, ST46, ST47, and ST48, the probe 5'-terminal position, probe size, and RNA position each are natural numbers. The RNA position is represented by number y in string N. The probe 5'-terminal position is defined as number a, the probe size as number b.

ST44 is a process step of generating string P (string O, number y, symbol z, symbol ST31). In the process of generating in ST44, reference is first made to the first letter from the left in string N from which the number y referred to in ST42 is derived. When the first letter is symbol i, letters are read out which range from the a-th letter to the (a+b−1)-th letter from the left end in string J. A string generated by rearranging the string of the read-out letters from left to right is string O. When the first letter from the left in string N is symbol c, the processing is carried out in a similar way, except that string L is used instead of string J. Number y and symbol z in string P are identical with the number y and symbol z in string N to which reference has been made. Symbol ST31 in string P is for the purpose of a process step of generating the order of priority in ST33 which is carried out later. The string P generated is stored temporarily in data memory 23.

Process step ST32 in the flow chart shown in FIG. 23 is a process step of generating information describing partial nucleotide sequences in which a position between 3 to 5 nucleotides from the 3' end is the RNA position. Process step ST32 is performed in accordance with the flow chart shown in FIG. 25. The flow chart shown in FIG. 25 is similar to that shown in FIG. 24, except that the number representing the probe 3'-terminal position is used.

Figure 25:
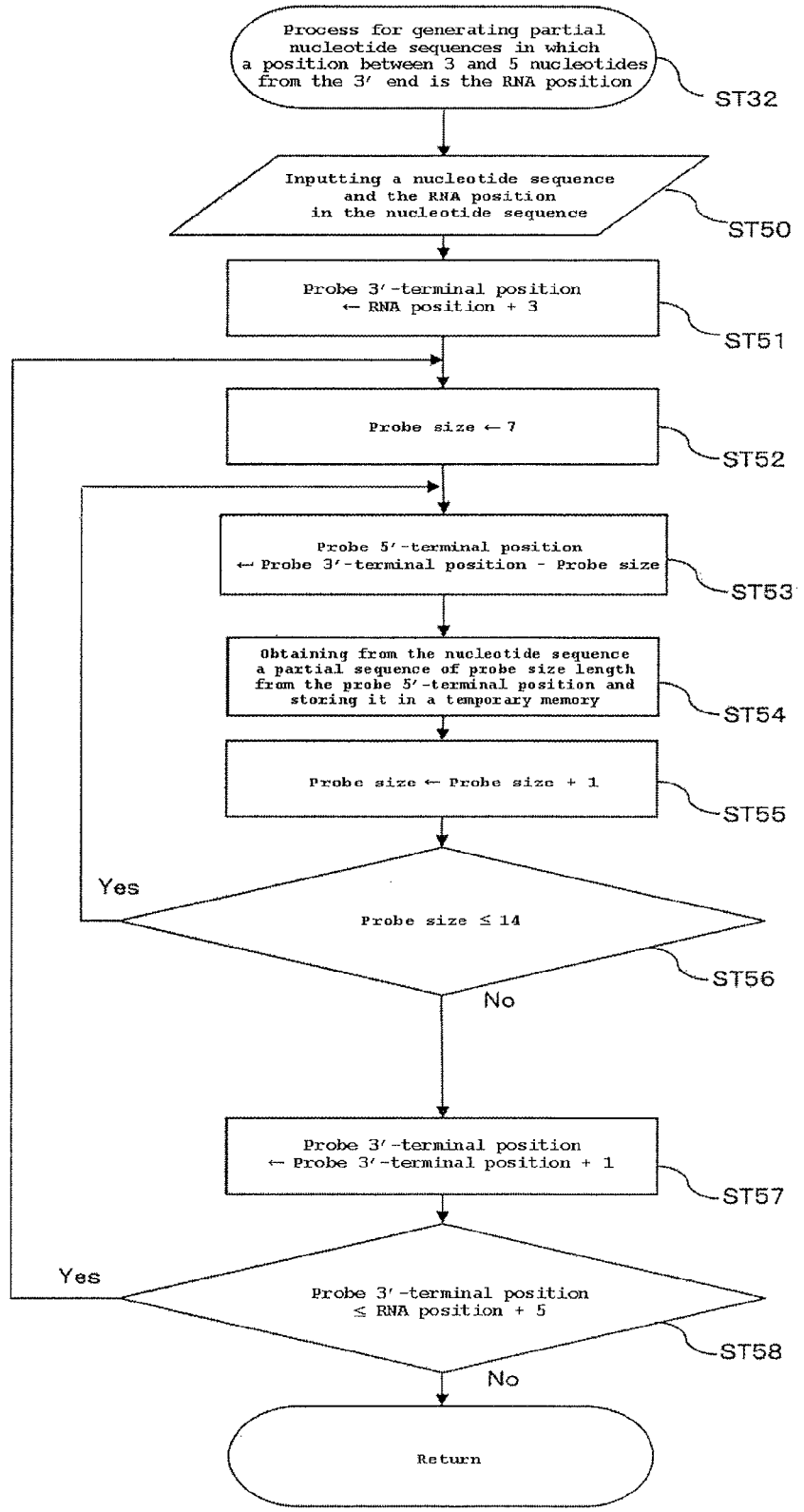
FIG. 25 represents a flow chart of ST32.

ST50 in the flow chart shown in FIG. 25 is a process step of reading out string K, string M, and string N. In ST51, ST52, ST53, ST54, ST55, ST56, ST57 and ST58, the probe 3'-terminal position, probe size, and RNA position each are natural numbers. The RNA position is represented by number y in string N. The probe 5'-terminal position is defined as number a.

ST54 is a process step of generating string Q (string O, number y, symbol z, symbol ST32). In the process of generating in ST54, reference is first made to the first letter from the left in string N from which the number y referred to in ST53 is derived. When the first letter is symbol i, letters are read out which range from the a-th letter to the (a+b−1)-th letter from the left end in string J. A string generated by rearranging the string of the read-out letters from left to right is string O. When the first letter from the left in string N is symbol c, the processing is carried out in a similar way, except that string L is used instead of string J. Number y and symbol z in string Q are identical with the number y and symbol z in string N to which reference has been made. Process step ST32 generates string Q (string O, number y, symbol z, symbol ST32) in a similar way to process step ST31 (see Table 70 shown in FIG. 26). Symbol ST32 in string Q is for generating information about the order of priority in ST33 which is carried out later. The string Q generated is stored temporarily in data memory 23.

Process step ST33 in the flow chart shown in FIG. 23 is a process step of generating information about the order of priority for partial nucleotide sequences. First, by ST31 and ST32 are read out string P (string O, number y, symbol z, symbol ST31) and string Q (string O, number y, symbol z, symbol ST32) which are being temporarily stored in data memory 23. Based on symbol z and symbol. ST31 or symbol ST32 in string P and string Q which have been read out, symbol r is determined in accordance with Tables 74 to 76 in FIG. 30. Therefore, any number of the numbers 1 to 6 indicated in Tables 74 to 76 in FIG. 30 is generated as symbol r, based on whether symbol z is any of $\alpha$, $\beta$, or $\gamma$, and whether the symbol is ST31 or ST32. Symbol r is a symbol indicating the order of priority for the partial nucleotide sequences which have been generated. Symbol r is any one of the natural numbers 1 to 6. Here, 1 means to be highest in the order of priority, followed by 2, 3, 4, 5, and 6 in a descending order of priority. Symbol r and the read-out string P and string Q are used to generate string R (string O, number y, symbol r) (see Table 70 shown in FIG. 26). The generated string R is stored temporarily in data memory 23.

ST5 is a process step of making a determination based on the Tm value. For all strings Rs which are being stored temporarily in data memory 23, their respective Tm values are calculated. Here, the Tm values are calculated under conditions having a DNA concentration of 500 nM and a salt concentration of 50 mM, using the nearest-neighbor method and further in the method described in Biochemistry, Vol. 36, No. 34, pp. 10581-10594 (1997). Using the calculated Tm values, a determination is made based on Table 77 in FIG. 31. If a determination of NO has been made, then the corresponding string R, which is being stored temporarily in data memory 23, is deleted.

ST6 is a process step in which when the same sequences are included in a string which has been generated by ST4, string R comprising that string O is deleted from data memory 23. A string ranging from the (y−2)-th position to the y-th position from the left side in string O and a string ranging from the (y−1)-th position to the (y+1)-th position from the left side in string O are read out, and a search is made as to whether or not these read-out strings are included in string O. If these strings are included in string O, then string R comprising that string O is deleted from data memory 23.

ST7 is a process step in which when string O includes an inverted repeat nucleotide sequence (palindromic sequence) of 4 letters or more, string R comprising that string O is deleted from data memory 23. The determination of a palindromic sequence being included is made in the following way: First, the sequence of a probe is defined as seq and the strand length of the probe as n. The nucleotide is numbered, from the 5' end to the 3' end, as 0, 1, 2, ..., (n−1). Under these definitions, a method as described below is performed. Accordingly, the start position i of a partial sequence is changed from the 0th position to the {(n−1)−(minimum target size×2−1)}-th position, thereby generating the respective complementary sequences of partial sequences in which the size of the partial sequences ranges from 4 bp, which is the minimum target size, to (n−i)/2, which is rounded off to the nearest whole number. If a complementary sequence generated is identical, with the sequence ranging from the partial sequence start position i to the (i+partial sequence size)-th position, then the determination of being palindromic is made. The following is an example expressing this method as a program.

```
MIN_SIZE = 4
n = seq.size
0.upto((n−1) − MIN_SIZE*2−1) do |i|
    MIN_SIZE.upto(((n−i)/2).floor) do |len|
        nucleotides = seq[i, len].reverse_complement
        result_pos = seq.index(nucleotides, i+len)
        if result_pos == (i+len)
            # palindrome
        End
    end
end
```

If the determination of being palindromic is made by the above-mentioned determination, the string R comprising that string O is deleted from data memory 23.

ST8 is a process step of extracting partial nucleotide sequences. All strings Rs which are stored in data memory 23 without deletion through the above-mentioned processing are read out from data memory 23. Of the read-out strings Rs, one or more strings Rs having the smallest number in symbol r indicating the order of priority are extracted.

ST9 is a process step of designing primer sequences. Primers are generated which are compatible with the sequence of a probe selected in ST8. A method for designing a primer pair in the step of designing a pair of such primers is not limited in particular, and known methods may be used to design such a pair of primers that a region to which an RNA-containing probe sequence in the target nucleic acid hybridizes can be amplified.

ST10 is a process step of outputting. In process step ST10, the information in Table 78 shown in FIG. 32 is outputted on CRT display 43, based on the string R extracted in ST8. String O in which the y-th letter from the left end is enclosed in parenthesis ( ) is outputted. Here, the parenthesis ( ) indicates that the position of a letter in parenthesis ( ) represents an RNA.

Other aspects include in the present invention will be descried based on the flow chart shown in FIG. 21.

In ST1, string K may be entered using keyboard 41 or mouse 42 shown in FIG. 19. String K may be also entered by entering what is obtained from gene database server unit 60 via internet 50. Further in ST1, information describing the nucleotide sequence which is complementary to the nucleotide sequence of the target nucleic acid may be entered. Therefore, string M which is to be generated by ST2 may be entered in ST1. In this case, ST2 is omitted.

In string N which is generated in ST3, for symbol z indicating the order of priority, its being generated may be omitted. In ST4, process step ST33 shown in FIG. 23 for generating priorities may be omitted. Process steps ST6 and ST7 may be also omitted.

Process step ST9 for designing primers may be also omitted. In this case, only a probe sequence or sequences is/are outputted.

Process steps ST5 to ST7 may not be carried out in this order. The order of these process steps may be changed as needed. One er more of the process steps ST5 to ST7 may be carried out at the same time as ST4. In process steps ST5 to ST7, a method using an invalid flag may be employed, instead of deleting some of the strings Rs which have been stored in data memory 23. In this case, the extraction method in ST8 is changed to a method which has been adapted accordingly.

While process step ST9 may be carried out after process step ST8, ST9 is sometimes carried out after any of the process steps ST3 to ST7.

As has been specifically described based on the above embodiments, the nucleotide sequence processing method according to the present invention is characterized in that the method comprises a process step of generating partial nucleotide sequences having 7 to 14 nucleotides in which position between 3 to 5 nucleotides from the 3' or 5' end is the RNA position and a process step of making determination as to whether or not the Tm value of the partial nucleotide sequences is in the range of 25 to 40° C.

In a more preferable embodiment, the nucleotide sequence processing method according to the present invention comprises a process step of making determination as to whether or not a target nucleotide in a target nucleic acid, the nucleotide adjacent to the 3' side of the target nucleotide, and the nucleotide adjacent to the 5' side of the target nucleotide are purine nucleotides.

In addition, in a more preferable embodiment, the nucleotide sequence processing method according to the present invention comprises a process step of determining as the RNA position the position of a nucleotide selected from:

a target nucleotide in the nucleotide sequence of a target nucleic acid;

the nucleotide adjacent to the 3' side of the target nucleotide in the nucleotide sequence of the target nucleic acid;

the nucleotide complementary to the target nucleotide in the nucleotide sequence complementary to the nucleotide sequence of the target nucleic acid; and the nucleotide adjacent to the 3' side of the nucleotide complementary to the target nucleotide in the nucleotide sequence complementary to the nucleotide sequence of the target nucleic acid. In a still more preferable embodiment, the nucleotide sequence processing method according to the present invention is performed such that the process step of determination as the RNA position is carried out on the basis of the result of the above-mentioned determination as to whether or not the nucleotide is a purine nucleotide.

In a still more preferable embodiment, the target nucleotide in the nucleotide sequence processing method according to the present invention is a nucleotide at which a single nucleotide substitution is likely to be caused.

In preferable embodiments, the nucleotide sequence processing method according to the present invention comprises selecting according to priorities based on the RNA position. In a more preferable embodiment, the priorities based on the RNA position are applied to the following nucleotides: from higher to lower priority, a target nucleotide in the nucleotide sequence of a target nucleic acid;

the nucleotide adjacent to the 3' side of the target nucleotide in the nucleotide sequence of the target nucleic acid; and the nucleotide adjacent to the 3' side of the nucleotide complementary to the target nucleotide in the nucleotide sequence complementary to the nucleotide sequence of the target nucleic acid. In addition, in a more preferable embodiment, the priorities based on the RNA position are applied to the following nucleotides: from higher to lower priority, the nucleotide complementary to the target nucleotide in the nucleotide sequence complementary to the nucleotide sequence of the target nucleic acid;

the nucleotide adjacent to the 3' side of the target nucleotide in the nucleotide sequence of the target nucleic acid; and the nucleotide adjacent to the 3' side of the nucleotide complementary to the target nucleotide in the nucleotide sequence complementary to the nucleotide sequence of the target nucleic acid.

In preferable embodiments, the nucleotide sequence processing method according to the present invention comprises selecting according to priorities based on the relative position between each end and the RNA position. In a more preferable embodiment, the priorities based on the relative position between each end and the RNA position are applied to, from higher to lower priority, an RNA position which is between 3 and 5 nucleotides from the 3' end, and an RNA position which is between 3 and 5 nucleotides from the 5' end.

In preferable embodiments, the nucleotide sequence processing method according to the present invention comprises a process step of making a determination as to whether or not a sequence which is complementary to a nucleotide sequence comprising the RNA position is present in the nucleotide sequence. In a more preferable embodiment, a sequence which is subjected to making a determination as to presence or absence is a sequence which is complementary to a sequence ranging from the RNA position to two nucleotides on the 5' side, or a sequence which is complementary to a sequence ranging from one nucleotide on the 5' side to one nucleotide on the 3' side of the RNA position.

In preferable embodiments, the nucleotide sequence processing method according to the present invention comprises a process step of making a determination as to whether or not a palindromic sequence is present in the nucleotide sequence. In a more preferable embodiment, palindromic sequence which is to be determined has four nucleotides or more.

In preferable embodiments, the nucleotide sequence processing method according to the present invention comprises a process step of determining the nucleotide sequences of primers, based on the information about partial nucleotide sequences of the probes generated.

The nucleotide sequence processing method according to the present invention as described above may be carried out using a program and hardware for executing the present method. Here, a program for executing the present method may be one which has been recorded on a computer-readable recording medium. The nucleotide sequence processing method according to the present invention may be also carried out using a processing device for performing the nucleotide sequence processing method as described above. In preferable embodiments, the processing device according to the present invention has means for carrying out the nucleotide sequence processing method according to the present invention, and the tables to which reference is made in carrying out the nucleotide sequence processing method according to the present invention are stored in a data memory. However, the nucleotide sequence processing method according to the present invention is not limited to one using these methods, and also comprises, for example, processing a nucleotide sequence by manual operations.

The nucleotide sequence processing method according to the present invention as described above may be carried out in a system for processing a nucleotide sequence, wherein the system comprising a nucleotide sequence processing device for executing the nucleotide sequence processing method according to the present invention; and a client device connected to the nucleotide sequence processing device in a state capable of communication therewith via a network. In preferable embodiments, the client device comprises means for transmitting the nucleotide sequence information of the target nucleic acid to the nucleotide sequence processing device and means for obtaining information in the target nucleic acid about an RNA-containing probe for detecting the target nucleic acid, which is transmitted from the nucleotide sequence processing device. In a more preferable embodiment, the client device comprises means for obtaining information in the target nucleic acid about an RNA-containing probe for detecting the target nucleic acid and information about primers for amplification of the target nucleic acid, which is transmitted from the nucleotide sequence processing device In a different aspect, the present invention provides a method for determining the nucleotide sequence of an RNA-containing probe for detecting a target nucleotide, the method comprising the nucleotide sequence processing method according to the present invention.

In a different aspect, the present invention also provides a method for producing an RNA-containing probe for detecting a target nucleotide, the method comprising the nucleotide sequence processing method according to the present invention. In a more preferable embodiment, the method for producing a probe according to the present invention comprises the step of preparing a nucleic acid fragment containing RNA and DNA having the same nucleotide sequence as that determined by the nucleotide sequence processing method according to the present invention.

In a different aspect, the present invention also provides a method for detecting a target nucleotide, the method comprising the step of using an RNA-containing probe for detecting the target nucleotide, wherein the probe is produce by the production method according to the present invention. In a more preferable embodiment, the method for detecting a target nucleotide according to the present invention comprises the steps of hybridizing an RNA-containing probe for detecting the target nucleotide to nucleic acids in a sample, wherein the probe is produced by the production method according to the present invention; applying treatment with ribonuclease H to the probe; and detecting whether or not the probe has been cleaved by the ribonuclease H.

EXAMPLES

The present invention will be described more specifically below by way of Examples, but is not intended in any way to be limited only to the scope of the following Examples.

Example 1

An examination was made of differences in the specificity of reactions due to differences in the positions of one nucleotide in a target nucleic acid which was desired to be detected and an RNA nucleotide in a probe for detecting the target nucleic acid. First, as a target nucleic acid, the sequence depicted in SEQ ID NO:1 in the Sequence Listing was used as template 1. Then, as probes hybridizing to template 1, that is, probes for detecting template 1, the following probes were set and used in experiments described below:
a probe in which the 7th nucleotide from the 5' end (i.e., the 6th nucleotide from the 3' end) was an RNA (which may be referred to hereinafter as probe central; SEQ ID NO:2); a probe in which the 4th nucleotide from the 5' end (i.e., the 9th nucleotide from the 3' end) was an RNA (which may be referred to hereinafter as probe 5'-4mer; SEQ ID NO:3); a probe in which the 3rd nucleotide from the 5' end (i.e., the 10th nucleotide from the 3' end) was an RNA (which may be referred to hereinafter as probe 5'-3mer; SEQ ID NO:4); a probe in which the 4th nucleotide from the 3' end (i.e., the 9th nucleotide from the 5' end) was an RNA (which may be referred to hereinafter as probe 3'-4mer; SEQ ID NO:5); and a probe in which the 3rd nucleotide from the 3' end (i.e., the 10th nucleotide from the 5' end) was an RNA (which may be referred to hereinafter as probe 3'-3mer; SEQ ID NO:6).

(1) Examination of differences it the specificity due to differences in the position of the RNA nucleotide in the probes:

One nucleotide which was desired to be detected in template 1 was set at the 10th nucleotide from the 5' end. The nucleotide in the respective probes corresponding to this 10th nucleotide was set as an RNA. In order to examine differences in the specificity due to differences in the position of the RNA in the probes, sequences of three nucleotides mrm in the nucleotide sequences of the respective probes and sequences of three nucleotides nnn in the nucleotide sequence of template 1 as shown in Table 1 were set, and template 1 and the RNA-containing probes were all synthesized. Each of the synthesized probes was labeled with Eclipse at the 5' end and with FAM at the 3' end. For the sequences in the table, the parenthesis ( ) indicates that the nucleotide in parenthesis ( ) is an RNA.

TABLE 1

| mrm in probe | nnn in template 1 | | | |
|---|---|---|---|---|
| a(a)a | ttt | tat | tct | tgt |
| a(g)a | ttt | tat | tct | tgt |
| c(a)c | gtg | gag | gcg | ggg |
| c(g)c | gtg | gag | gcg | ggg |

Then, the reagents except the polymerase in a Cycleave PCR® Core Kit (manufactured by Takata Bio Inc.) were used to carry out cycling probe reactions with a Thermal Cycler Dice® Real Time System (manufactured by Takata Bio Inc) using 1 μM template 1, 0.3 μM each probe, and 0.004 U Tli RNase H II per reaction. Reaction conditions were 40 cycles of 55° C., 3.0 seconds; 55° C., 30 seconds. For measurement of values of fluorescence, value of fluorescence at reaction start and a maximum value of fluorescence were measured. The number of cycles was also counted when the value of fluorescence came up to maximum. The results are shown in Table 2. For the sequences in the table, the parenthesis ( ) indicates that the nucleotide in parenthesis ( ) is an RNA. The numerical values in the table are values calculated as percent fluorescence value (%), which is calculated for mismatched RNA-containing probes using the formula: [(maximum value of fluorescence–a value of fluorescence at reaction start)/the number of cycles at the maximum value of fluorescence], wherein the value of the formula is set to 100% when each of the probes perfectly matching with template 1 was used. Percent fluorescence values below zero are expressed as 0%. Further, the percent fluorescence value is expressed as "–" in cases where also in perfectly matching RNA-containing probes, changes in fluorescence were not observed and thus the calculation was not possible.

TABLE 2

| mrm in probe | nnn in template 1 | probe central | probe 5'-4mer | probe 5'-3mer | probe 3'-4mer | probe 3'-3mer |
|---|---|---|---|---|---|---|
| a(a)a | ttt | 100% | 100% | — | 100% | 100% |
|  | tat | 29% | 4% | — | 3% | 0% |
|  | tct | 5% | 5% | — | 2% | 0% |
|  | tgt | 4% | 6% | — | 2% | 0% |
| a(g)a | ttt | 0% | 0% | 6% | 5% | 2% |
|  | tat | 0% | 0% | 9% | 1% | 7% |
|  | tct | 100% | 100% | 100% | 100% | 100% |
|  | tgt | 4% | 4% | 13% | 1% | 4% |
| c(a)c | gtg | 100% | 100% | 100% | 100% | 100% |
|  | gag | 1% | 2% | 0% | 1% | 0% |
|  | gcg | 10% | 0% | 5% | 6% | 3% |
|  | ggg | 8% | 3% | 12% | 4% | 2% |
| c(g)c | gtg | 10% | 3% | 2% | 6% | 2% |
|  | gag | 1% | 0% | 0% | 1% | 0% |
|  | gcg | 100% | 100% | 100% | 100% | 100% |
|  | ggg | 5% | 2% | 2% | 4% | 2% |

As shown in Table 2, relatively high percent fluorescence values (%) were measured when the probe central was used, even in cases where the sequences nnn and mrm were not complementary, whereas only relatively low percent fluorescence values (%) were measured when the probe 5'-4mer, probe 5'-3mer, probe 3'-4mer, and probe 3'-3mer were used, in cases where the sequences nnn and mrm were not complementary. From these results, it turned out that the nucleotide of interest was able to be detected with a higher specificity and efficiency by setting the position of an RNA in the probe at the 3rd nucleotide and 4th nucleotide from the 5' end or the 3' end of the probe than at the center, the 7th nucleotide from the 5' end, or the 6th nucleotide from the 3' end of the probe.

(2) Examination of differences in the specificity due to differences among the positions of a nucleotide which was desired to be detected and an RNA in probes corresponding to the nucleotide:

Experiments described below were carried out, in order to examine the specificity in cases of where the RNA was set at positions other than the position of the nucleotide in probes corresponding to the one nucleotide that was desired to be detected in a target nucleic acid. First, one nucleotide which was desired to be detected in template 1 was set at the 11th nucleotide from the 5' end. Sequences of three nucleotides mrm in the nucleotide sequences of respective probes and sequences of three nucleotides nnn in the nucleotide sequence of template 1 as shown in Table 3 were set such that the nucleotide adjacent to the 3' end of the nucleotide in the respective probes corresponding to this 11th nucleotide was set as an RNA, and template 1 and the RNA-containing probes were all synthesized. Each of the synthesized probes was labeled with Eclipse at the 5' end and with FAM at the 3' end. For the sequences in the table, the parenthesis ( ) indicates that the nucleotide in parenthesis ( ) is an RNA.

TABLE 3

| mrm in probe | nnn in template 1 | | | |
|---|---|---|---|---|
| a(a)a | ttt | tta | ttc | ttg |
| a(g)a | tct | tca | tcc | tcg |
| c(a)c | gtt | gta | gtc | gtg |
| c(g)c | gct | gca | gcc | gcg |

Then, cycling probe reactions were performed under conditions similar to those in Example 1-(1). The results are shown in Table 4. For the sequences in the table, the nucleotide in parenthesis ( ) represents an RNA. The numerical values in the table represent percent fluorescence values calculated using a calculation method similar to that in Table 2.

TABLE 4

| mrm in probe | nnn in template 1 | probe 5'-4mer | probe 5'-3mer | probe 3'-4mer | probe 3'-3mer |
|---|---|---|---|---|---|
| a(a)a | ttt | 100% | 100% | 100% | 100% |
|  | tta | 3% | 10% | 2% | 29% |
|  | ttc | 1% | 18% | 1% | 3% |
|  | ttg | 6% | 6% | 3% | 1% |
| a(g)a | tct | 100% | 100% | 100% | 100% |
|  | tca | 0% | 0% | 0% | 0% |
|  | tcc | 1% | 0% | 1% | 1% |
|  | tcg | 0% | 1% | 0% | 0% |
| c(a)c | gtt | 1% | 4% | 1% | 0% |
|  | gta | 1% | 2% | 0% | 1% |
|  | gtc | 1% | 0% | 0% | 0% |
|  | gtg | 100% | 100% | 100% | 100% |
| c(g)c | gct | 1% | 3% | 4% | 1% |
|  | gca | 1% | 7% | 1% | 0% |
|  | gcc | 3% | 23% | 1% | 0% |
|  | gcg | 100% | 100% | 100% | 100% |

One nucleotide which was desired to be detected in template 1 was set at the 9th nucleotide from the 5' end. Sequences of three nucleotides mrm in the nucleotide sequence of respective probes and sequences of three nucleotides nnn in the nucleotide sequence of template 1 as shown in Table 5 were set such that the nucleotide adjacent to the 5' end of the nucleotide in the respective probes corresponding to this 9th nucleotide was set as an RNA, and template 1 and the RNA-containing probes were all synthesized. Each of the synthesized probes was labeled with Eclipse at the 5' end and with FAM at the 3' end. For the sequences in the table, the parenthesis ( ) indicates that the nucleotide in parenthesis ( ) is an RNA.

TABLE 5

| mrm in probe | nnn in template 1 | | | |
|---|---|---|---|---|
| a(a)a | ttt | att | ctt | gtt |
| a(g)a | tct | act | cct | gct |
| c(a)c | ttg | atg | ctg | gtg |
| c(g)c | tcg | acg | ccg | gcg |

Then, cycling probe reactions were performed under conditions similar to those in Example 1-(1). The results are shown in Table 6. For the sequences in the table, the parenthesis ( ) indicates that the nucleotide in parenthesis ( ) is an RNA. The numerical values in the table represent percent fluorescence values calculated using a calculation method similar to that in Table 2

TABLE 6

| mrm in probe | nnn in template 1 | probe 5'-4mer | probe 5'-3mer | probe 3'-4mer | probe 3'-3mer |
|---|---|---|---|---|---|
| a(a)a | ttt | 100% | 100% | 100% | 100% |
|       | att | 14%  | 9%   | 9%   | 82%  |
|       | ctt | 27%  | 18%  | 15%  | 34%  |
|       | gtt | 15%  | 10%  | 14%  | 40%  |
| a(g)a | tct | 100% | 100% | 100% | 100% |
|       | act | 1%   | 0%   | 4%   | 8%   |
|       | cct | 3%   | 1%   | 5%   | 8%   |
|       | gct | 2%   | 1%   | 5%   | 9%   |
| c(a)c | ttg | 1%   | 1%   | 8%   | 8%   |
|       | atg | 1%   | 1%   | 9%   | 12%  |
|       | ctg | 1%   | 1%   | 5%   | 8%   |
|       | gtg | 100% | 100% | 100% | 100% |
| c(g)c | tcg | 10%  | 9%   | 33%  | 29%  |
|       | acg | 3%   | 2%   | 22%  | 16%  |
|       | ccg | 0%   | 0%   | 0%   | 0%   |
|       | gcg | 100% | 100% | 100% | 100% |

From the results shown in Tables 4 and 6, it turned out that the nucleotide of interest was able to be specifically and efficiently detected also in the case where the nucleotide adjacent to the 3' end of the respective nucleotide in the probes corresponding to the one nucleotide that was desired to be detected in the target nucleic acid was set as an RNA, as in the case where the respective nucleotide in the probes corresponding to the one nucleotide that was desired to be detected was set as an RNA. In contrast, it turned out that the case where the nucleotide adjacent to the 5' side was set as an RNA resulted in reduced specificity.

Example 2

An examination was made of the specificity of reactions due to differences in the Tm values of RNA-containing probes for detecting a target nucleic acid. First, for SNPs registered in NCBI, rs5443, rs1654416, and rs1799821, each probe containing one of the SNPs and having a Tm value either of 25 to 32° C. or of 35 to 40° C. was designed. In the case of rs5443, probes were designed which were designed in the positive (sense) strand of the genome sequence and in which the nucleotides adjacent to the 3' side of the nucleotide corresponding to the SNP position in the genome sequence were set as an RNA located at the 3rd nucleotide and at the 4th nucleotides from the 5' end of the probe, and which were designed in the antisense strand of the genome sequence and in which the nucleotides corresponding to the SNP position on the complementary strand of the genome sequence were set as an RNA located at the 3rd nucleotide from the 3'-end of the probe (SEQ ID NOs:7 and 8). In the case of rs1654416, probes were designed which were designed in the antisense strand of the genome sequence and in which the nucleotides corresponding to the SNP position on the complementary strand of the genome sequence were set as an RNA located at the 3rd nucleotide from the 3' end of the probe (SEQ ID NOs:9 to 12). In the case of rs1799821, probes were designed which were designed in the sense strand of the genome sequence and in which the nucleotides corresponding to the SNP position in the genome sequence was set as an RNA located at the 3rd nucleotide from the 5' end (SEQ ID NO:13) and at the 3rd nucleotide from the 3' end of the probe (SEQ ID NOs:14 and 15). The sequences and Tm values of the designed probes and the type of fluorescent labels of the RNA-containing probes in their synthesis are shown in Table 7. For the sequences in the table, the parenthesis ( ) indicates that the nucleotide in parenthesis ( ) is an RNA.

TABLE 7

| Probe name | Length | Sequence | Tm vale | Probe labels | SEQ ID NO. |
|---|---|---|---|---|---|
| rs5443 C probe | 8mer | cc(g)tggcc | 30.4 | Eclipse-labeled at the 5' end FAM-labeled at the 3' end | Not shown in Sequence Listing because of less than 10 mer |
| rs5443 T probe | 9mer | tct(g)tggcc | 29.2 | Eclipse-labeled at the 5' end ROX-labeled at the 3' end | Not shown in Sequence Listing because of less than 10 mer |
| rs5443 C probe2 | 10mer | aggccac(g)ga | 39.0 | Eclipse-labeled at the 5' end FAM-labeled at the 3' end | No. 7 |
| rs5443 T probe2 | 11mer | aaggccac(a)ga | 36.6 | Eclipse-labeled at the 5' end ROX-labeled at the 3' end | No. 8 |
| rs1654416 C probe | 11mer | ttacaaac(g)aa | 30.9 | Eclipse-labeled at the 5' end FAM-labeled at the 3' end | No. 9 |
| rs1654416 T probe | 12mer | ttcacaaac(a)aa | 30.1 | Eclipse-labeled at the 5' end ROX-labeled at the 3' end | No. 10 |
| rs1654416 C probe2 | 13mer | attcacaaac(g)aa | 35.7 | Eclipse-labeled at the 5' end FAM-labeled at the 3' end | No. 11 |
| rs1654416 T probe2 | 14mer | cattcacaaac(a)aa | 36.3 | Eclipse-labeled at the 5' end ROX-labeled at the 3' end | No. 12 |
| rs1799821 A probe | 11mer | cc(a)tccacttt | 30.5 | Eclipse-labeled at the 5' end FAM-labeled at the 3' end | No. 13 |
| rs1799821 G probe | 9mer | actgcc(g)tc | 31.0 | Eclipse-labeled at the 5' end ROX-labeled at the 3' end | Not shown in Sequence Listing because of less than 10 mer |
| rs1799821 A probe2 | 12mer | tctactgcc(a)tc | 35.4 | Eclipse-labeled at the 5' end FAM-labeled at the 3' end | No. 14 |
| rs1799821 G probe2 | 11mer | ctactgcc(g)tc | 36.7 | Eclipse-labeled at the 5' end ROX-labeled at the 3' end | No. 15 |

For the above-mentioned RNA-containing probes, primer pairs were designed such that Cycleave PCRs were able to be carried out. For rs5443 C probe and rs5443 T probe of the RNA-containing probes designed from rs5443, a pair of primers, rs5443 F primer and rs5443 R primer (SEQ ID NOs:16 and 17), was designed. For rs5443 C probe 2 and rs5443 T probe 2, a pair of primers, rs5443 F2 primer and rs5443 R2 primer (SEQ ID NOs:18 and 19), was designed. For the RNA-containing probes designed from rs1654416, rs1654416 F primer and rs1654416 R primer (SEQ ID NOs: 20 and 21) were designed. For the RNA-containing probes designed from rs1799821, a pair of primers, rs1799821 F primer and rs1799821 R primer (SEQ ID NOs:22 and 23), was designed.

The above-mentioned RNA-containing probes and primers were each synthesized, and Cycleave PCRs were performed with a Thermal Cycler Dice® Real Time System (manufactured by Takara Bio Inc.) using a Cycleave PCR® Core Kit (Manufactured by Takara Bio Inc.) according to the instructions of the kit. A template DNA was prepared as described below and an amount corresponding to $10^5$ copies was used per reaction. First, sequences which each consisted of a primer amplification region comprising the DNA sequence of each of the probes were artificially prepared individually. Then, each of the prepared, artificially synthesized sequences was inserted in the Eco RV T-Cloning site of a plasmid vector T-Vector pMD19 (Simple) (manufactured by Takara Bio Inc.) with an usual method and the inserted vector was used as the template DNA. The reactions were carried out in the combinations of the RNA-containing probes and primer pairs listed in Table 8, and FAM and ROX signals were detected, according to the instructions of the Thermal Cycler Dice® Real Time System (manufactured by Takara Bio Inc.). In the table, reactions 1, 3, and 5 represent RNA-containing probes designed to have a Tm value in the range from 25 to 32° C., and reactions 2, 4, and 6 represent RNA-containing probes designed to have a Tm value in the range from 35 to 40° C.

TABLE 8

| Reaction | Probe used | Pair of primers used |
|---|---|---|
| 1 | rs5443 C probe | rs5443 F primer |
|  | rs5443 T probe | rs5443 R primer |
| 2 | rs5443 C probe2 | rs5443 F2 primer |
|  | rs5443 T probe2 | rs5443 R2 primer |
| 3 | rs1654416 C probe | rs1654416 F primer |
|  | rs1654416 T probe | rs1654416 R primer |
| 4 | rs1654416 C probe2 | rs1654416 F primer |
|  | rs1654416 T probe2 | rs1654416 R primer |
| 5 | rs1799821 A probe | rs1799821 F primer |
|  | rs1799821 G probe | rs1799821 R primer |
| 6 | rs1799821 A probe2 | rs1799821 F primer |
|  | rs1799821 G probe2 | rs1799821 R primer |

Figure 4:
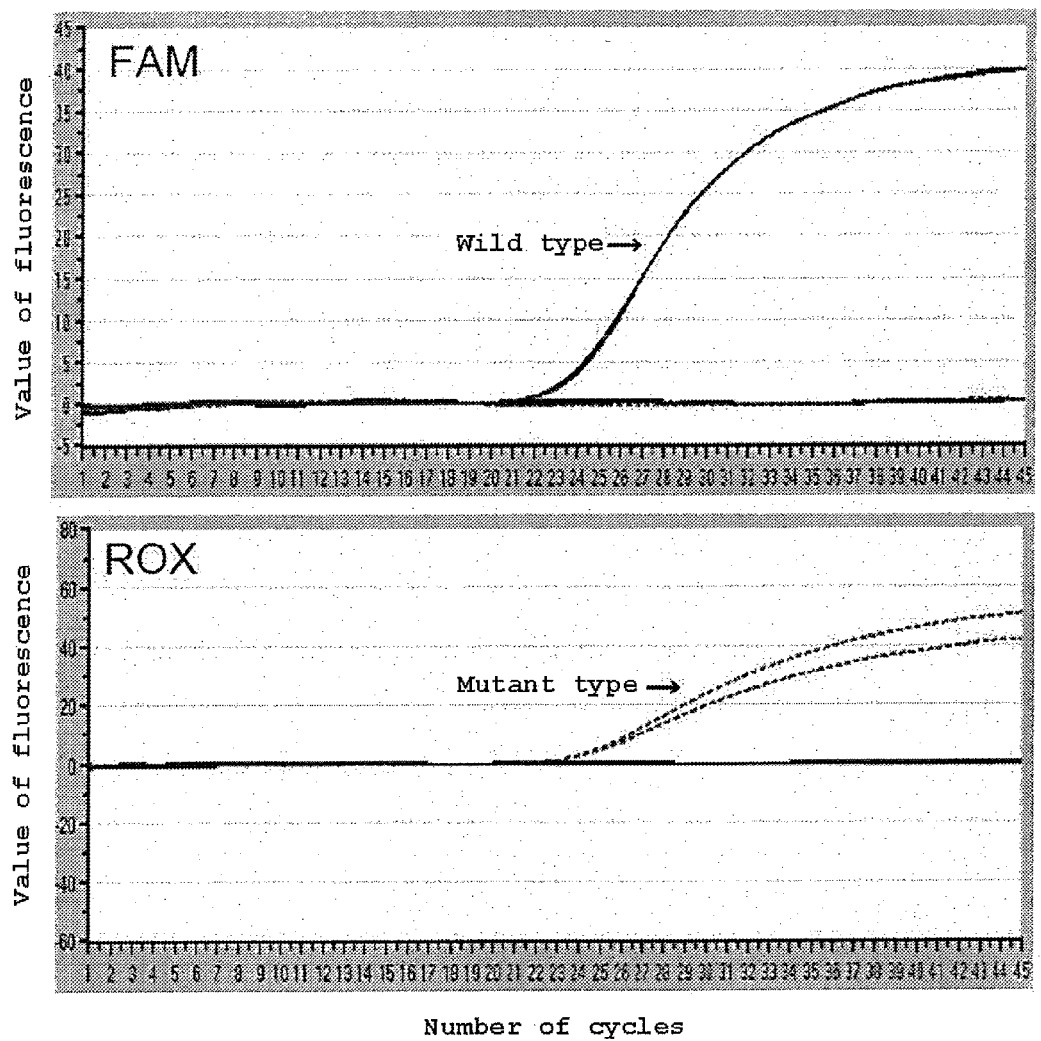
FIG. 4 represents graphs each showing an example of the results of specificity due to the Tm values of RNA-containing probes designed in the method according to the present invention.
Figure 5:
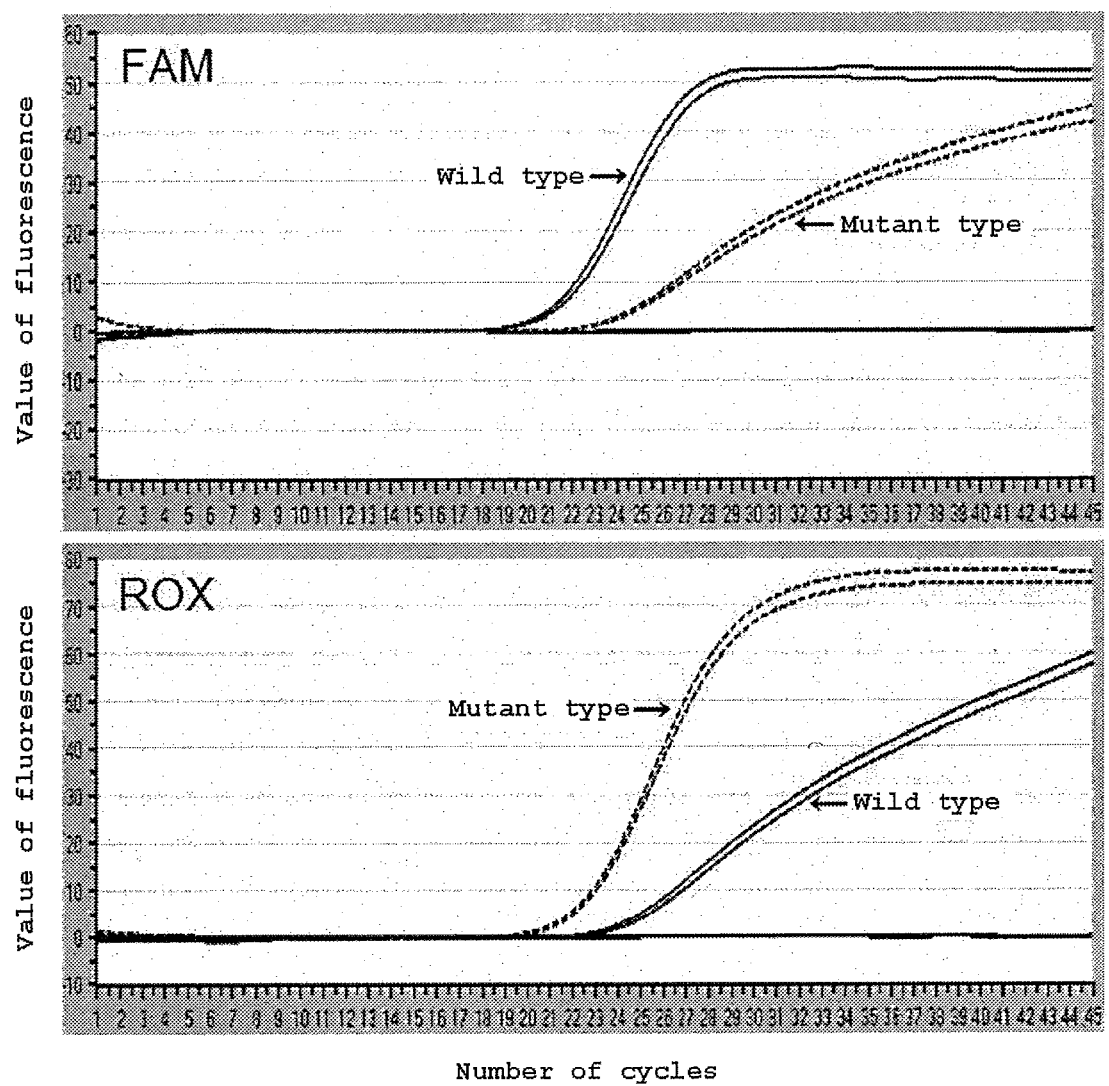
FIG. 5 represents graphs each showing an example of the results of specificity due to the Tm values of RNA-containing probes designed in the method according to the present invention.
Figure 6:
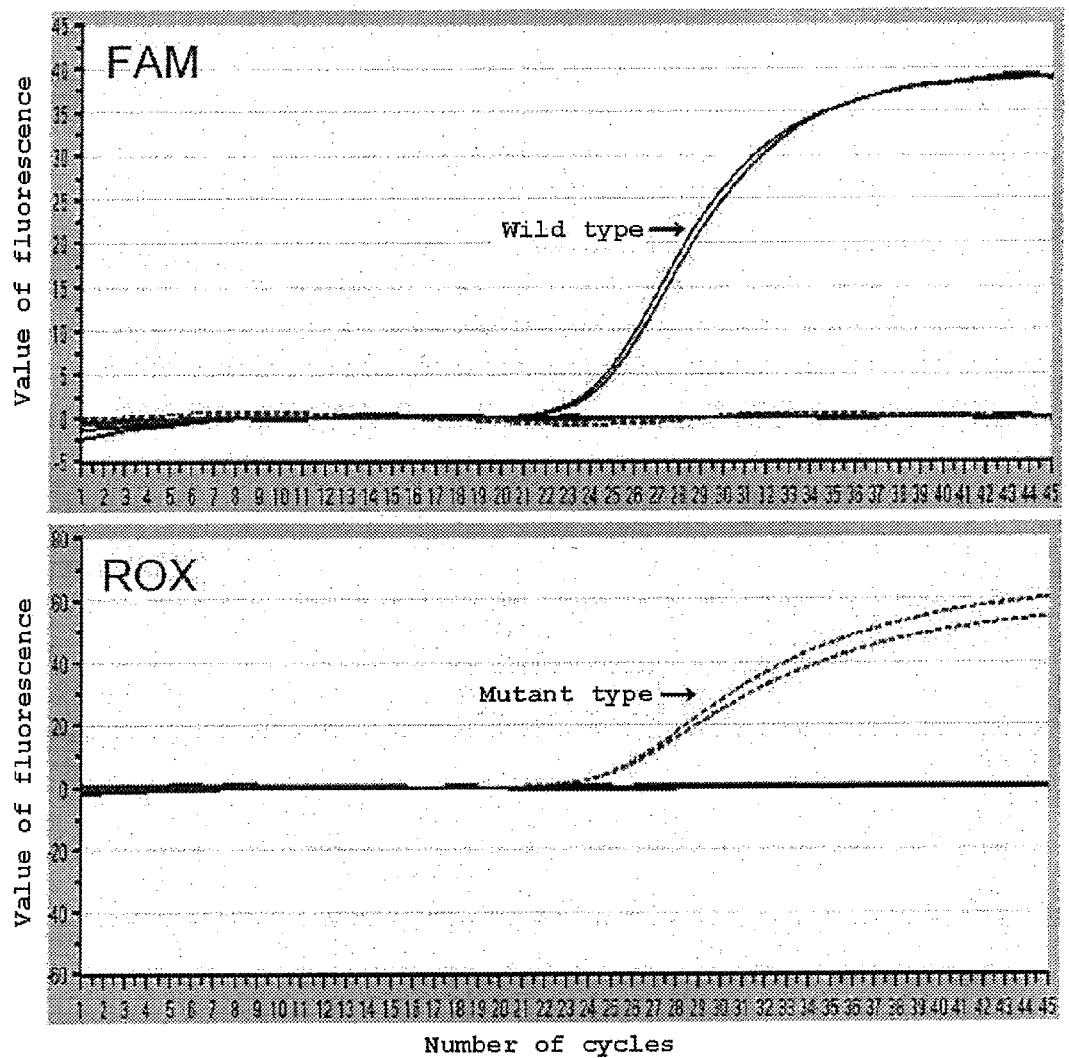
FIG. 6 represents graphs each showing an example of the results of specificity due to the Tm Values of RNA-containing probes designed in the method according to the present invention.
Figure 7:
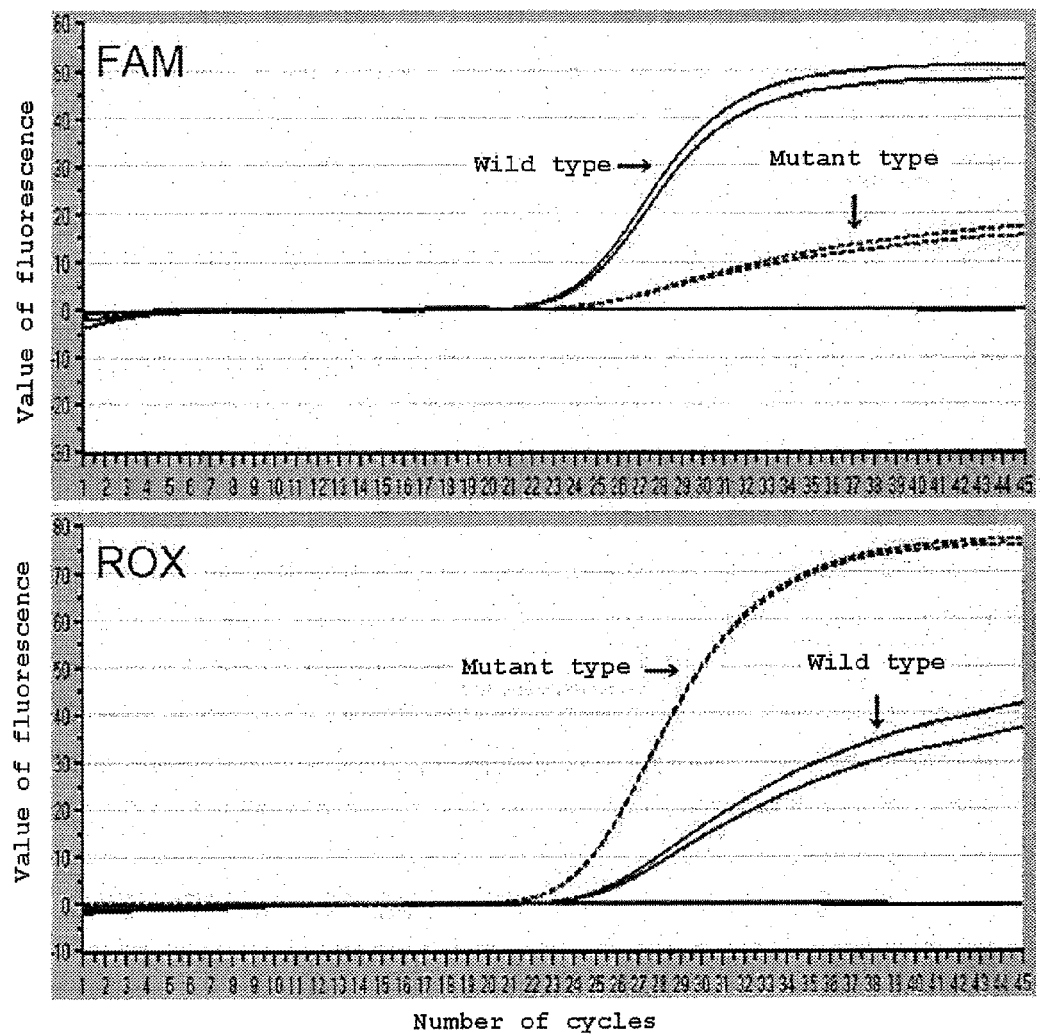
FIG. 7 represents graphs each showing an example of the results of specificity due to the Tm values of RNA-containing probes designed in the method according to the present invention.
Figure 8:
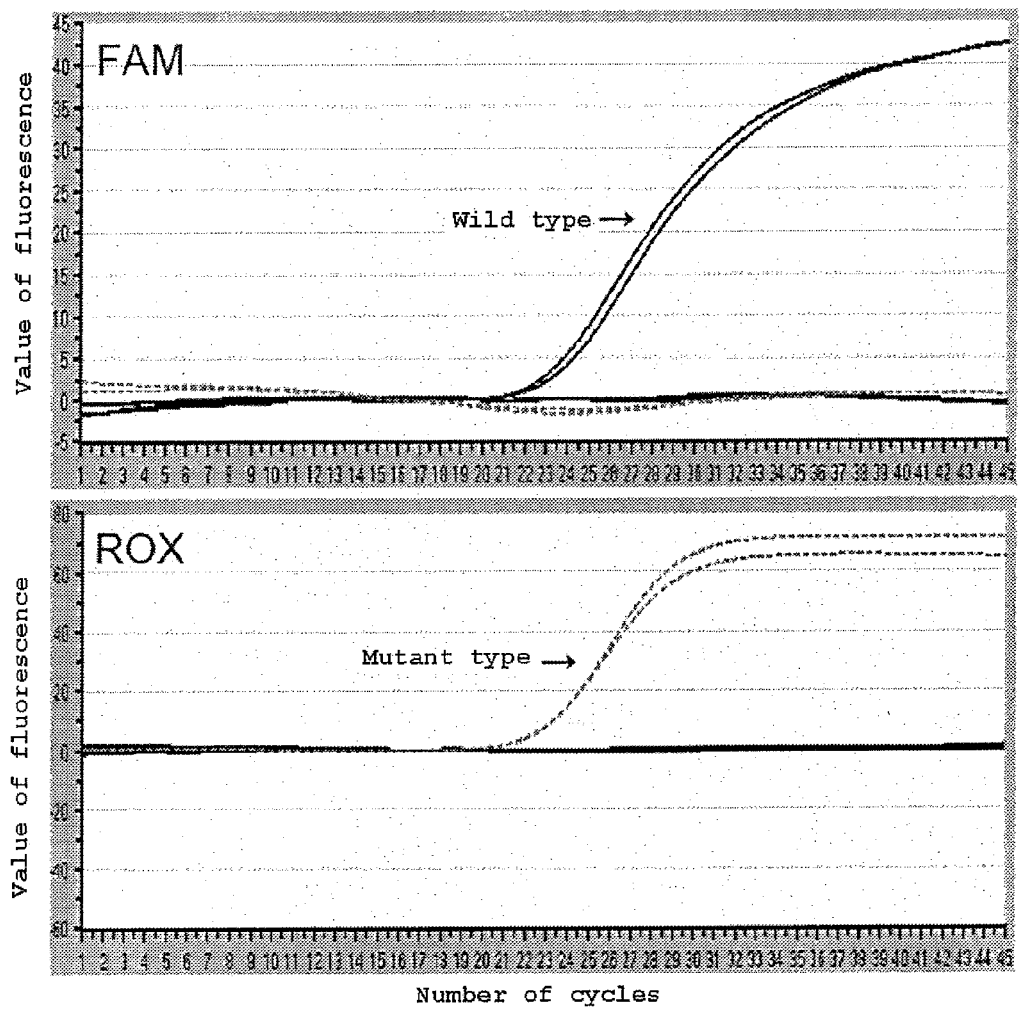
FIG. 8 represents graphs each showing an example of the results of specificity due to the Tm values of RNA-containing probes designed in the method according to the present invention.
Figure 9:
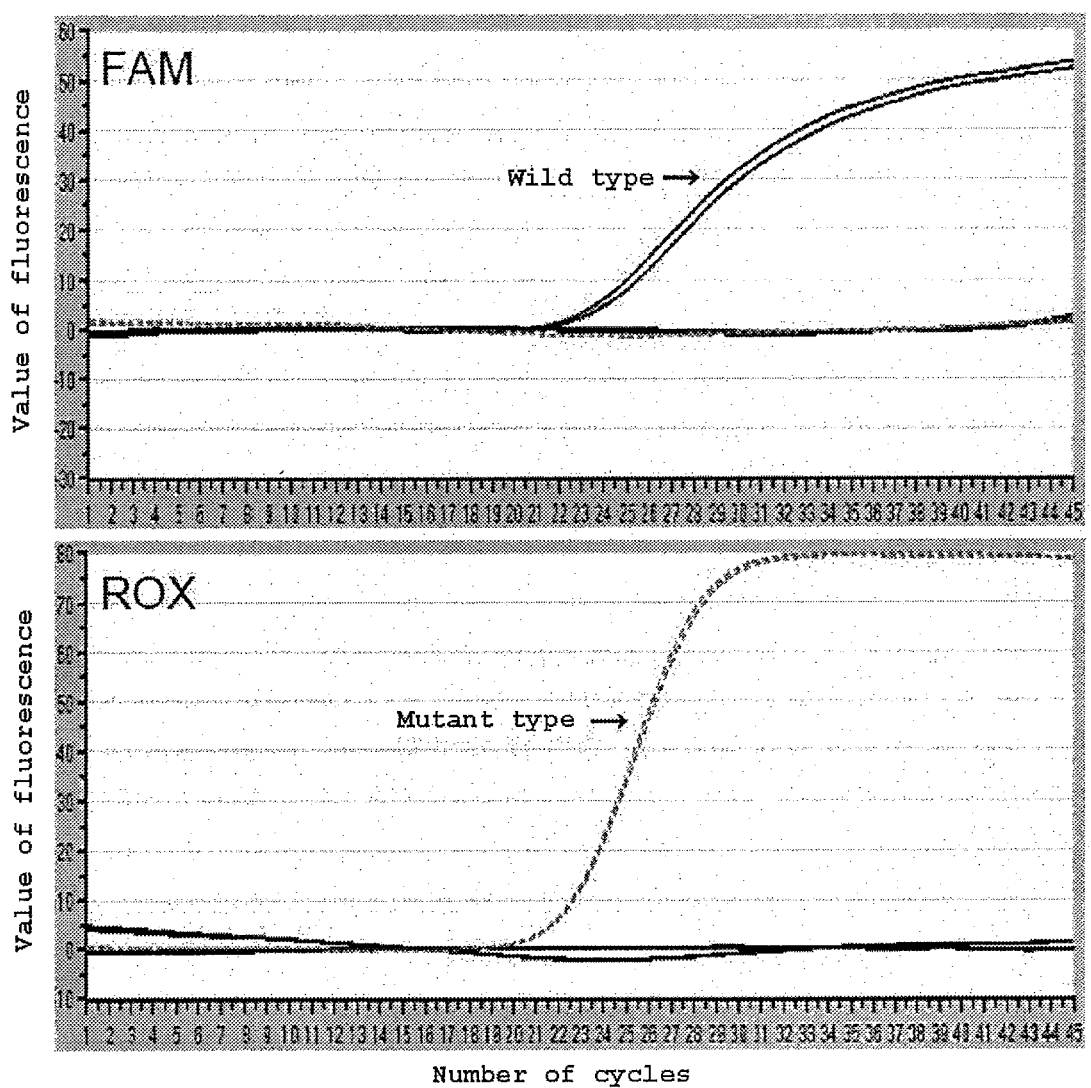
FIG. 9 represents graphs each showing an example of the results of specificity due to the Tm values of RNA-Containing probes designed in the method according to the present invention.

The results of the respective reactions are shown in FIGS. 4 to 9. In these figures, the upper panel shows the detection of FAM signal and the lower panel shows the detection of ROX signal. The vertical axis of the respective panels represents values of fluorescence from FAM and from ROX and the horizontal axis represents the number of cycles. The solid lines show results with a wild-type template and the dotted lines show results with a mutant-type template. In FIGS. 4 and 5, which show the results of detection of rs5443, the lines "wild-type" represent results when the nucleotide at the SNP position in the genome sequence is C and the lines "mutant-type" represent results when the nucleotide at the SNP position in the genome sequence is T. In FIGS. 6 and 7, which show the results of detection of rs1654416, the lines "wild-type" represent results when the nucleotide at the SNP position in the genome sequence is T and the lines "mutant-type" represent results when the nucleotide at the SNP position in the genome sequence is C. In FIGS. 8 and 9, which show the results of detection of rs1799821, the lines "wild-type" represent results when the nucleotide at the SNP position in the genome sequence is G and the lines "mutant-type" represent results when the nucleotide at the SNP position in the genome sequence is A.

These results demonstrate that regarding the detection of the rs5443 SNP, rs5443 C probe for detecting the wild-type SNP among RNA-containing probes designed to have a Tm value of 25 to 32° C., resulted in the detection only of the wild-type SNP (FAM in FIG. 4, upper panel). Rs5443 T probe for detecting the mutant-type SNP resulted in the specific detection only of the mutant-type SNP (ROX in FIG. 4, lower panel). Rs5443 C probe 2 for detecting the wild-type SNP among RNA-containing probes designed to have a Tm value of 35 to 40° C. resulted in the detection of the wild-type SNP and additionally the detection of the mutant-type SNP with a weak signal (FAM in FIG. 5, upper panel). R85443 T probe 2 for detecting the mutant-type SNP resulted in the detection the mutant-type SNP and additionally the detection of the wild-type SNP with a weak signal (ROX in FIG. 5, lower panel). Similar results were obtained with the RNA-containing probes designed for rs1654416 (FIGS. 6 and 7). With all the RNA-containing probes designed for rs1799821, each of the probes resulted in the specific detection either of the wild-type SNP or of the mutant-type SNP (FIGS. 8 and 9). From the results shown in FIGS. 4 to 9, it turned out that designing the RNA-containing probe with a Tm value in the range of 25 to 40° C. allowed specific detection of SNPs.

Example 3

A further examination was made of the specificity of reactions due to the Tm values of RNA-containing probes for detecting a target nucleic acid, and an examination was made of the specificity due to amounts of RNase H added to the reactions. First, probes were designed which each contained one of the SNPs described in Example 2 (rs5443, rs1654416, and rs1799821) and had a Tm value of 40° C. or higher. In the case of rs5443, probes were designed which were designed in the antisense strand of the genome sequence and in which the nucleotides corresponding to the SNP position on the complementary strand of the genome sequence were set as an RNA located at the 4th nucleotide and at the 3rd nucleotide from the 3' end of the probe (SEQ ID NOs:24 and 25). In the case of rs1654416, probes were designed which were designed in the antisense strand of the genome sequence and in which the nucleotides corresponding to the SNP position on the complementary strand of the genome sequence were set as an RNA located at the 4th nucleotide from the 3' end (SEQ ID NO:26) and the 4th nucleotide from the 5' end of the probe (SEQ ID NO:27). In the case of rs1799821, probes were designed which were designed in the antisense strand of the genome sequence and in which the nucleotides adjacent to the 3' side of the nucleotide corresponding to the SNP position on the complementary strand of the genome sequence were set as an RNA located at the 3rd nucleotide from the 5' end (SEQ ID NO:28) and the 4th nucleotide from the 3' end of the probe (SEQ ID NO:29). The sequences and Tm values of the designed probes and the type of fluorescent labels of the RNA-containing probes in their synthesis are shown in Table 9. For the sequences in the table, the nucleotide in parenthesis ( ) represents an RNA.

TABLE 9

| Probe name | Length | Sequence | Tm vale | Probe labels | SEQ ID NO. |
|---|---|---|---|---|---|
| rs5443 C probe3 | 12mer | aaggccac(g) gac | 45.1 | Eclipse-labeled at the 5' end FAM-labeled at the 3' end | No. 24 |
| rs5443 T probe3 | 14mer | gagaaggccac (a)ga | 45.7 | Eclipse-labeled at the 5' end ROX-labeled at the 3' end | No. 25 |
| rs1654416 C probe3 | 15mer | cattcacaaac (g)aag | 43.3 | Eclipse-labeled at the 5' end FAM-labeled at the 3' end | No. 26 |
| rs1654416 T probe3 | 15mer | aac(a)aagtc ttcaca | 41.1 | Eclipse-labeled-at the 5' end ROX-labeled at the 3' end | No. 27 |
| rs1799821 A probe3 | 14mer | at(g)gcagta gagcc | 45.8 | Eclipse-labeled at the 5' end FAM-labeled at the 3' end | No. 28 |
| rs1799821 G probe3 | 13mer | aaagtggac(g) gca | 45.4 | Eclipse-labeled at the 5' end ROX-labeled at the 3' end | No. 29 |

For the above-mentioned RNA-containing probes, primer pairs were designed such that Cycleave PCR was able to be carried out. For the probes designed from rs5443, a pair of primers, rs5443 F3 primer and rs5443 R3 primer (SEQ ID NOs:30 and 31), was designed. For the RNA-containing probes designed from rs1654416, a pair of primers, rs1654416 F3 primer and rs1654416 R3 primer (SEQ ID NOs:32 and 33), was designed. For the RNA-containing probes designed from rs1799821, a pair of primers, rs1799821 F3 primer and rs1799821 R3 primer (SEQ ID NOs:34 and 35), was designed.

The above-mentioned RNA-containing probes and primers were each synthesized, and Cycleave PCRs were performed as in Example 2. In these reactions, the Tli RNase H II supplied with the kit was prepared using the buffer supplied with the kit, so that amounts of the Tli RNase H II added to the reactions were 100 U (an amount which was usually added), 10 U, and 5 U, which were used for the respective probes.

Figure 10:
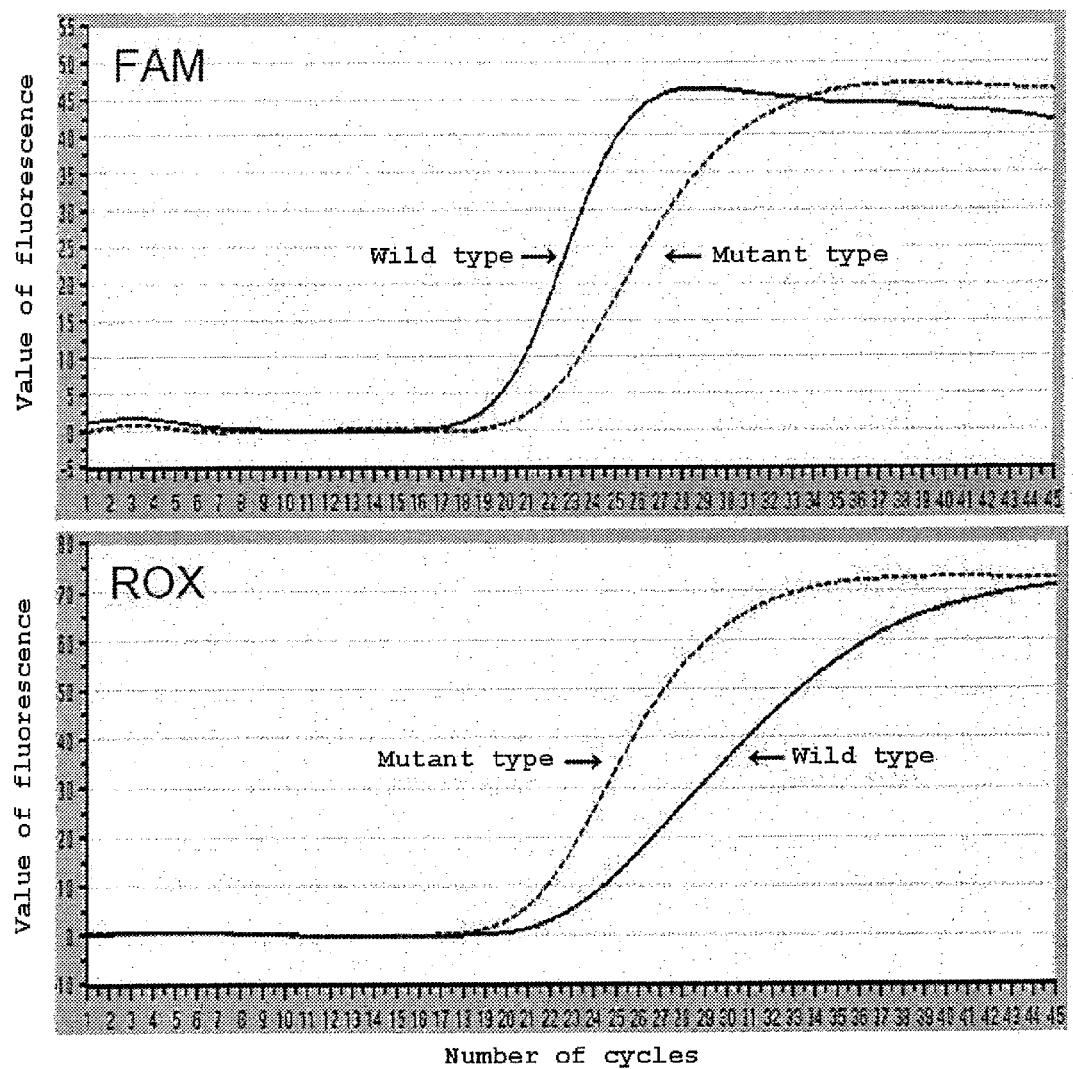
FIG. 10 represents graphs each showing an example of the results of specificity due to the Tm-values of RNA-containing probes designed in the method according to the present invention.
Figure 11:
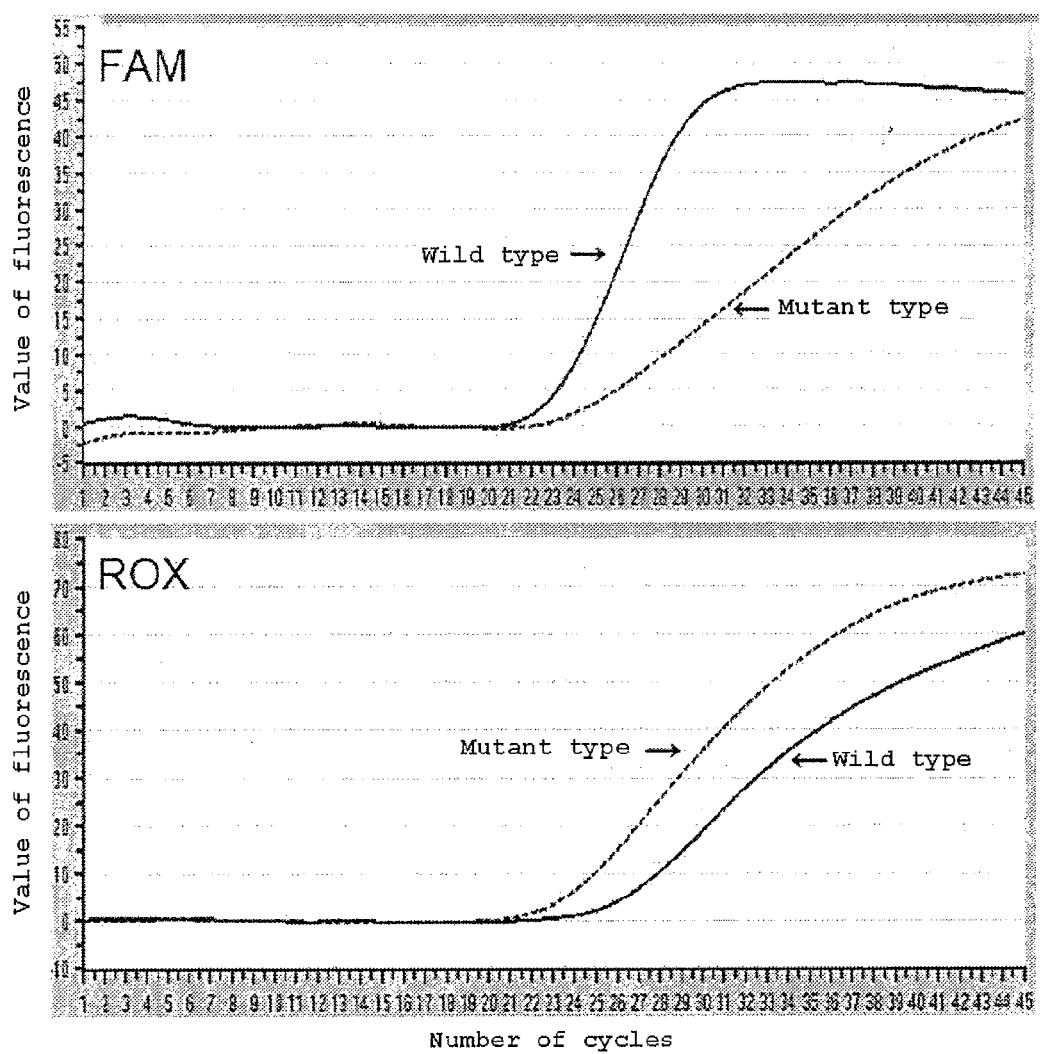
FIG. 11 represents graphs each showing an example of the results of specificity due to the Tm values of RNA-containing probes designed in the method according to the present invention.
Figure 12:
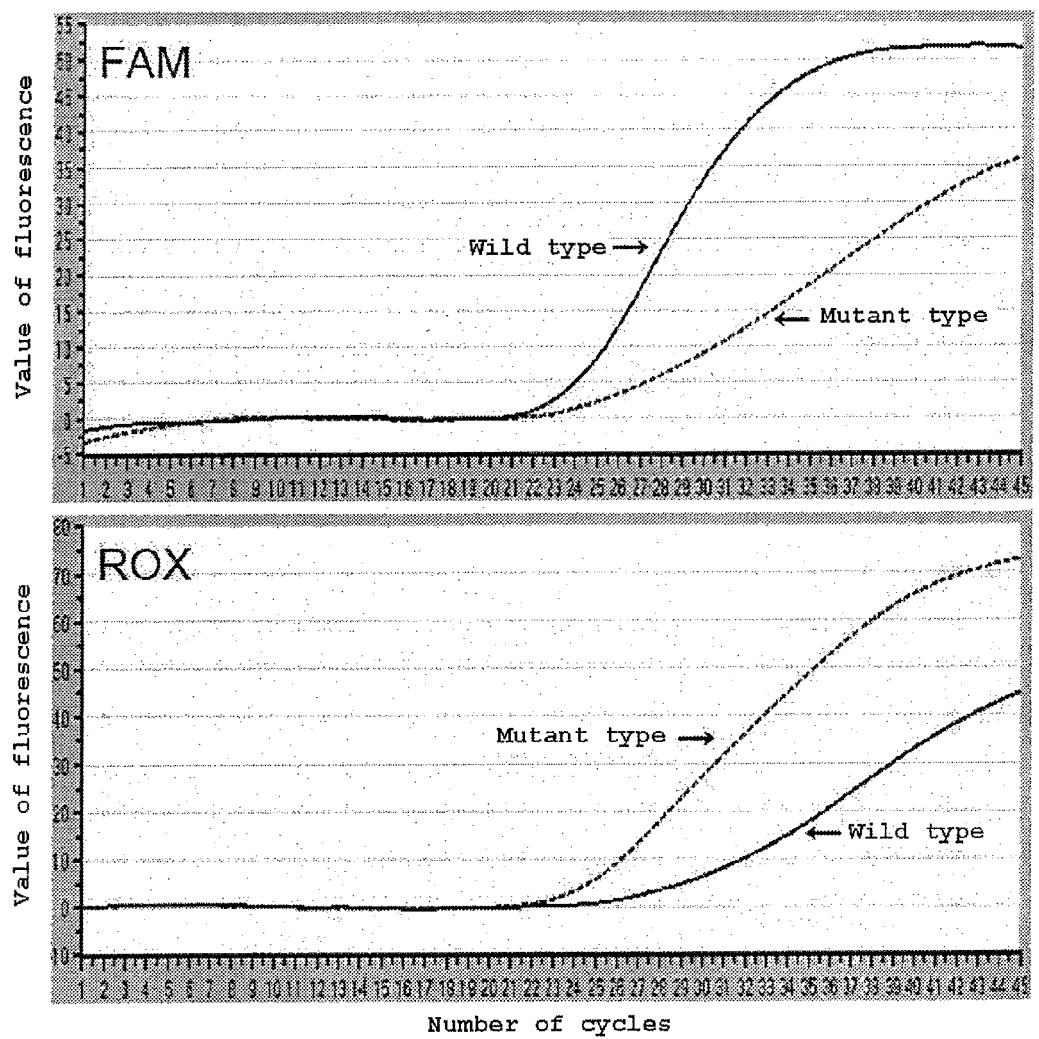
FIG. 12 represents graphs each showing an example of the results of specificity due to the Tm values of RNA-containing probes designed in the method according to the present invention.
Figure 13:
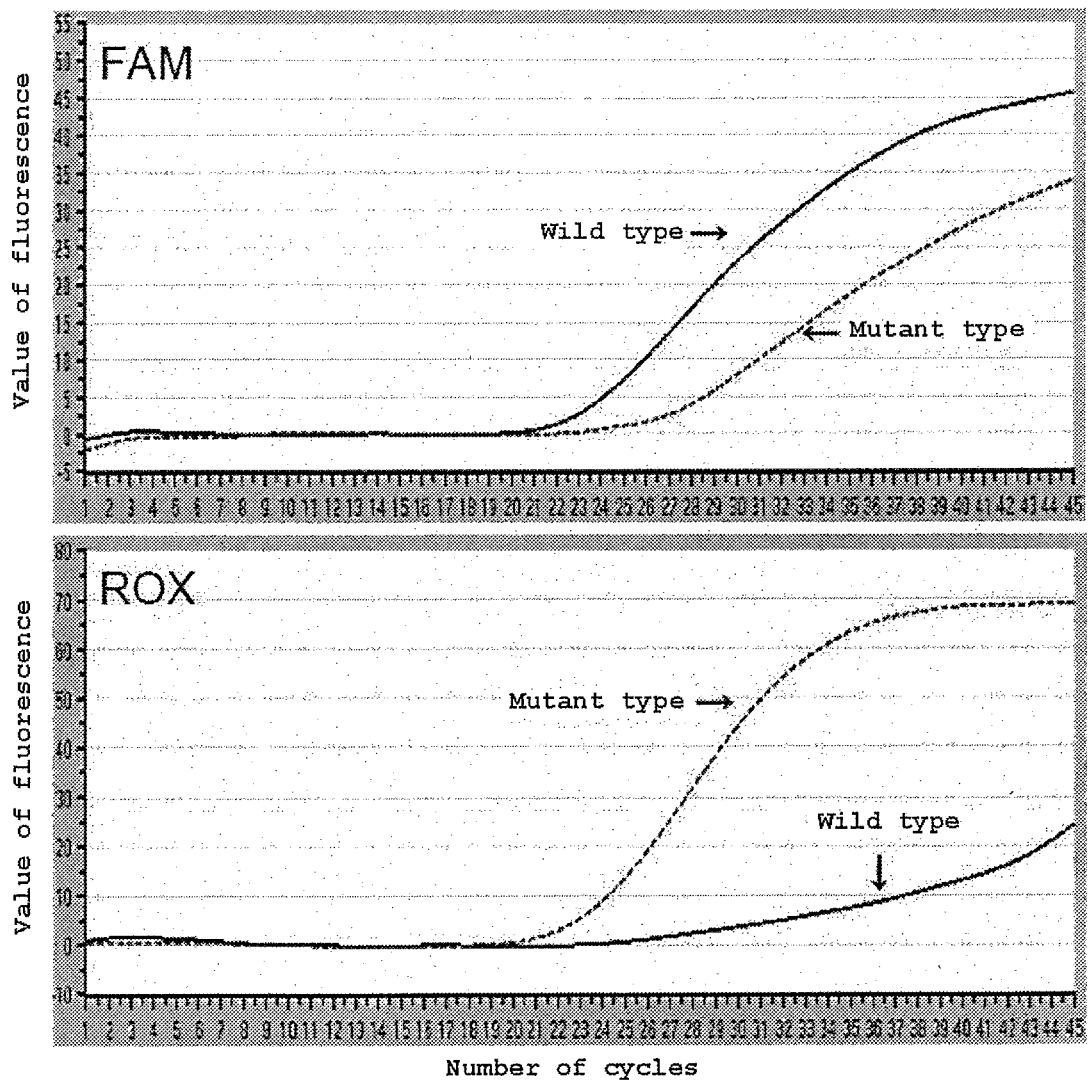
FIG. 13 represents graphs each showing an example of the results of specificity due to the Tm values of RNA-containing probes designed in the method according to the present invention.
Figure 14:
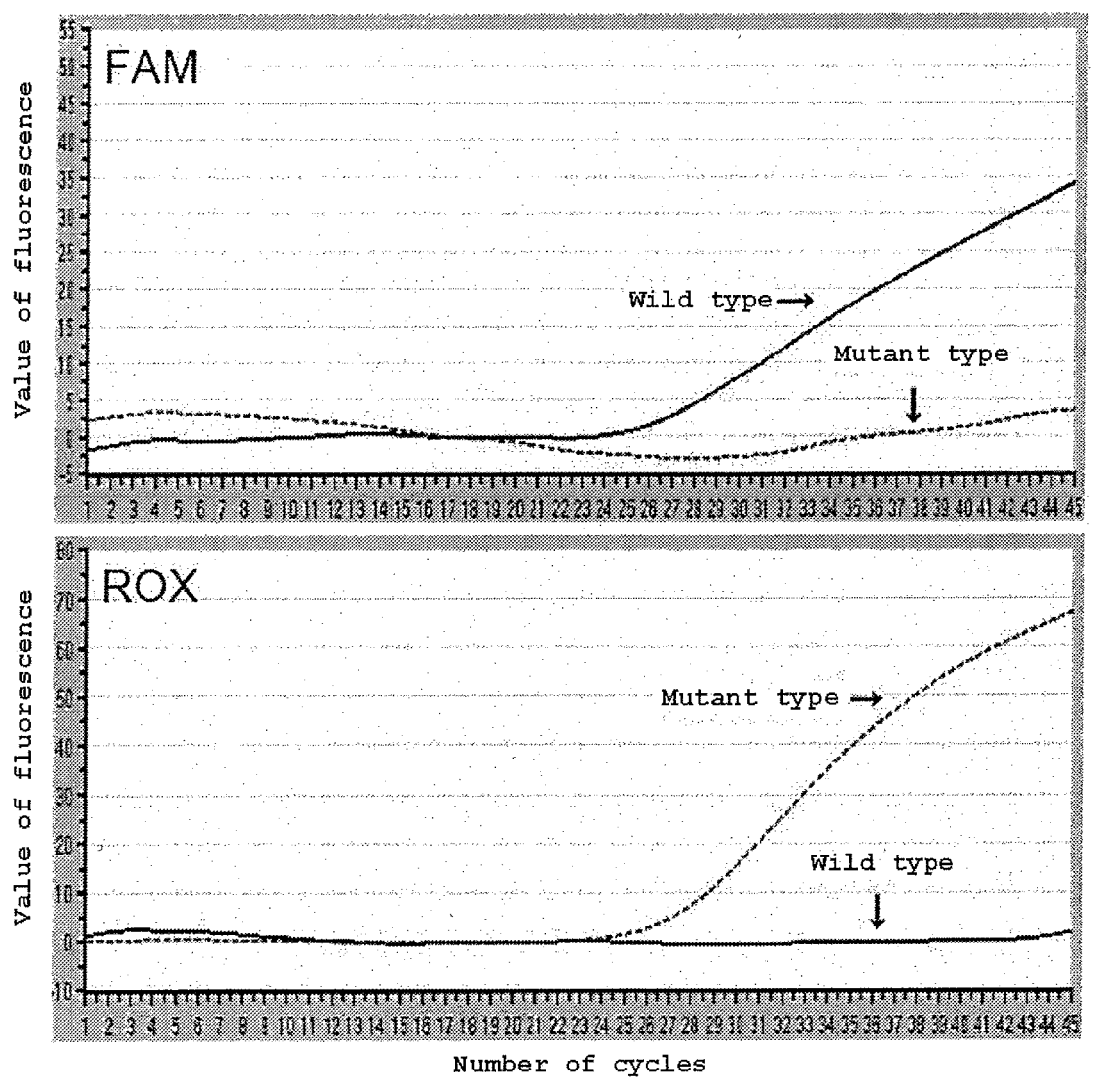
FIG. 14 represents graphs each showing an example of the results of specificity due to the Tm values of RNA-containing probes designed in the method according to the present invention.
Figure 15:
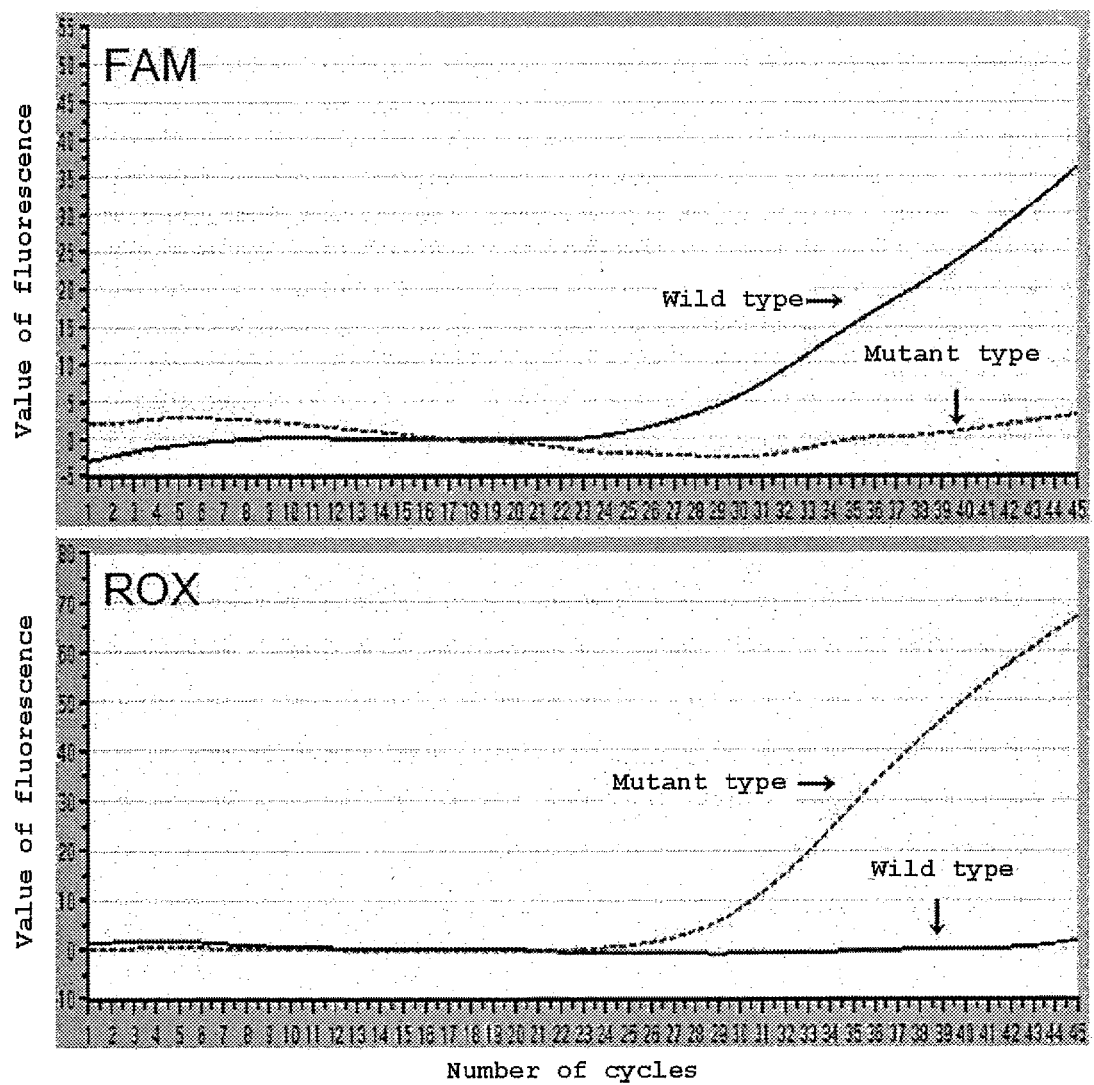
FIG. 15 represents graphs each showing an example of the results of specificity due to the Tm values of RNA-containing probes designed in the method according to the present invention.
Figure 16:
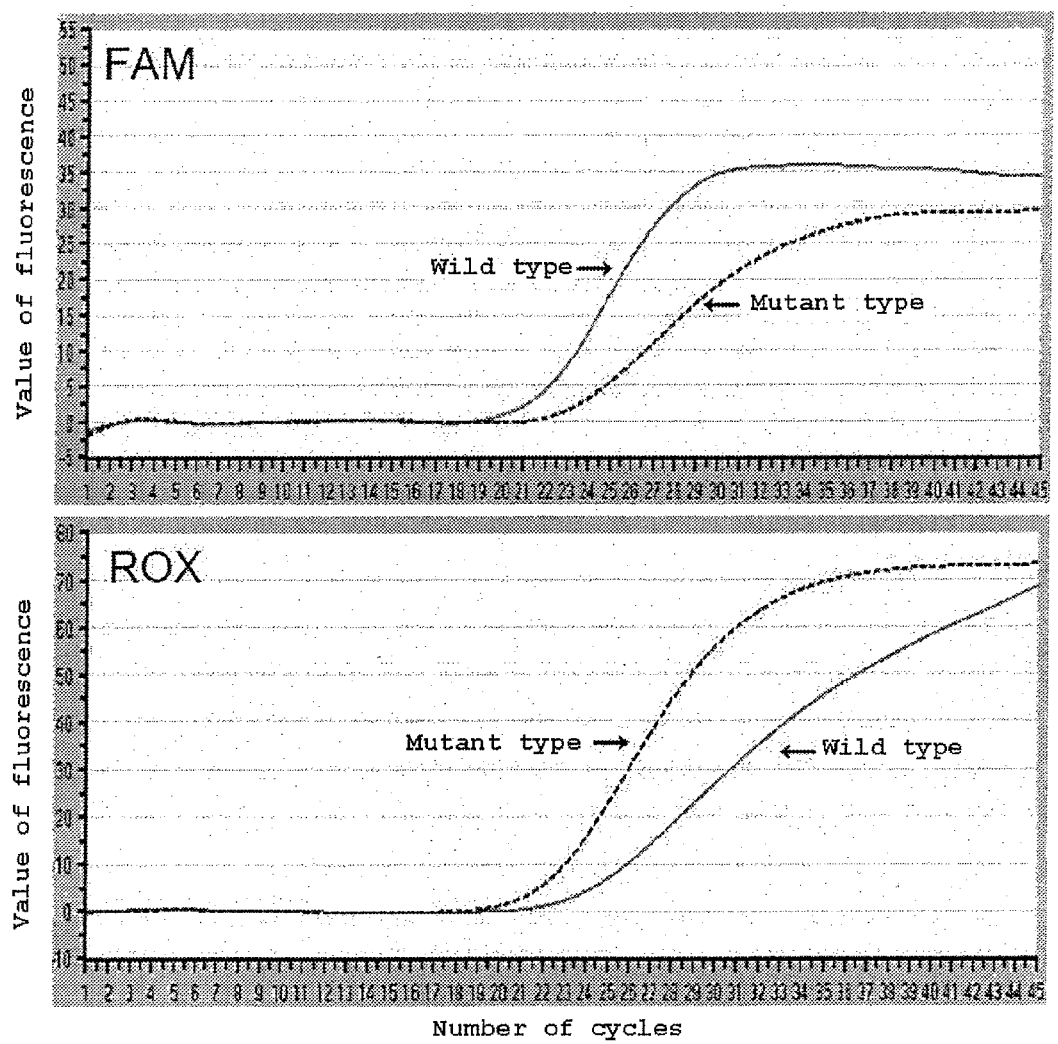
FIG. 16 represents graphs each showing an example of the results of specificity due to the Tm values of RNA-containing probes designed in the method according to the present invention.
Figure 17:
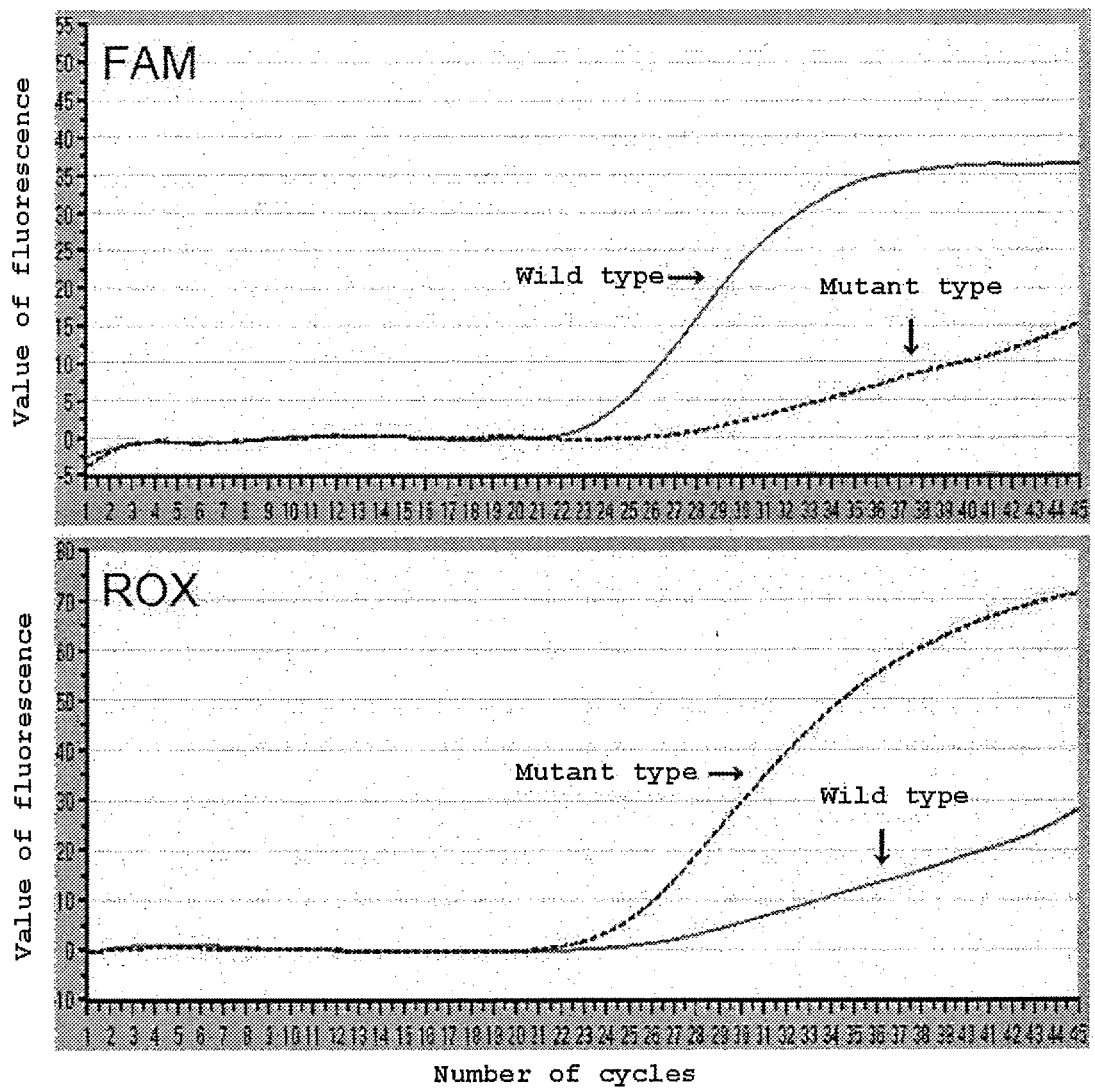
FIG. 17 represents graphs each showing an example of the results of specificity due to the Tm values of RNA-containing probes designed in the method according to the present invention.
Figure 18:
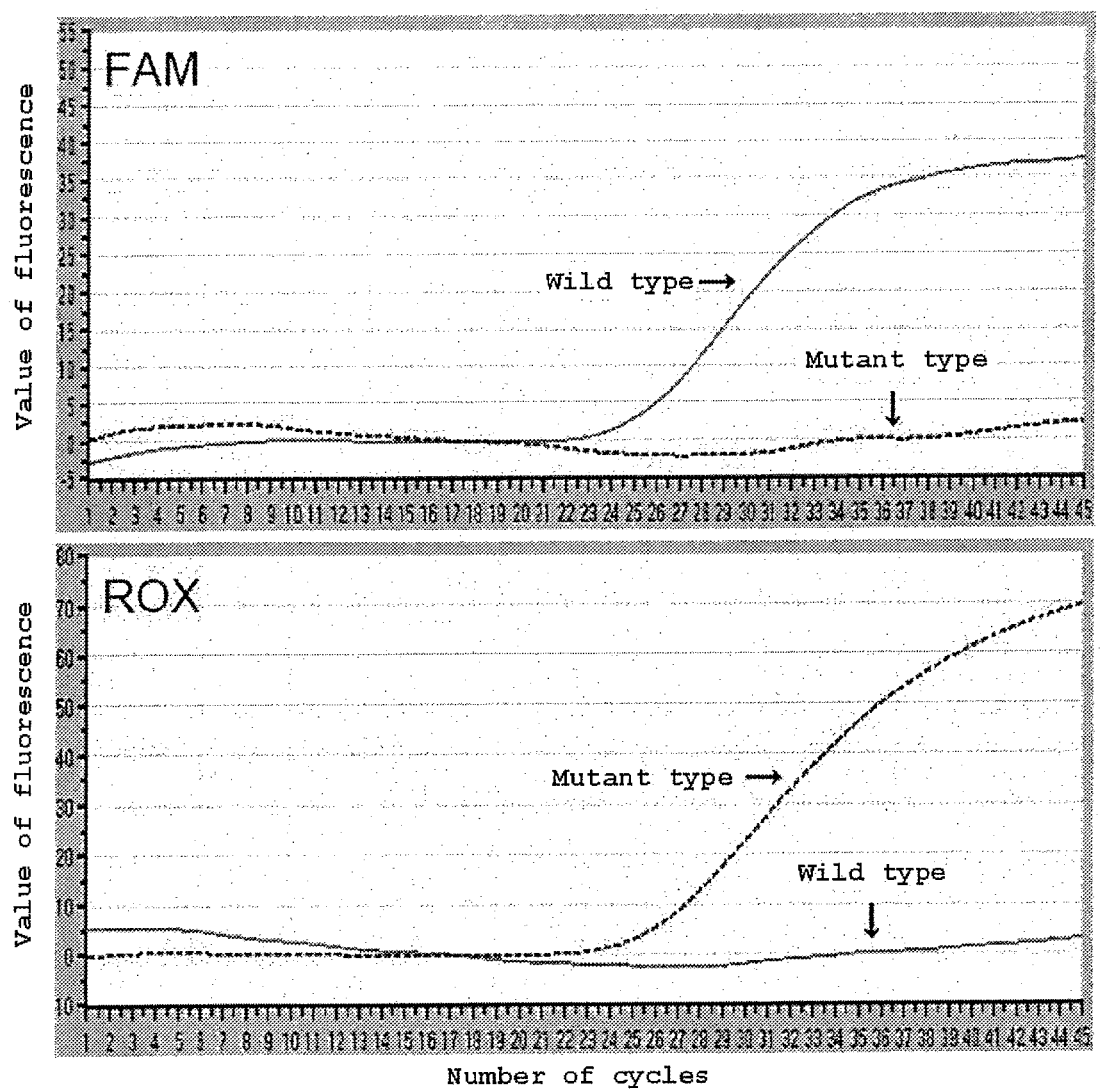
FIG. 18 represents graphs each showing an example of the results of specificity due to the Tm values of RNA-containing probes designed in the method according to the present invention.

The results of rs5443 are shown in FIG. 10 (when the amount of Tli RNase H added was 100 U), FIG. 11 (when the amount of Tli RNase H added was 10 U); and FIG. 12 (when the amount of Tli RNase H added was 5 U). The results of rs1654416 are shown in FIG. 13 (when the amount of Tli RNase H added was 100 U), FIG. 14 (when the amount of Tli RNase H added was 10 U), and FIG. 15 (when the amount of Tli RNase H added was 5 U). The results of rs1799821 are shown in FIG. 16 (when the amount of Tli RNase H added was 100 U), FIG. 17 (when the amount of Tli RNase H added was 10 U), and FIG. 18 (when the amount of Tli RNase H added was 5 U). In these figures, the upper panel shows the detection of FAM signal and the lower panel shows the detection of ROX signal. The vertical axis of the respective panels represents values of fluorescence from FAM and from ROX and the horizontal axis represents the number of cycles. The solid lines show results with a wild-type template and the dotted lines show results with a mutant-type template.

These results demonstrate that for any of the RNA-containing probes for detecting the target nucleic acid which were designed to have a Tm value of 40° C. or higher, at the usual amount of Tli RNase H added (100 U), the respective FAM-labeled probes for specifically detecting only the wild-type also resulted in the detection of the mutant-type. Furthermore, the respective ROX-labeled probes for specifically detecting only the mutant-type also resulted in the detection of the wild-type. Consequently, it turned out that the RNA-containing probes for detecting the target nucleic acid which were designed to have a Tm value of 40° C. or higher were not capable of specific detection.

From the results of the examination of the specificity due to amounts of RNase H added, using the RNA-containing probes for detecting the target nucleic acid which were designed to have a Tm value of 40° C. or higher, it turned out that with s1799821 G probe 3 it was found to improve the specificity by decreasing the amount of Tli RNase H added to 5 U, whereas with the others the specificity tended to be improved to some extent, but the amplification curves exhibited less steep shapes and Ct values were delayed, and thus these probes had reduced reactivity. From this, it was demonstrated that when the RNA-containing probes for detecting the target nucleic acid which were designed to have a Tm value of 40° C. or higher were used, most of the probes were not capable of specific detection.

INDUSTRIAL APPLICABILITY

According to the present invention, there is provided a method for designing an RNA-containing probe for detecting a target nucleic acid which is capable of simple and efficient detection of the target nucleic acid, without the basis of researchers' experiences or sense. There are also provided a method and device for processing nucleotide sequence, which make it possible that an RNA-containing probe for detecting a target nucleic acid is easily designed even by researchers having little or no experience in the art, and thus are extremely useful not only in the field of genetic engineering, but also in the field of medical research.

EXPLANATION OF LETTERS OR NUMERALS

ST1: Process step of entering the nucleotide sequence of a target nucleotide and information describing a target nucleotide ST1: Process step of entering the nucleotide sequence of a target nucleotide and information describing a target nucleotide ST2: Process step of generating the complementary nucleotide sequence of the target nucleic acid
ST3: Process step of determining the RNA position and the order of priority
ST4: Process step of generating information describing partial nucleotide sequences
ST5: Process step of making a determination based on Tm values
ST6: Process step of deleting string R from data memory 23
ST7: Process step of deleting string R from data memory 23
ST8: Process step of extracting partial nucleotide sequences
ST9: Process step of designing primer sequences
ST10: Process step of outputting
ST11 to ST17: Process steps of determination
ST18 to ST25: Process steps of generating information
ST31: Process step of generating information describing partial nucleotide sequences
ST32: Process step of generating information describing partial nucleotide sequences
ST33: Process step of generating information about the order of priority for partial nucleotide sequences
ST41: Process step of reading out strings K, M, and N
ST44: Process step of generating string P (string 0, number y, symbol z, symbol ST31)
10: Device for processing a nucleotide sequence
20: CPU
21: ROM
22: RAM
23: Data memory
24: Program memory
41: Keyboard
42: Mouse
43: CRT display
45: CD-ROM drive device
45a: CD-ROM
50: Internet
60: Gene database server unit
70: Table summarizing the form of data which are entered or generated in ST1 to ST4
71: Reference table in generating the complementary nucleotide sequence
72: Reference table in determining the RNA position
73: Reference table in making a determination of a purine nucleotide
74: Reference table in determining the order of priority
75: Reference table in determining the order of priority
76: Reference table in determining the order of priority
77: Reference table in making a determination as to whether or not 25° C. ≤Tm value ≤40° C.
78: Table of output information about partial nucleotide sequences and primer sequences
Sequence Listing Free Text
SEQ ID NO:1; Target nucleic acid template 1.
SEQ ID NO:2; Chimeric oligonucleotide probe central to detect the template 1. The 7th nucleotide from 5' end is RNA.
SEQ ID NO:3; Chimeric oligonucleotide probe 5'-4mer to detect the template 1. The 4th nucleotide from 5' end is RNA.
SEQ ID NO:4; Chimeric oligonucleotide probe 5'-3mer to detect the template 1. The 3rd nucleotide from end is RNA.
SEQ ID NO:5 Chimeric oligonucleotide probe 3'-4mer to detect the template 1. The 4th nucleotide from 3 end is RNA.
SEQ ID NO:6 Chimeric oligonucleotide probe 3'-3mer to detect the template 1. The 3rd nucleotide from 3' end is RNA.
SEQ ID NO:7; Chimeric oligonucleotide rs5443 C probe2 to detect the SNP of rs5443. The third nucleotide from the 3' end is RNA.
SEQ ID NO:8; Chimeric oligonucleotide rs5443 T probe to detect the SNP of rs5443. The third nucleotide from the 3' end is RNA.
SEQ ID NO: 9; Chimeric oligonucleotide rs1654416 C probe to detect the SNP of rs1654416. The third nucleotide from the 3' end is RNA.
SEQ ID NO:10; chimeric oligonucleotide rs1654416 T probe to detect the SNP of rs1654416'. The third nucleotide from the 3' end is RNA.
SEQ ID NO:11; Chimeric oligonucleotide rs1654416 C probe2 to detect the SNP of rs1654416. The third nucleotide from the 3' end is RNA.
SEQ ID NO:12; Chimeric oligonucleotide rs1654416 T probe2 to detect the SNP of rs1654416. The third nucleotide from the 3' end is RNA.
SEQ ID NO:13; Chimeric oligonucleotide rs1799821 A probe to detect the SNP of rs1799821. The third nucleotide from the 5' end is RNA.
SEQ ID NO:14; Chimeric oligonucleotide rs1799821 A probe2 to detect the SNP of rs1799821. The third nucleotide from the 3' end is RNA.
SEQ ID NO:15; Chimeric oligonucleotide rs1799821 G probe2 to detect the SNP of rs1799821. The third nucleotide from the 3' end is RNA.
SEQ ID NO:16; rs5443 F primer to amplify the DNA region including rs5443 C probe or rs5443 T probe.
SEQ ID NO:17; rs5443 R primer to amplify the DNA region including rs5443 C probe or rs5443 T probe.
SEQ ID NO:18; rs5443 F2 primer to amplify the DNA region including rs5443 C probe2 or rs5443 T probe2.
SEQ ID NO:19; rs5443 R2 primer to amplify the DNA region including rs5443 C probe2 or rs5443 T probe2.
SEQ ID NO:20; rs1654416 F primer to amplify the DNA region including rs1654416 C probe, rs1654416 T probe, rs1654416 C probe2 or rs1654416 T probe2.
SEQ ID NO:21; rs1654416 R primer to amplify the DNA region including rs1654416 C probe, rs1654416 T probe, rs1654416 C probe2 or rs1654416 T probe2.
SEQ ID NO:22; rs1799821 F primer to amplify the DNA region including rs1799821 A probe, rs1799821 G probe, rs1799821 A probe2 or rs1799821 G probe2
SEQ ID NO:23; rs1799821 R primer to amplify the DNA region including rs1799821 A probe, rs1799821 G probe, rs1799821 A probe2 or rs1799821 G probe2.
SEQ ID NO:24; Chimeric oligonucleotide rs5443 C probe3 to detect the SNP of rs5443. The 4th nucleotide from the 3' end is RNA.
SEQ ID NO:25; Chimeric oligonutleotide rs5443 T probe3 to detect the SNP of rs5443. The 3rd nucleotide from the end is RNA.
SEQ ID NO:26; Chimeric oligonucleotide rs1654416 C probe3 to detect the SNP of rs1654416. The 4th nucleotide from the 3' end is RNA.
SEQ ID NO:27; Chimeric oligonucleotide rs1654416 T probe3 to detect the SNP of rs1654416. The 4th nucleotide from the 5' end is RNA.
SEQ ID NO:28; Chimeric oligonucleotide rs1799821 A probe3 to detect the SNP of rs1799821. The 3rd nucleotide from the 5' end is RNA.
SEQ ID NO:29; Chimeric oligonucleotide rs1799821 G probe3 to detect the SNP of rs1799821. The 4th nucleotide from the 3' end is RNA.
SEQ ID NO:30; rs5443 F3 primer to amplify the DNA region including rs5443 C probe3 or rs5443 T probe3.

SEQ ID NO:31; rs5443 R3 primer to amplify the DNA region including rs5443 C probe3 or rs5443 T probe3.
SEQ ID NO:32; rs1654416 F3 primer to amplify the DNA region including rs1654416 C probe3 or rs1654416 T probe3.
SEQ ID NO:33; rs1654416 R3 primer to amplify the DNA region including rs1654416 C probe3 or rs1654416 T probe3 SEQ ID NO:34; rs1799821 F3 primer to amplify the DNA region including rs1799821 A probe3 or rs1799821 G probe3.
SEQ ID NO:35; rs1799821 R3 primer to amplify the DNA region including rs1799821 A probe3 or rs1799821 G probe3.

SEQUENCE LISTING

```
<160> NUMBER OF SEQ ID NOS: 52

<210> SEQ ID NO 1
<211> LENGTH: 23
<212> TYPE: DNA
<213> ORGANISM: Artificial Sequence
<220> FEATURE:
<223> OTHER INFORMATION: Target nucleic acid template 1
<220> FEATURE:
<221> NAME/KEY: misc_feature
<222> LOCATION: (9)..(11)
<223> OTHER INFORMATION: n is a, c, g, or t

<400> SEQUENCE: 1
aatatccgnn nggcattgaa gca                                              23

<210> SEQ ID NO 2
<211> LENGTH: 12
<212> TYPE: DNA
<213> ORGANISM: Artificial Sequence
<220> FEATURE:
<223> OTHER INFORMATION: Chimeric oligonucleotide probe central to
      detect the template 1. The 7th base from 5' end is RNA.

<400> SEQUENCE: 2
atgccmrmcg ga                                                          12

<210> SEQ ID NO 3
<211> LENGTH: 12
<212> TYPE: DNA
<213> ORGANISM: Artificial Sequence
<220> FEATURE:
<223> OTHER INFORMATION: Chimeric oligonucleotide probe 5'-4mer to
      detect the template 1. The 4th base from 5' end is RNA.

<400> SEQUENCE: 3
ccmrmcggat at                                                          12

<210> SEQ ID NO 4
<211> LENGTH: 12
<212> TYPE: DNA
<213> ORGANISM: Artificial Sequence
<220> FEATURE:
<223> OTHER INFORMATION: Chimeric oligonucleotide probe 5'-3mer to
      detect the template 1. The 3rd base from 5' end is RNA.

<400> SEQUENCE: 4
cmrmcggata tt                                                          12

<210> SEQ ID NO 5
<211> LENGTH: 12
<212> TYPE: DNA
<213> ORGANISM: Artificial Sequence
<220> FEATURE:
<223> OTHER INFORMATION: Chimeric oligonucleotide probe 3'-4mer to
      detect the template 1. The 4th base from 3' end is RNA.

<400> SEQUENCE: 5
acatgccmrm cg                                                          12
```

```
<210> SEQ ID NO 6
<211> LENGTH: 12
<212> TYPE: DNA
<213> ORGANISM: Artificial Sequence
<220> FEATURE:
<223> OTHER INFORMATION: Chimeric oligonucleotide probe 3'-3mer to
      detect the template 1. The 3rd base from 3' end is RNA.

<400> SEQUENCE: 6
tacatgccmr mc                                                         12

<210> SEQ ID NO 7
<211> LENGTH: 10
<212> TYPE: DNA
<213> ORGANISM: Artificial Sequence
<220> FEATURE:
<223> OTHER INFORMATION: Chimeric oligonucleotide rs5443 C probe2 to
      detect the SNP of rs5443. The 3rd base from the 3' end is RNA.

<400> SEQUENCE: 7
aggccacgga                                                            10

<210> SEQ ID NO 8
<211> LENGTH: 11
<212> TYPE: DNA
<213> ORGANISM: Artificial Sequence
<220> FEATURE:
<223> OTHER INFORMATION: Chimeric oligonucleotide rs5443 T probe to
      detect the SNP of rs5443. The 3rd base from the 3' end is RNA.

<400> SEQUENCE: 8
aaggccacag a                                                          11

<210> SEQ ID NO 9
<211> LENGTH: 11
<212> TYPE: DNA
<213> ORGANISM: Artificial Sequence
<220> FEATURE:
<223> OTHER INFORMATION: Chimeric oligonucleotide rs1654416 C probe to
      detect the SNP of rs1654416. The 3rd base from the 3' end is RNA.

<400> SEQUENCE: 9
tcacaaacga a                                                          11

<210> SEQ ID NO 10
<211> LENGTH: 12
<212> TYPE: DNA
<213> ORGANISM: Artificial Sequence
<220> FEATURE:
<223> OTHER INFORMATION: Chimeric oligonucleotide rs1654416 T probe to
      detect the SNP of rs1654416. The 3rd base from the 3' end is RNA.

<400> SEQUENCE: 10
ttcacaaaca aa                                                         12

<210> SEQ ID NO 11
<211> LENGTH: 13
<212> TYPE: DNA
<213> ORGANISM: Artificial Sequence
<220> FEATURE:
<223> OTHER INFORMATION: Chimeric oligonucleotide rs1654416 C probe2 to
      detect the SNP of rs1654416. The 3rd base from the 3' end is RNA.

<400> SEQUENCE: 11
attcacaaac gaa                                                        13
```

```
<210> SEQ ID NO 12
<211> LENGTH: 14
<212> TYPE: DNA
<213> ORGANISM: Artificial Sequence
<220> FEATURE:
<223> OTHER INFORMATION: Chimeric oligonucleotide rs1654416 T probe2 to
      detect the SNP of rs1654416. The 3rd base from the 3' end is RNA.

<400> SEQUENCE: 12
cattcacaaa caaa                                                     14

<210> SEQ ID NO 13
<211> LENGTH: 11
<212> TYPE: DNA
<213> ORGANISM: Artificial Sequence
<220> FEATURE:
<223> OTHER INFORMATION: Chimeric oligonucleotide rs1799821 A probe to
      detect the SNP of rs1799821. The 3rd base from the 5' end is RNA.

<400> SEQUENCE: 13
ccatccactt t                                                        11

<210> SEQ ID NO 14
<211> LENGTH: 12
<212> TYPE: DNA
<213> ORGANISM: Artificial Sequence
<220> FEATURE:
<223> OTHER INFORMATION: Chimeric oligonucleotide rs1799821 A probe2 to
      detect the SNP of rs1799821. The 3rd base from the 3' end is RNA.

<400> SEQUENCE: 14
tctactgcca tc                                                       12

<210> SEQ ID NO 15
<211> LENGTH: 11
<212> TYPE: DNA
<213> ORGANISM: Artificial Sequence
<220> FEATURE:
<223> OTHER INFORMATION: Chimeric oligonucleotide rs1799821 G probe2 to
      detect the SNP of rs1799821. The 3rd base from the 3' end is RNA.

<400> SEQUENCE: 15
ctactgccgt c                                                        11

<210> SEQ ID NO 16
<211> LENGTH: 16
<212> TYPE: DNA
<213> ORGANISM: Artificial Sequence
<220> FEATURE:
<223> OTHER INFORMATION: rs5443 F primer to amplify the DNA region
      including rs5443 C probe or rs5443 T probe.

<400> SEQUENCE: 16
tgccgcttgt ttgacc                                                   16

<210> SEQ ID NO 17
<211> LENGTH: 19
<212> TYPE: DNA
<213> ORGANISM: Artificial Sequence
<220> FEATURE:
<223> OTHER INFORMATION: rs5443 R primer to amplify the DNA region
      including rs5443 C probe or rs5443 T probe.

<400> SEQUENCE: 17
agttgaagtc gtcgtagcc                                                19
```

```
<210> SEQ ID NO 18
<211> LENGTH: 19
<212> TYPE: DNA
<213> ORGANISM: Artificial Sequence
<220> FEATURE:
<223> OTHER INFORMATION: rs5443 F2 primer to amplify the DNA region
      including rs5443 C probe2 or rs5443 T probe2.

<400> SEQUENCE: 18
ctcccacgag agcatcatc                                                19

<210> SEQ ID NO 19
<211> LENGTH: 20
<212> TYPE: DNA
<213> ORGANISM: Artificial Sequence
<220> FEATURE:
<223> OTHER INFORMATION: rs5443 R2 primer to amplify the DNA region
      including rs5443 C probe2 or rs5443 T probe2.

<400> SEQUENCE: 19
ttacccacac gctcagactt                                               20

<210> SEQ ID NO 20
<211> LENGTH: 20
<212> TYPE: DNA
<213> ORGANISM: Artificial Sequence
<220> FEATURE:
<223> OTHER INFORMATION: s1654416 F primer to amplify the DNA region
      including rs1654416 C probe, rs1654416 T probe, rs1654416 C
      probe2 or rs1654416 T probe2.

<400> SEQUENCE: 20
gcatgaaatg cctggttact                                               20

<210> SEQ ID NO 21
<211> LENGTH: 20
<212> TYPE: DNA
<213> ORGANISM: Artificial Sequence
<220> FEATURE:
<223> OTHER INFORMATION: rs1654416 R primer to amplify the DNA region
      including rs1654416 C probe, rs1654416 T probe, rs1654416 C
      probe2 or rs1654416 T probe2.

<400> SEQUENCE: 21
gggtttcagg gagcctagat                                               20

<210> SEQ ID NO 22
<211> LENGTH: 21
<212> TYPE: DNA
<213> ORGANISM: Artificial Sequence
<220> FEATURE:
<223> OTHER INFORMATION: rs1799821 F primer to amplify the DNA region
      including rs1799821 A probe, rs1799821 G probe, rs1799821 A
      probe2 or rs1799821 G probe2.

<400> SEQUENCE: 22
ccattaagga ccttgtccac t                                             21

<210> SEQ ID NO 23
<211> LENGTH: 19
<212> TYPE: DNA
<213> ORGANISM: Artificial Sequence
<220> FEATURE:
<223> OTHER INFORMATION: rs1799821 R primer to amplify the DNA region
      including rs1799821 A probe, rs1799821 G probe, rs1799821 A
      probe2 or rs1799821 G probe2.
```

```
<400> SEQUENCE: 23
atctgagcac tgccacacc                                                19

<210> SEQ ID NO 24
<211> LENGTH: 12
<212> TYPE: DNA
<213> ORGANISM: Artificial Sequence
<220> FEATURE:
<223> OTHER INFORMATION: Chimeric oligonucleotide rs5443 C probe3 to
      detect the SNP of rs5443. The 4th base from the 3' end is RNA.

<400> SEQUENCE: 24
aaggccacgg ac                                                       12

<210> SEQ ID NO 25
<211> LENGTH: 14
<212> TYPE: DNA
<213> ORGANISM: Artificial Sequence
<220> FEATURE:
<223> OTHER INFORMATION: Chimeric oligonucleotide rs5443 T probe3 to
      detect the SNP of rs5443. The 3rd base from the 3' end is RNA.

<400> SEQUENCE: 25
gagaaggcca caga                                                     14

<210> SEQ ID NO 26
<211> LENGTH: 15
<212> TYPE: DNA
<213> ORGANISM: Artificial Sequence
<220> FEATURE:
<223> OTHER INFORMATION: Chimeric oligonucleotide rs1654416 C probe3 to
      detect the SNP of rs1654416. The 4th base from the 3' end is RNA.

<400> SEQUENCE: 26
cattcacaaa cgaag                                                    15

<210> SEQ ID NO 27
<211> LENGTH: 15
<212> TYPE: DNA
<213> ORGANISM: Artificial Sequence
<220> FEATURE:
<223> OTHER INFORMATION: Chimeric oligonucleotide rs1654416 T probe3 to
      detect the SNP of rs1654416. The 4th base from the 5' end is RNA.

<400> SEQUENCE: 27
aacaaagtct tcaca                                                    15

<210> SEQ ID NO 28
<211> LENGTH: 14
<212> TYPE: DNA
<213> ORGANISM: Artificial Sequence
<220> FEATURE:
<223> OTHER INFORMATION: Chimeric oligonucleotide rs1799821 A probe3 to
      detect the SNP of rs1799821. The 3rd base from the 5' end is RNA.

<400> SEQUENCE: 28
atggcagtag agcc                                                     14

<210> SEQ ID NO 29
<211> LENGTH: 13
<212> TYPE: DNA
<213> ORGANISM: Artificial Sequence
<220> FEATURE:
<223> OTHER INFORMATION: Chimeric oligonucleotide rs1799821 G probe3 to
      detect the SNP of rs1799821. The 4th base from the 3' end is RNA.
```

```
<400> SEQUENCE: 29
aaagtggacg gca                                                          13

<210> SEQ ID NO 30
<211> LENGTH: 19
<212> TYPE: DNA
<213> ORGANISM: Artificial Sequence
<220> FEATURE:
<223> OTHER INFORMATION: rs5443 F3 primer to amplify the DNA region
      including rs5443 C probe3 or rs5443 T probe3.

<400> SEQUENCE: 30
ctcccacgag agcatcatc                                                    19

<210> SEQ ID NO 31
<211> LENGTH: 21
<212> TYPE: DNA
<213> ORGANISM: Artificial Sequence
<220> FEATURE:
<223> OTHER INFORMATION: rs5443 R3 primer to amplify the DNA region
      including rs5443 C probe3 or rs5443 T probe3.

<400> SEQUENCE: 31
cttcatggag tcccagacat t                                                 21

<210> SEQ ID NO 32
<211> LENGTH: 19
<212> TYPE: DNA
<213> ORGANISM: Artificial Sequence
<220> FEATURE:
<223> OTHER INFORMATION: s1654416 F3 primer to amplify the DNA region
      including rs1654416 C probe3 or rs1654416 T probe3.

<400> SEQUENCE: 32
agcatgaaat gcctggtta                                                    19

<210> SEQ ID NO 33
<211> LENGTH: 21
<212> TYPE: DNA
<213> ORGANISM: Artificial Sequence
<220> FEATURE:
<223> OTHER INFORMATION: rs1654416 R3 primer to amplify the DNA region
      including rs1654416 C probe3 or rs1654416 T probe3.

<400> SEQUENCE: 33
gggaatggag atatctagag g                                                 21

<210> SEQ ID NO 34
<211> LENGTH: 20
<212> TYPE: DNA
<213> ORGANISM: Artificial Sequence
<220> FEATURE:
<223> OTHER INFORMATION: rs1799821 F3 primer to amplify the DNA region
      including rs1799821 A probe3 or rs1799821 G probe3.

<400> SEQUENCE: 34
tggactcggc agtgttctgt                                                   20

<210> SEQ ID NO 35
<211> LENGTH: 20
<212> TYPE: DNA
<213> ORGANISM: Artificial Sequence
<220> FEATURE:
<223> OTHER INFORMATION: rs1799821 R3 primer to amplify the DNA region
      including rs1799821 A probe3 or rs1799821 G probe3.
```

-continued

```
<400> SEQUENCE: 35
tagctggctg gctctgtgga                                              20

<210> SEQ ID NO 36
<211> LENGTH: 11
<212> TYPE: DNA
<213> ORGANISM: Artificial Sequence
<220> FEATURE:
<223> OTHER INFORMATION: Synthetic probe 1 of Fig. 32

<400> SEQUENCE: 36
caggaaccat a                                                       11

<210> SEQ ID NO 37
<211> LENGTH: 11
<212> TYPE: DNA
<213> ORGANISM: Artificial Sequence
<220> FEATURE:
<223> OTHER INFORMATION: Synthetic probe 2 of Fig. 32

<400> SEQUENCE: 37
aggaaccata g                                                       11

<210> SEQ ID NO 38
<211> LENGTH: 12
<212> TYPE: DNA
<213> ORGANISM: Artificial Sequence
<220> FEATURE:
<223> OTHER INFORMATION: Synthetic probe 3 of Fig. 32

<400> SEQUENCE: 38
cactactatg gt                                                      12

<210> SEQ ID NO 39
<211> LENGTH: 10
<212> TYPE: DNA
<213> ORGANISM: Artificial Sequence
<220> FEATURE:
<223> OTHER INFORMATION: Synthetic probe 2 of Fig. 32

<400> SEQUENCE: 39
aggaaccgta                                                         10

<210> SEQ ID NO 40
<211> LENGTH: 11
<212> TYPE: DNA
<213> ORGANISM: Artificial Sequence
<220> FEATURE:
<223> OTHER INFORMATION: Synthetic probe 2 of Fig. 32

<400> SEQUENCE: 40
actactacgg t                                                       11

<210> SEQ ID NO 41
<211> LENGTH: 20
<212> TYPE: DNA
<213> ORGANISM: Artificial Sequence
<220> FEATURE:
<223> OTHER INFORMATION: Syntehtic primer

<400> SEQUENCE: 41
agcactgtgt ctccactcct                                              20
```

```
<210> SEQ ID NO 42
<211> LENGTH: 19
<212> TYPE: DNA
<213> ORGANISM: Artificial Sequence
<220> FEATURE:
<223> OTHER INFORMATION: Synthetic primer

<400> SEQUENCE: 42
cagcactgtg tctccactc                                                       19

<210> SEQ ID NO 43
<211> LENGTH: 17
<212> TYPE: DNA
<213> ORGANISM: Artificial Sequence
<220> FEATURE:
<223> OTHER INFORMATION: Synthetic primer

<400> SEQUENCE: 43
ccgcagagct tacctta                                                         17

<210> SEQ ID NO 44
<211> LENGTH: 19
<212> TYPE: DNA
<213> ORGANISM: Artificial Sequence
<220> FEATURE:
<223> OTHER INFORMATION: Synthetic primer

<400> SEQUENCE: 44
ctcaggtggg tgttgtgag                                                       19

<210> SEQ ID NO 45
<211> LENGTH: 19
<212> TYPE: DNA
<213> ORGANISM: Artificial Sequence
<220> FEATURE:
<223> OTHER INFORMATION: Synthetic primer

<400> SEQUENCE: 45
tgatctcagg tgggtgttg                                                       19

<210> SEQ ID NO 46
<211> LENGTH: 17
<212> TYPE: DNA
<213> ORGANISM: Artificial Sequence
<220> FEATURE:
<223> OTHER INFORMATION: Synthetic primer

<400> SEQUENCE: 46
gtgaggcagg gctgtaa                                                         17

<210> SEQ ID NO 47
<211> LENGTH: 22
<212> TYPE: DNA
<213> ORGANISM: Artificial Sequence
<220> FEATURE:
<223> OTHER INFORMATION: Synthetic primer

<400> SEQUENCE: 47
aactgctact accactgcct ac                                                   22

<210> SEQ ID NO 48
<211> LENGTH: 22
<212> TYPE: DNA
<213> ORGANISM: Artificial Sequence
<220> FEATURE:
<223> OTHER INFORMATION: Synthetic primer
```

```
<400> SEQUENCE: 48
ctactaccac tgcctactac ca                                          22

<210> SEQ ID NO 49
<211> LENGTH: 19
<212> TYPE: DNA
<213> ORGANISM: Artificial Sequence
<220> FEATURE:
<223> OTHER INFORMATION: Synthetic primer

<400> SEQUENCE: 49
ctaccactgc ctactacca                                              19

<210> SEQ ID NO 50
<211> LENGTH: 20
<212> TYPE: DNA
<213> ORGANISM: Artificial Sequence
<220> FEATURE:
<223> OTHER INFORMATION: Synthetic primer

<400> SEQUENCE: 50
cttgaggtca ctcttggaca                                             20

<210> SEQ ID NO 51
<211> LENGTH: 20
<212> TYPE: DNA
<213> ORGANISM: Artificial Sequence
<220> FEATURE:
<223> OTHER INFORMATION: Synthetic primer

<400> SEQUENCE: 51
cagccttgag gtcactcttg                                             20

<210> SEQ ID NO 52
<211> LENGTH: 19
<212> TYPE: DNA
<213> ORGANISM: Artificial Sequence
<220> FEATURE:
<223> OTHER INFORMATION: Synthetic primer

<400> SEQUENCE: 52
caggtctgag acaagaagg                                              19
```

The invention claimed is:

1. A method for producing an RNA and DNA-containing probe for use in a method of detecting a target nucleic acid based on whether or not the probe is cleaved by ribonuclease H after the probe is hybridized to the target nucleic acid which comprises the step of preparing a nucleic acid fragment containing RNA and DNA having the same sequence as a partial nucleotide sequence obtained by the RNA nucleotide conversion which is generated by a the method for processing nucleotide sequence information, wherein the method for processing nucleotide sequence information is carried out by a device for processing the nucleotide sequence information and comprises the steps of:

(1) by the device, outputting inputted data of a nucleotide sequence comprising position information of a target nucleotide wherein the inputted data of the nucleotide sequence comprise the target nucleotide, the nucleotide adjacent to the 5' side of the target nucleotide, and the nucleotide adjacent to the 3' side of the target nucleotide;

(2) by the device, generating data of a nucleotide sequence comprising the position information of the target nucleotide which is complementary to the outputted data of the nucleotide sequence comprising the position information of the target nucleotide;

(3) by the device, generating data of a nucleotide sequence which is obtained by converting the target nucleotide or the nucleotide adjacent to the target nucleotide in the nucleotide sequence into an RNA, in the data of the nucleotide sequence comprising the position information of the target nucleotide or the nucleotides each adjacent to the target nucleotide and the data of the complementary nucleotide sequence thereof; and (4) by the device, generating data of a partial nucleotide sequence comprising the position information of the target nucleotide or the nucleotides each adjacent to the target nucleotide, from the data of the nucleotide sequence and the data of the complementary nucleotide sequence thereof obtained by the RNA nucleotide conversion, wherein (a) the number of nucleotides in the partial nucleotide sequence is 7 to 14, (b) the Tm value of the partial nucleotide sequence is 25 to 40° C., wherein the Tm value is calculated under conditions having a DNA concentration of 500nM and a salt concentration of 50 mM, and
(c) the target nucleotide or the nucleotide adjacent to the target nucleotide in the nucleotide sequence is located at a position between 3 and 5 nucleotides from the 3' end of the nucleotide sequence or between 3 and 5 nucleotides from the 5' end of the nucleotide sequence,
(5) by the device, using the data of the partial nucleotide sequence obtained by the RNA nucleotide conversion to generate data of a nucleotide sequence of an RNA and DNA-containing probe used in a method of detecting a target nucleic acid based on whether or not the probe is cleaved by ribonuclease H after the probe is hybridized to target nucleic acid, and
wherein the method more efficiently generates the data of the nucleotide sequence of an RNA and DNA-containing probe wherein the probe more efficiently detects the target nucleic acid and detects the target nucleic acid with a high level of specificity.

2. A method for detecting a target nucleotide, which comprises the steps of:
(1) producing a RNA and DNA-containing probe for detecting a target nucleotide by the method according to claim 1,
(2) hybridizing to nucleic acids in a sample the RNA and DNA-containing probe
(3) applying ribonuclease H treatment to the RNA and DNA-containing probe for detecting the target nucleotide, after the hybridization step; and
(4) detecting whether or not the RNA and DNA-containing probe for detecting the target nucleotide has been cleaved by the ribonuclease H.

3. A method for producing an RNA and DNA-containing probe for use in a method of detecting a target nucleic acid based on whether or not the probe is cleaved by ribonuclease H after the probe is hybridized to the target nucleic acid, which comprises the step of preparing a nucleic acid fragment containing RNA and DNA having the same sequence as a partial nucleotide sequence obtained by the RNA nucleotide conversion which is generated by a the method for processing nucleotide sequence information, wherein the method for processing nucleotide sequence information is carried out by a device for processing the nucleotide sequence information and comprises the steps of:
(1) by the device, outputting inputted data of a nucleotide sequence comprising position information of a target nucleotide wherein the inputted data of the nucleotide sequence comprise the target nucleotide, the nucleotide adjacent to the 5' side of the target nucleotide, and the nucleotide adjacent to the 3' side of the target nucleotide;
(2) by the device, generating data of a nucleotide sequence comprising the position information of the target nucleotide which is complementary to the outputted data of the nucleotide sequence comprising the position information of the target nucleotide;
(3) by the device, generating data of a partial nucleotide sequence comprising the position information of the target nucleotide or the nucleotides each adjacent to the target nucleotide, from the outputted data of the nucleotide sequence and the generated data of the complementary nucleotide sequence, wherein
(a) the number of nucleotides in the partial nucleotide sequence is 7 to 14,
(b) the Tm value of the partial nucleotide sequence is 25 to 40° C., wherein the Tm value is calculated under conditions having a DNA concentration of 500 nM and a salt concentration of 50 mM, and
(c) the target nucleotide or the nucleotide adjacent to the target nucleotide in the nucleotide sequence is located at a position between 3 and 5 nucleotides from the 3' end of the nucleotide sequence or between 3 and 5 nucleotides from the 5' end of the nucleotide sequence; and
(4) by the device, generating data of a partial nucleotide sequence which is obtained by converting the target nucleotide or the nucleotide adjacent to the target nucleotide in the nucleotide sequence into an RNA, in the data of the partial nucleotide sequence comprising the position information of the target nucleotide or the nucleotides each adjacent to the target nucleotide,
(5) by the device, using the data of the partial nucleotide sequence obtained by the RNA nucleotide conversion to generate data of a nucleotide sequence of an RNA and DNA-containing probe used in a method of detecting a target nucleic acid based on whether or not the probe is cleaved by ribonuclease H after the probe is hybridized to target nucleic acid, and
wherein the method more efficiently generates the data of the nucleotide sequence of an RNA and DNA-containing probe wherein the probe more efficiently detects the target nucleic acid and detects the target nucleic acid with a high level of specificity.

4. A method for detecting a target nucleotide, which comprises the steps of:
(1) producing a RNA and DNA-containing probe for detecting a target nucleotide by the method according to claim 3,
(2) hybridizing to nucleic acids in a sample the RNA and DNA-containing probe;
(3) applying ribonuclease H treatment to the RNA and DNA-containing probe for detecting the target nucleotide, after the hybridization step; and
(4) detecting whether or not the RNA and DNA-containing probe for detecting the target nucleotide has been cleaved by the ribonuclease H.

5. A method for producing an RNA and DNA-containing probe for use in a method of detecting a target nucleic acid based on whether or not the probe is cleaved by ribonuclease H after the probe is hybridized to the target nucleic acid, which comprises the step of preparing a nucleic acid fragment containing RNA and DNA having the same sequence as a partial nucleotide sequence obtained by the RNA nucleotide conversion which is generated by a the method for processing nucleotide sequence information wherein the method for processing nucleotide sequence information is carried out by a device for processing the nucleotide sequence information and comprises the steps of:
(1) by the device, outputting inputted data of a nucleotide sequence comprising position information of a target nucleotide wherein the inputted data of the nucleotide sequence comprise the target nucleotide, the nucleotide adjacent to the 5' side of the target nucleotide, and the nucleotide adjacent to the 3' side of the target nucleotide;
(2) by the device, generating data of a nucleotide sequence comprising the position information of the target nucleotide which is complementary to the outputted data of the nucleotide sequence comprising the position information of the target nucleotide;
(3) by the device, making at least one determination of the following determinations:
(a) a determination as to whether or not the target nucleotide is a purine nucleotide,
(b) a determination as to whether or not the nucleotide adjacent to the 3' side of the target nucleotide is a purine nucleotide, and (c) a determination as to whether or not the nucleotide adjacent to the 5' side of the target nucleotide is a purine nucleotide, for the outputted data of the nucleotide sequence and the generated data of the complementary nucleotide sequence, whereby one nucleotide that is a purine nucleotide is determined as an RNA position from the outputted data of the nucleotide sequence and the generated data of the complementary nucleotide sequence, an outputting data of a nucleotide sequence comprising the RNA position information;

(4) by the device, generating data of a partial nucleotide sequence comprising the RNA position information from the outputted data of the nucleotide sequence comprising the RNA position information, wherein (d) the number of nucleotides in the partial nucleotide sequence is 7 to 14, (e) the Tm value of the partial nucleotide sequence is 25 to 40° C., wherein the Tm value is calculated under conditions having a DNA concentration of 500 nM and a salt concentration of 50 mM, and (f) the one nucleotide indicated at the RNA position is located at a position between 3 and 5 nucleotides from the 3' end of the nucleotide sequence or between 3 and 5 nucleotides from the 5' end of the nucleotide sequence; and (5) by the device, generating data of a partial nucleotide sequence which is obtained by converting the nucleotide determined as the RNA position into an RNA, in the data of the nucleotide sequence comprising the RNA position information or the partial nucleotide sequence comprising the RNA position information, (6) by the device, using the data of the partial nucleotide sequence obtained by the RNA nucleotide conversion to generate data of a nucleotide sequence of an RNA and DNA-containing probe used in a method of detecting a target nucleic acid based on whether or not the probe is cleaved by ribonuclease H after the probe is hybridized to target nucleic acid, and wherein the method more efficiently generates the data of the nucleotide sequence of an RNA and DNA-containing probe wherein the probe more efficiently detects the target nucleic acid and detects the target nucleic acid with a high level of specificity.

6. A method for detecting a target nucleotide, which comprises the steps of:
(1) producing a RNA and DNA-containing probe for detecting a target nucleotide by the method according to claim 5,
(2) hybridizing to nucleic acids in a sample the RNA and DNA-containing probe;
(3) applying ribonuclease H treatment to the RNA and DNA-containing probe for detecting the target nucleotide, after the hybridization step; and
(4) detecting whether or not the RNA and DNA-containing probe for detecting the target nucleotide has been cleaved by the ribonuclease H.

* * * * *